US011793884B2

(12) United States Patent
Pei et al.

(10) Patent No.: US 11,793,884 B2
(45) Date of Patent: Oct. 24, 2023

(54) CYCLIC PEPTIDYL INHIBITORS OF CAL-PDZ BINDING DOMAIN

(71) Applicant: Ohio State Innovation Foundation, Columbus, OH (US)

(72) Inventors: Dehua Pei, Columbus, OH (US); Patrick G. Dougherty, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/965,713

(22) PCT Filed: Jan. 29, 2019

(86) PCT No.: PCT/US2019/015697
§ 371 (c)(1),
(2) Date: Jul. 29, 2020

(87) PCT Pub. No.: WO2019/148195
PCT Pub. Date: Aug. 1, 2019

(65) Prior Publication Data
US 2021/0038737 A1 Feb. 11, 2021

Related U.S. Application Data

(60) Provisional application No. 62/623,209, filed on Jan. 29, 2018.

(51) Int. Cl.
| | | |
|---|---|---|
| C07K 7/06 | (2006.01) | |
| A61K 38/00 | (2006.01) | |
| A61K 47/64 | (2017.01) | |
| A61P 11/00 | (2006.01) | |
| A61K 31/47 | (2006.01) | |
| A61K 38/08 | (2019.01) | |
| A61K 45/06 | (2006.01) | |
| C07K 14/47 | (2006.01) | |

(52) U.S. Cl.
CPC ............ *A61K 47/645* (2017.08); *A61K 31/47* (2013.01); *A61K 38/08* (2013.01); *A61K 45/06* (2013.01); *A61P 11/00* (2018.01); *C07K 7/06* (2013.01); *C07K 14/47* (2013.01)

(58) Field of Classification Search
None
See application file for complete search history.

(56) References Cited

U.S. PATENT DOCUMENTS

| | | |
|---|---|---|
| 7,495,103 B2 | 2/2009 | Hadida-Ruah |
| 8,507,534 B2 | 8/2013 | Keshavarz-Shokri et al. |
| 8,754,224 B2 | 6/2014 | Hurter et al. |
| 8,999,919 B2 | 4/2015 | Madden et al. |
| 9,139,530 B2 | 9/2015 | Hurter et al. |
| 9,216,969 B2 | 12/2015 | Hadida et al. |
| 10,626,147 B2 | 4/2020 | Pei et al. |
| 2012/0071504 A1 | 3/2012 | Yang et al. |
| 2017/0190743 A1 | 7/2017 | Pei et al. |
| 2017/0355730 A1 | 12/2017 | Pei et al. |
| 2019/0282654 A1 | 9/2019 | Pei et al. |
| 2019/0309020 A1 | 10/2019 | Pei et al. |

FOREIGN PATENT DOCUMENTS

| | | |
|---|---|---|
| WO | 2016177898 A1 | 11/2016 |
| WO | 2018/089648 | 5/2018 |
| WO | 2018/098231 | 5/2018 |

OTHER PUBLICATIONS

International Search Report and Written Opinion issued by the International Searching Authority (ISA/US) in PCT Application No. PCT/US2019/015697 dated Jul. 19, 2019. 11 pages.
Qian, Ziqing, et al. "Intracellular delivery of peptidyl ligands by reversible cyclization: discovery of a PDZ domain inhibitor that rescues CFTR activity." Angewandte Chemie International Edition 54.20 (2015): 5874-5878.
Eisenberg, David, Robert M. Weiss, and Thomas C. Terwilliger. "The hydrophobic moment detects periodicity in protein hydrophobicity." Proceedings of the National Academy of Sciences 81.1 (1984): 140-144.
Engelman, D. M., T. A. Steitz, and A. Goldman. "Identifying nonpolar transbilayer helices in amino acid sequences of membrane proteins." Annual review of biophysics and biophysical chemistry 15.1 (1986): 321-353.
Kyte, Jack, and Russell F. Doolittle. "A simple method for displaying the hydropathic character of a protein." Journal of molecular biology 157.1 (1982): 105-132.
Hopp, Thomas P., and Kenneth R. Woods. "Prediction of protein antigenic determinants from amino acid sequences." Proceedings of the National Academy of Sciences 78.6 (1981): 3824-3828.
Janin, J. O. E. L. "Surface and inside volumes in globular proteins." Nature 277.5696 (1979): 491-492.
Shrake, Andrew, and John A. Rupley. "Environment and exposure to solvent of protein atoms. Lysozyme and insulin." Journal of molecular biology 79.2 (1973): 351-371.

(Continued)

*Primary Examiner* — Thomas S Heard
(74) *Attorney, Agent, or Firm* — Meunier Carlin & Curfman LLC

(57) ABSTRACT

Described herein, in various embodiments, are peptides comprising: (i) a cyclic cell-penetrating peptide sequence (cCPP) and (ii) a CAL-PDZ binding sequence, which is conjugated, directly or indirectly, to an N-terminus of an amino acid in the cCPP, to a C-terminus of an amino acid on the cCPP, or on a side chain of an amino acid in the cCPP. In other embodiments, the peptides further comprise a physiologically cleavable group, wherein after entering the cell, the physiologically cleavable group is reduced, thereby providing a linear peptide. Without being bound by theory, the inventors discovered that the amino acid sequence in the cCPP, which facilities cytosolic delivery of the CAL-PDZ binding sequence also, surprisingly and unexpectedly, synergistically improves binding of CAL-PDZ binding sequence to the CAL-PDZ binding domain. Additionally, the cCPP sequence may also improve selectivity of the CAL-PDZ binding sequence for the CAL-PDZ domain relative to other PDZ binding domains.

8 Claims, 12 Drawing Sheets

Specification includes a Sequence Listing.

(56) References Cited

OTHER PUBLICATIONS

Tien, Matthew Z., et al. "Maximum allowed solvent accessibilites of residues in proteins." PloS one 8.11 (2013): e80635.
Roberts, Kyle E., et al. "Computational design of a PDZ domain peptide inhibitor that rescues CFTR activity." PLoS Comput Biol 8.4 (2012): e1002477.
International Preliminary report on Patentability issued for Application No. PCT/US2019/015697, dated Aug. 13, 2020.
Partial Supplementary Search report issued for European Application No. 19743190, dated Jan. 19, 2022.
Seisel, Quentin, et al. "Optimization of the process of inverted peptides (PIPEPLUS) to screen PDZ domain ligands." Bioorganic & medicinal chemistry letters 27.14 (2017): 3111-3116.

CYCLIC PEPTIDYL INHIBITORS OF CAL-PDZ BINDING DOMAIN

CROSS-REFERENCE TO RELATED APPLICATIONS

This application is a national stage application filed under 35 U.S.C. § 371 of PCT/US2019/015697 filed Jan. 29, 2019, which claims priority to U.S. Provisional Application No. 62/623,209, filed Jan. 29, 2018, which is incorporated by reference in its entirety for all purposes.

STATEMENT REGARDING FEDERALLY FUNDED RESEARCH

This invention was made with government support under GM110208 and GM122459 awarded by the National Institutes of Health. The government has certain rights in the invention.

BACKGROUND

Cystic fibrosis (CF) is the most common life-limiting autosomal recessive disease among people of European heritage. In the United States and Canada, about 34,000 individuals have CF. The total number of CF patients in the developed world is estimated to be 70,000 and their average life expectancy is between 42 and 50 years.

CF is attributed to mutations of the cystic fibrosis transmembrane conductance regulator (CFTR) gene, which affecting chloride ion channel function, leading to dysregulation of epithelial fluid transport in the lung, pancreas and other organs. Complications resulting from mutated CFTR include thickened mucus in the lungs with frequent respiratory infections, and pancreatic insufficiency giving rise to malnutrition and diabetes. These conditions lead to chronic disability and reduced life expectancy. In male patients, the progressive obstruction and destruction of the developing vas deferens (spermatic cord) and epididymis appear to result from abnormal intraluminal secretions, causing congenital absence of the vas deferens and male infertility.

Until recently, the standard of treatment for CF involved intravenous, inhaled, and oral antibiotics to treat chronic and acute infections. Mechanical devices and inhalation medications have also been used to alter and clear the thickened mucus. At best, these treatments delay the decline in organ function.

Recent strategies to treat CF have focused on therapeutic agents that improve chloride ion channel function (known as potentiators) and therapeutic agents that correct improperly folded mutant CFTR protein (known as correctors). However, mutant CFTR exhibit increased susceptibility to lysosomal degradation, and therefore potentiators and correctors are not able to fully restore CFTR function.

Thus, there exists a need for therapeutic agents which protect CFTR from lysosomal degradation. The present disclosures addresses this need.

SUMMARY

Described herein, in various embodiments, are peptides comprising: (i) a cyclic cell-penetrating peptide sequence (cCPP) and (ii) a CAL-PDZ binding sequence, which is conjugated, directly or indirectly, to an N-terminus of an amino acid in the cCPP, to a C-terminus of an amino acid on the cCPP, or on a side chain of an amino acid in the cCPP. In other embodiments, the peptides further comprise a physiologically cleavable group, wherein after entering the cell, the physiologically cleavable group is reduced, thereby providing a linear peptide. Without being bound by theory, the inventors discovered that the amino acid sequence in the cCPP, which facilities cytosolic delivery of the CAL-PDZ binding sequence also, surprisingly and unexpectedly, synergistically improves binding of CAL-PDZ binding sequence to the CAL-PDZ binding domain. Additionally, the cCPP sequence may also improve selectivity of the CAL-PDZ binding sequence for the CAL-PDZ domain relative to other PDZ binding domains.

In some such embodiments, the peptides have $K_D$ of less than or equal to 0.5 µM for the CAL-PDZ domain.

In some embodiments, the peptides disclosed herein have a structure according to Formula I or II:

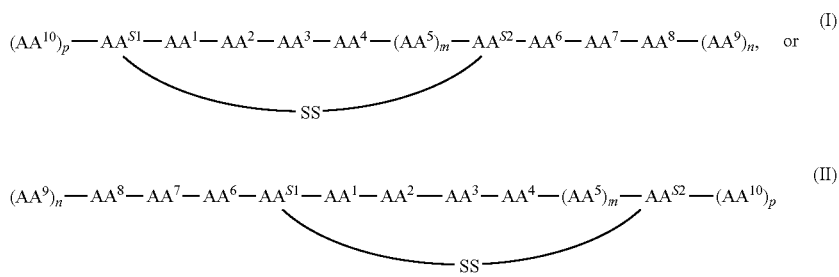

or a pharmaceutically acceptable salt thereof,
wherein:
  $AA^1$, $AA^2$, $AA^3$, $AA^4$, $AA^6$, $AA^7$, and $AA^8$ are independently selected from an amino acid, which is optionally substituted with one or more substituents;
  $AA^5$, $AA^9$, and $AA^{10}$, at each instance and when present, is independently selected from an amino acid, which is optionally substituted with one or more substituents;
  m is a number in the range of from 0 to 10;
  n is a number in the range of from 0 to 2000;
  p is a number in the range of from 0 to 10; and
  each of $AA^{S1}$ and $AA^{S2}$ is independently an amino acid which forms a disulfide bond (ss);

wherein at least two of $AA^1$, $AA^2$, $AA^3$, $AA^4$, and $AA^5$ at each instance and when present, are arginine, and at least two of $AA^1$, $AA^2$, $AA^3$, $AA^4$, and $AA^5$ at each instance and when present are independently a hydrophobic amino acid which is optionally substituted; and wherein -$AA^6$-$AA^7$-$AA^8$-$(AA^9)_n$ a peptide sequence which binds to the CAL-PDZ domain;

provided that the peptide of Formula I is not

CRRRRFWQCTRV.

In some embodiments, any four consecutive amino acids in the sequence $AA^1$-$AA^2$-$AA^3$-$AA^4$-$(AA^5)_m$ are selected from the group consisting of: (i) $AA_{H2}$-$AA_{H1}$-R-r; (ii) $AA_{H2}$-$AA_{H1}$-r-R; (iii) R-r-$AA_{H1}$-$AA_{H2}$; and (iv) r-R-$AA_{H1}$-$AA_{H2}$, wherein each of $AA_{H1}$ and $AA_{H2}$ are independently a hydrophobic amino acid. In some other embodiments, the hydrophobic amino acid is selected from glycine, alanine, tert-butyl-glycine, valine, leucine, isoleucine, methionine, phenylalanine, tryptophan, proline, naphthylalanine, phenylglycine, homophenylalanine, tyrosine, cyclohexylalanine, norleucine, 3-(3-benzothienyl)-alanine, tert-leucine, pipecolic acid, or nicotinoyl lysine, each of which is optionally substituted with one or more substituents. In particular embodiments, at least two of $AA^1$, $AA^2$, $AA^3$, $AA^4$, and $AA^5$, at each instance and when present, are naphthylalanine, 3-(3-benzothienyl)-alanine, pipecolic acid, or combinations thereof, each of which is optionally substituted with one or more substituents.

In some embodiments, at least three of $AA^6$, $AA^7$, $AA^8$, and $AA^9$ at each instance and when present, are independently selected from threonine, serine, tert-butyl-glycine, valine, leucine, isoleucine, lysine, and arginine. In some embodiments, at of $AA^6$, $AA^7$, $AA^8$, and $AA^9$ at each instance and when present, are independently selected from threonine, tert-butyl-glycine, and arginine.

In some embodiments:
in Formula I:
when p is 0, the N-terminus of $AA^{S1}$ is H, —C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; or
when p is a number from 1 to 10, the N-terminus of $AA^{10}$ is C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; and
in Formula II:
when p is 0, the C-terminus of $AA^{S2}$ is OH, $OR^2$, or $NHR^2$, wherein $R^2$ is an alkyl, aryl, heteroaryl, or at least one amino acid; or
when p is a number from 1 to 10, the C-terminus of $AA^{10}$ is OH, $OR^2$, or $NHR^2$, wherein $R^2$ is an alkyl, aryl, heteroaryl, or at least one amino acid.

In some embodiments, each of $AA^{S1}$ and $AA^{S2}$ are independently selected from:

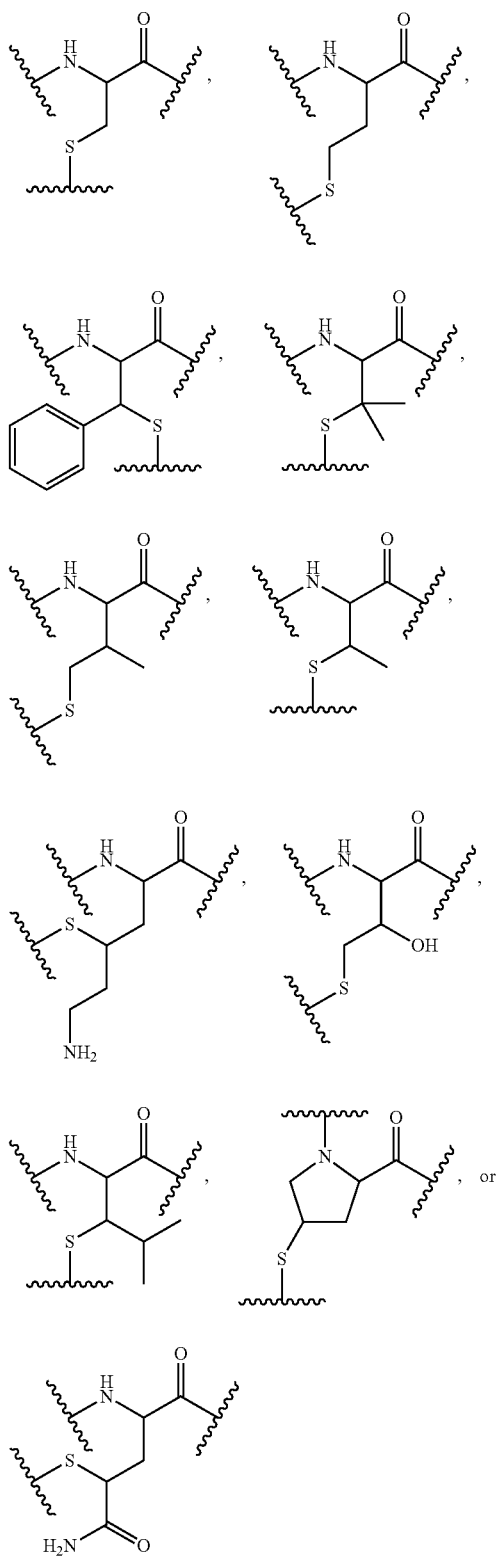

In some embodiments, the peptides described herein (e.g., the peptides of Formula I and/or II) are selected from Table 6, Table 7, and Table 8. In some embodiments, peptides described herein (e.g., the peptides of Formula I and/or II) have the following structure:

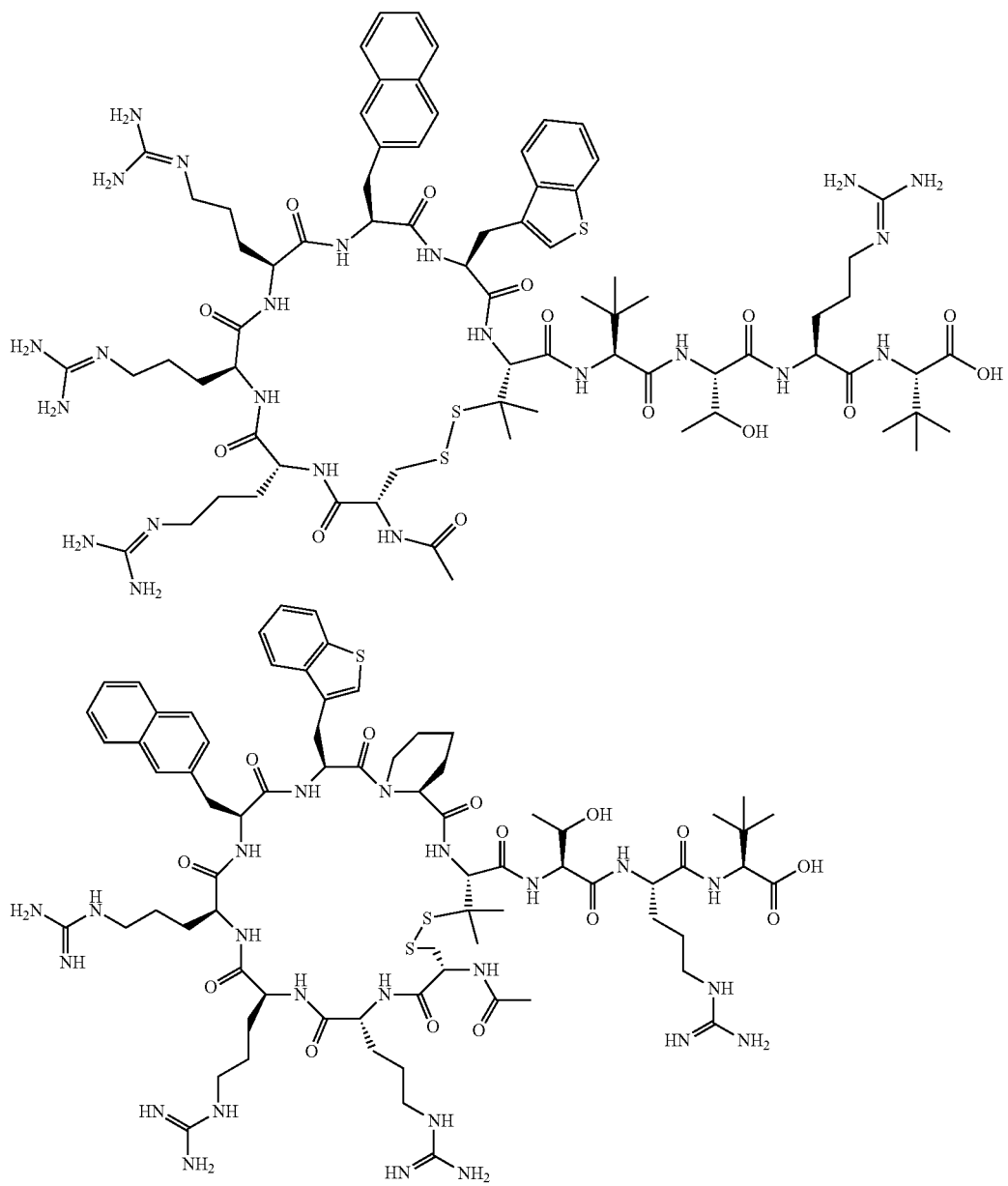

Peptide 32 (PGD97)

In some embodiments, the peptides disclosed herein have a structure according to Formula IA or IIA:

$$(AA^{10})_p\text{-}AA^{S1'}\text{-}AA^1\text{-}AA^2\text{-}AA^3\text{-}AA^4\text{-}(AA^5)_m\text{-}AA^{S2'}\text{-}AA^6\text{-}AA^7\text{-}AA^8\text{-}(AA^9)_n \quad (IA)$$

$$_n(AA^9)\text{-}AA^8\text{-}AA^7\text{-}AA^6\text{-}AA^{S1'}\text{-}AA^1\text{-}AA^2\text{-}AA^3\text{-}AA^4\text{-}(AA^5)_m\text{-}AA^{S2'}\text{-}(AA^{10})_p \quad (IIA)$$

wherein:
each of $AA^1$, $AA^2$, $AA^3$, $AA^4$, $AA^6$, $AA^7$, and $AA^8$ are independently selected from an amino acid, which is optionally substituted with one or more substituents;
$AA^5$ at each instance and when present, are independently selected from an amino acid, which is optionally substituted with one or more substituents;
$AA^9$ at each instance and when present, are independently selected from an amino acid, which is optionally substituted with one or more substituents;
$AA^{10}$ at each instance and when present, are independently selected from an amino acid, which is optionally substituted with one or more substituents;
m is a number in the range of from 0 to 10;
n is a number in the range of from 0 to 2000;
p is a number in the range of from 0 to 10; and
each of $AA^{S1'}$ and $AA^{S2'}$ is independently an amino acid having a thiol group;
wherein at least two of $AA^1$, $AA^2$, $AA^3$, $AA^4$, and $AA^5$ at each instance and when present, are arginine, and at least two of $AA^1$, $AA^2$, $AA^3$, $AA^4$, and $AA^5$ at each instance and when present are independently a hydrophobic amino acid which is optionally substituted; and wherein -AA⁶-AA⁷-AA⁸-(AA⁹)ₙ is a peptide sequence which binds to the CAL-PDZ domain;
provided that the peptide of Formula I is not CRRRRFWQCTRV (SEQ ID NO:1).

In some embodiments, any four consecutive amino acids in the sequence AA¹-AA²-AA³-AA⁴-(AA⁵)ₘ are selected from the group consisting of: (i) $AA_{H2}$-$AA^{H1}$-R-r; (ii) $AA_{H2}$-$AA_{H1}$-r-R; (iii) R-r-$AA_{H1}$-$AA_{H2}$; and (iv) r-R-$AA_{H1}$-$AA_{H2}$, wherein each of $AA_{H1}$ and $AA_{H2}$ are independently a hydrophobic amino acid. In some other embodiments, the hydrophobic amino acid is selected from glycine, alanine, tert-butyl-glycine, valine, leucine, isoleucine, methionine, phenylalanine, tryptophan, proline, naphthylalanine, phenylglycine, homophenylalanine, tyrosine, cyclohexylalanine, norleucine, 3-(3-benzothienyl)-alanine, tert-leucine, pipecolic acid, or nicotinoyl lysine, each of which is optionally substituted with one or more substituents. In particular embodiments, at least two of AA¹, AA², AA³, AA⁴, and AA⁵, at each instance and when present, are naphthylalanine, 3-(3-benzothienyl)-alanine, pipecolic acid, or combinations thereof, each of which is optionally substituted with one or more substituents.

In some embodiments, at least three of AA⁶, AA⁷, AA⁸, and AA⁹ at each instance and when present, are independently selected from threonine, serine, tert-butyl-glycine, valine, leucine, isoleucine, lysine, and arginine. In some embodiments, at least three of AA⁶, AA⁷, and AA⁹ at each instance and when present, are independently selected from threonine, tert-butyl-glycine, and arginine.

In some embodiments:
in Formula IA:
when p is 0, the N-terminus of $AA^{S1}$ is H, —C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; or
when p is a number from 1 to 10, the N-terminus of $AA^{10}$ is C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; and
in Formula IIA:
when p is 0, the C-terminus of $AA^{S2}$ is OH, $OR^2$, or $NHR^2$, wherein $R^2$ is an alkyl, aryl, heteroaryl, or at least one amino acid; or
when p is a number from 1 to 10, the C-terminus of $AA^{10}$ is OH, $OR^2$, or $NHR^2$, wherein $R^2$ is an alkyl, aryl, heteroaryl, or at least one amino acid.

In some embodiments, each of $AA^{S1'}$ and $AA^{S2'}$ are independently selected from the following amino acids:

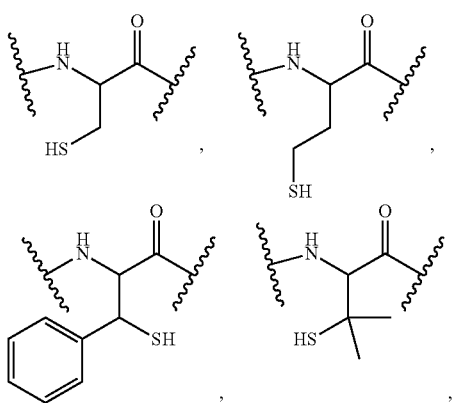

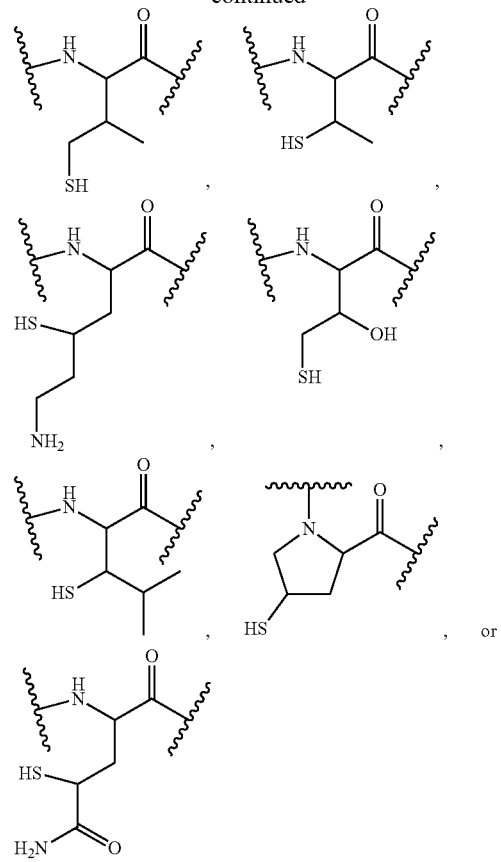

In some embodiments, the disclosure provides for a cell comprising one or more of the peptides described herein.

In some embodiments, the disclosure provides for pharmaceutical compositions comprising one or more of the peptides described herein.

In some embodiments, the disclosure provides for methods of inhibiting binding of ligands to the CAL-PDZ binding domain in a patient in need thereof, comprising administering one or more peptides or pharmaceutical compositions disclosed to the patient. In some embodiments, the disclosure provides for methods of treating cystic fibrosis in a patient in need thereof, comprising administering one or more peptides or pharmaceutical compositions disclosed to the patient, thereby treating cystic fibrosis. In some embodiments, the method further comprise administering at least one drug used to treat cystic fibrosis. In some embodiments, the additional drug or drugs corrects an improperly folded mutant CFTR protein, is a potentiator of ion channel gating, or combinations thereof. In some embodiments, the drug that corrects an improperly folded mutant CFTR protein is Lumacaftor, Tezacaftor, VX-152, or VX-440, or combinations thereof. In some embodiments, the drug that is a potentiator of ion channel gating is Ivacaftor.

BRIEF DESCRIPTION OF FIGURES

FIG. 6 (*b*) Fold of reduction in binding affinity upon Ala substitution at each position of peptide 29.

FIG. 8 (*b*) shows structures of three predicted proteolytic fragments of peptide 29.

FIG. 12 (*b*) shows short-circuit current measured in CFBE cells following the same treatment after 24 h (n=3). FIG. 12 (*c*) shows short-circuit current measured in primary cells following the same treatment after 24 h (n=3).

FIG. 13 (*a*) Macrophages from patient A; FIG. 13 (*b*) macrophages from patient B; and FIG. 13 (*c*) quantitation of (a) and (b) by densitometry.

DETAILED DESCRIPTION

Definitions

Figure 1:
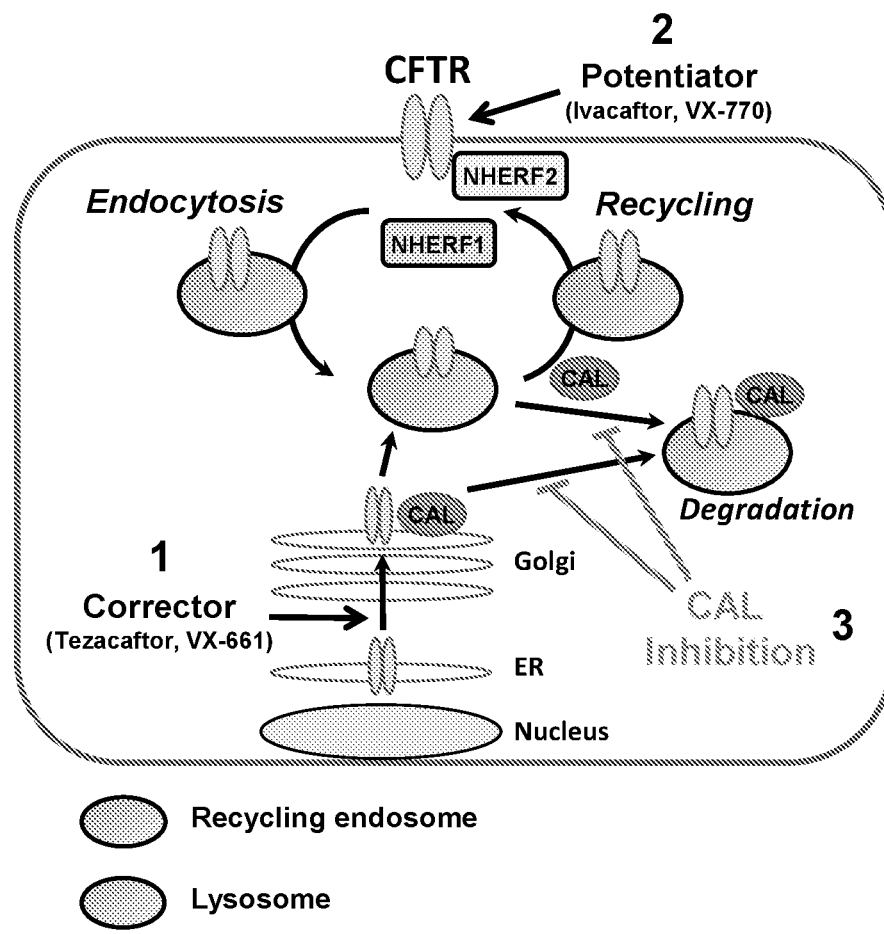
FIG. 1 schematically illustrates intracellular trafficking, endocytosis, and recycling of CFTR among the different membranous compartments and the effect of correctors (1), potentiators (2), and stabilizers (3) on mutant CFTR biogenesis and function.

While the following terms are believed to be well understood by one of ordinary skill in the art, the following definitions are set forth to facilitate explanation of the presently disclosed subject matter.

The term "CAL PDZ binding sequence" refers to a sequence of amino acids which binds to the CAL PDZ binding domain.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.), as if each and every value and subrange were expressly recited. Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a peptide" refers to one or more peptides or at least one peptide. As such, the terms "a" (or "an"), "one or more" and "at least one" are used interchangeably herein. In addition, reference to "an inhibitor" by the indefinite article "a" or "an" does not exclude the possibility that more than one of the peptides is present, unless the context clearly requires that there is one and only one of the inhibitors.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

As used herein the terms "treating" or "treatment" includes prevention; delay in onset; diminution, eradication, or delay in exacerbation of signs or symptoms after onset; prevention of relapse; and ameliorating one or more conditions associated with a CF.

"Acyl" or "acyl group" refers to a radical of the formula —C(O)$R_a$, wherein $R_a$ is an alkyl, alkenyl, alkynyl, alkoxy, alkylamino, thioalkyl, aryl, cycloalkyl, cycloalkenyl, cycloalkynyl, heterocyclyl, or heteroaryl.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, sec-propyl, n-butyl, sec-butyl, t-butyl, n-pentyl, n-hexyl, n-heptyl, n-octyl, n-nonyl, n-decyl, n-undecyl, and n-dodecyl. Unless stated otherwise specifically in the specification, an alkyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

The term "substituted" used herein means any amino acid disclosed herein wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, "substituted" also encompasses instances in which one or more carbon atoms on an amino acid side chain are replaced by a heteroatom.

As used herein, the symbol

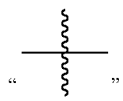

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

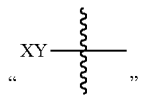

indicates that the chemical entity "XY" is bonded to another chemical entity via the point of attachment bond. Furthermore, the specific point of attachment to the non-depicted chemical entity can be specified by inference. For example, the compound CH$_3$—R$^3$, when R$^3$ is "XY", the point of attachment bond is the same bond as the bond by which R$^3$ is depicted as being bonded to CH$_3$.

CAL-PDZ Inhibitors

Disclosed herein are peptides which inhibit binding of CFTR to the CAL-PDZ binding domain.

CFTR is an integral membrane protein and a chloride ion channel in vertebrates that is encoded by the cftr gene. As an ABC transporter, CFTR conducts chloride ions across epithelial cell membranes. The newly synthesized CFTR polypeptide is exported to the ER, where it folds into the proper 3D structure (FIG. 1).

Mutant CFTRs that cannot properly fold (e.g., F508del) are degraded by the proteasome resulting in little or no CFTR at the plasma membrane. In presence of CFTR correctors, these mutant CFTRs can reach the plasma membrane but may have other defects. For example, the F508del mutant is also defective in ion channel gating and requires a potentiator to render it in the open state. Furthermore, CFTR undergoes constant endocytosis and recycling at the plasma membrane. The C-terminus of the CFTR is recognized by the PDZ domains of at least two different classes of proteins—CFTR-associated ligand (CAL) and Na$^+$/H$^+$ exchanger regulatory factor (NHERF). Binding to the PDZ domain of CAL targets CFTR to the lysosome for degradation, whereas binding to the PDZ domains of the NHERF family proteins recycles it back to the plasma membrane. For reasons that are not yet fully understood, mutant CFTRs (e.g., F508del) are more prone to lysosomal degradation compared to WT CFTR. Thus, even when both folding/trafficking and gating defects are completely corrected with the help of correctors and potentiators, a mutant CFTR may still not be able to reach WT ion transport activity because excessive lysosomal degradation reduces its cell-surface level.

Given the role of CAL PDZ in CFTR degradation, the inventors designed various peptide sequences which inhibit CAL-mediated CFTR degradation to stabilize the mutant CFTR proteins at the plasma membrane and increase their ion transport activities.

The inventors discovered that amino acid residues which have the ability to penetrate a cell membrane (i.e., a cell-penetrating peptide sequence) also have an affinity for the CAL PDZ binding domain, and thereby contribute to the CAL PDZ binding affinity of a CAL PDZ binding sequence. Although cyclic sequences exhibit higher cytosolic delivery efficiency and greater metabolic stability during circulation, linear amino acid sequences exhibit a stronger binding affinity to CAL PDZ. Thus, in certain embodiments, the peptides disclosed herein are cyclized through a physiologically cleavable group (e.g., disulfide group) which allows for a linear sequence (comprising the cell penetrating sequence and the CAL-PDZ binding sequence) to bind to the CAL PDZ domain. That is, outside of the cell (e.g., in circulation), the peptides disclosed herein are cyclic, and after entering the cell, the physiologically cleavable sequence is reduced to generate a linear sequence which then interacts with the CAL-PDZ binding domain.

Disclosed herein, in various embodiments, are peptides comprising (i) a cyclic cell-penetrating peptide sequence (cCPP) and (ii) a CAL-PDZ binding sequence conjugated, directly or indirectly, to one or more of an N-terminus of an amino acid in the cCPP, to a C-terminus of an amino acid on the cCPP, or on a side chain of an amino acid in the cCPP. As discussed above, the cCPP sequence can be optimized to improve CAL PDZ binding affinity of the peptides disclosed herein compared to the binding affinity of an otherwise identical CAL PDZ binding sequence which is not conjugated to a cCPP. Therefore, "cCPP" should not be interpreted to refer to amino acids which function solely to facilitate cytosolic delivery, as such peptides in the cCPP sequence may also function to improve CAL PDZ binding In some embodiments, the peptide has Kd of less than or equal to about 0.5 µM for the CAL-PDZ domain, e.g., less than or equal to about 0.4 µM, about 0.3 µM, about 0.2 µM, about 0.1 µM, about 90 nM, about 80 nM, about 70 nM, about 60 nM, about 50 nM, about 40 nM, about 30 nM, about 10 nM, about 9 nM, about 8 nM, about 7 nM, about 6 nM, about 5 nM, about 4 nM, about 3 nM, about 2 nM, and about 1 nM, inclusive of all values and ranges therebetween.

In some embodiments, the peptides disclosed herein have an IC$_{50}$ for CAL-PDZ of about 10,000 nM or less, e.g., about 9,000 nM, about 8,000 nM, about 7,000 nM, about 6,000 nM, about 5,000 nM, about 4,000 nM, about 3,000 nM, about 2,000 nM, about 1,000 nM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 9 nM, about 8 nM, about 7 nM, about 6 nM, about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, or less, inclusive of all values and ranges therebetween. In particular embodiments, the peptide disclosed herein have an IC$_{50}$ for CAL-PDZ in the range of from about 100 nM to about 1 nM.

Additionally, as discussed herein, the cCPP sequence also improve selectivity of the CAL PDZ binding sequence for the CAL-PDZ binding domain of the peptides disclosed herein. In some embodiments, CAL-PDZ selectivity of the present peptides is compared to the selectivity of an otherwise identical CAL-PDZ binding sequence which is not conjugated to a cCPP. In some embodiments, CAL-PDZ binding selectivity is measured as in terms of the binding affinity of the peptide for CAL-PDZ compared to other PDZ domains in the cell, e.g., PDZ domain on NHERF. In some embodiments, the peptides disclosed herein have a selectivity for CAL-PDZ that is improved by about 1.1 fold, about 1.5, fold, about 2 fold, about 3 fold, about 4 fold, about 5 fold, about 6 fold, about 7 fold, about 8 fold, about 9 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold about 45 fold, about 50 fold, about 55 fold, about 60 fold about 65 fold, about 70 fold, about 80 fold, about 90 fold, about 100 fold, about 150 fold, about 200 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, or about 1000 fold, or more, inclusive of all values, ranges and subranges therebetween.

In some embodiments, the peptides disclosed herein have relative cytosolic uptake efficiency in the range of from about 10% to about 1000%, e.g., about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, about 590%, about 600%, about 610%, about 620%, about 630%, about 640%, about 650%, about 660%, about 670%, about 680%, about 690%, about 700%, about 710%, about 720%, about 730%, about 740%, about 750%, about 760%, about 770%, about 780%, about 790%, about 800%, about 810%, about 820%, about 830%, about 840%, about 850%, about 860%, about 870%, about 880%, about 890%, about 900%, about 910%, about 920%, about 930%, about 940%, about 950%, about 960%, about 970%, about 080%, and about 1000%, inclusive of all values and subranges therebetween. In particular embodiments, the peptides disclosed herein have relative cytosolic uptake efficiency in the range of from about 20% to about 600%.

In some embodiments, the peptides disclosed herein have a structure according to Formula I or II:

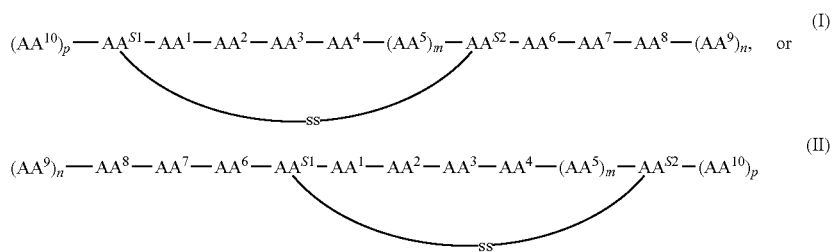

In some embodiments, $AA^1$, $AA^2$, $AA^3$, $AA^4$, $AA^6$, $AA^7$, and $AA^8$ are independently selected from an amino acid, which is optionally substituted with one or more substituents. In some embodiments, $AA^5$, at each instance and when present, is independently selected from an amino acid, which is optionally substituted with one or more substituents. In some embodiments, In some embodiments, $AA^9$, at each instance and when present, is independently selected from an amino acid, which is optionally substituted with one or more substituents. In some embodiments, $AA^{10}$, at each instance and when present, is independently selected from an amino acid, which is optionally substituted with one or more substituents. The term "cCPP" as used herein, refers to the following amino acid sequence: -$AA^1$-$AA^2$-$AA^3$-$AA^4$-$(AA^5)_m$-. The term "CAL PDZ binding sequence" as used herein refers to the following sequence: -$AA^6$-$AA^7$-$AA^8$-$(AA^9)_n$, which is a peptide sequence which binds to the CAL-PDZ domain. As discussed herein, the inventors surprisingly discovered that the cCPP sequence not only effectively delivers the CAL PDZ binding sequence to the cytosol of a cell, but also improves the binding affinity and selectivity of the CAL PDZ binding sequence.

In some embodiments, m is any number which allows for cyclization of the amino acid sequence and still allows for uptake by the cell. In certain embodiments, m is a number in the range of from 0 to 10 (e.g., 0, 1, 2, 3, 4, 5, 6, 7, 8, 9, and 10, inclusive of all values and subranges therebetween).

In some embodiments, n is a number in the range of from 0 to 2000 (e.g., 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, 1800, 1850, 1900, 1950, and 2000, inclusive of all values and subranges therebetween). Thus, the CAL PDZ binding sequence may include a sequence of several amino acids which bind to the CAL PDZ binding domain, or it can include a full length protein (either naturally occurring or synthetic) at least a portion of which binds to the CAL PDZ binding domain.

In some embodiments, p is a number in the range of from 0 to 10 (e.g., 0, 1, 2, 3, 4, 5, 6, 7, 8, 9, and 10, inclusive of all values and subranges therebetween).

The N and/or C terminus of the peptide disclosed herein may be protected with a suitable non-peptidyl moiety. For example, in embodiments in which p is 0, the N terminus of $AA^{S1}$ in Formula I or the C terminus of $AA^{S2}$ in Formula II may be protected with any suitable non-peptidyl moiety, e.g., those described herein. For example, in Formula I, when p is 0, the N-terminus of AAR may be H, —C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; in Formula II, when p is 0, the C-terminus of $AA^{S2}$ may be OH, $OR^2$, or $NHR^2$, wherein $R^2$ is an alkyl, aryl, or heteroaryl. Similarly, when p is 1 or more, the N or C terminus of $AA^{10}$ may be protected with any suitable non-peptidyl moiety. For example, in Formula I, when p is a number from 1 to 10, the N-terminus of $AA^{10}$ may be —C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; in Formula II, when p is a number from 1 to 10, the C-terminus of $AA^{10}$ is OH, $OR^2$, or $NHR^2$, wherein $R^2$ is an alkyl, aryl, heteroaryl, or at least one amino acid.

In some embodiments, each of $AA^{S1}$ and $AA^{S2}$ is independently an amino acid which forms a disulfide bond (ss).

In some embodiments, at least two of $AA^1$, $AA^2$, $AA^3$, $AA^4$ and $AA^5$ are arginine which is optionally substituted. In some embodiments, at least two of $AA^1$, $AA^2$, $AA^3$, $AA^4$ $AA^5$ are independently a hydrophobic amino acid which is optionally substituted.

In particular embodiments, the peptides disclosed herein (e.g., the peptides of Formula I) are not:

The amino acids in the peptides disclosed herein may be independently selected from any natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, 2,3-diaminopropionic acid a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
| --- | --- | --- |
| Alanine | Ala (A) | ala (a) |
| Allosoleucine | AIle | aile |
| Arginine | Arg (R) | arg (r) |
| Asparagine | Asn (N) | asn (n) |
| Cspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| Glutamic acid | Glu (E) | glu (e) |
| Glutamine | Gln (Q) | gln (q) |
| Glycine | Gly (G) | gly (g) |
| Histidine | His (H) | his (h) |
| Homoproline (aka pipecolic acid) | Pip (Θ) | Pip (θ) |
| Isoleucine | Ile (I) | ile (i) |
| Leucine | Leu (L) | leu (l) |
| Lysine | Lys (K) | lys (k) |
| Methionine | Met (M) | met (m) |
| Napthylalanine | Nal (Φ) | nal (φ) |
| Norleucine | Nle (Ω) | nle |
| Phenylalanine | Phe (F) | phe (F) |
| Phenylglycine | Phg (Ψ) | phg |
| 4-(phosphonodifluoromethyl)phenylalanine | $F_2$Pmp (Λ) | $f_2$pmp |
| Proline | Pro (P) | pro (p) |
| Sarcosine | Sar (Ξ) | sar |
| Selenocysteine | Sec (U) | sec (u) |
| Serine | Ser (S) | ser (s) |
| Threonine | Thr (T) | thr (y) |
| Tyrosine | Tyr (Y) | tyr (y) |
| Tryptophan | Trp (W) | trp (w) |
| Valine | Val (V) | val (v) |
| Tert-butyl-glycine | Tle | tle |
| Penicillamine | Pen | pen |
| Homoarginine | HomoArg | homoarg |
| Nicotinyl-lysine | Lys(NIC) | lys(NIC) |
| Triflouroacetyl-lysine | Lys(TFA) | lys(TFA) |

TABLE 1-continued

Amino Acid Abbreviations

| Amino Acid | Abbreviations* L-amino acid | Abbreviations* D-amino acid |
|---|---|---|
| Methyl-leucine | MeLeu | meLeu |
| 3-(3-benzothienyl)-alanine | Bta | bta |

*single letter abbreviations: when shown in capital letters herein it indicates the L-amino acid form, when shown in lower case herein it indicates the D-amino acid.

Cell Penetrating Peptide Sequence

Cyclic cell-penetrating peptides (cCCP) allow for delivery of otherwise impermeable CAL PDZ binding sequences to be efficiently delivered to the cytosol of a cell. The cCPP of the peptides disclosed herein may be or include any amino sequence which facilitates cellular uptake of a CAL PDZ binding sequence. Suitable cCPPs include naturally occurring sequences, modified sequences, and synthetic sequences. In embodiments, the total number of amino acids in the cCPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the cCPPs disclosed herein comprise about 4 to about to about 13 amino acids. In particular embodiments, the CPPs disclosed herein comprise about 6 to about 10 amino acids, or about 6 to about 8 amino acids.

Each amino acid in the cCPP may be a natural or non-natural amino acid, such as a D or L amino acid, or a naturally occurring or synthetic amino acid.

In some embodiments, the cCPP comprises the following sequence: $-AA^1-AA^2-AA^3-AA^4-(AA^5)_m-$, wherein: $AA^1$, $AA^2$, $AA^3$, and $AA^4$ are independently selected from an amino acid, which is optionally substituted with one or more substituents; $AA^5$ at each instance and when present, is independently selected from an amino acid, which is optionally substituted with one or more substituents; m is a number in the range of from 0 to 10 (e.g., 0, 1, 2, 3, 4, 5, 6, 7, 8, 9, and 10, inclusive of all ranges and subranges therebetween).

In particular embodiments, at least two of $AA^1$, $AA^2$, $AA^3$, $AA^4$ and $AA^5$ are arginine. In other particular embodiments, and at least two of $AA^1$, $AA^2$, $AA^3$, $AA^4$ and $AA^5$ are independently a hydrophobic amino acid which is optionally substituted. Thus, in certain embodiments, the cCPPs may include any combination of at least two arginines and at least two hydrophobic amino acids. In other embodiments, the cCPPs may include any combination of two to three arginines and at least two hydrophobic amino acids.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, pipecolic acid, or nicotinoyl lysine, each of which is optionally substituted with one or more substituents. The structures of a few of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents. In particular embodiments, each hydrophobic amino acid is naphthylalanine, pipecolic acid, or 3-(3-benzothienyl)-alanine, each of which is optionally substituted with one or more substituents. In other particular embodiments, any three hydrophobic amino acids are independently naphthylalanine, pipecolic acid, and 3-(3-benzothienyl)-alanine, each of which is optionally substituted with one or more substituents. In other particular embodiments, any two hydrophobic amino acids are pipecolic acid and 3-(3-benzothienyl)-alanine, each of which is optionally substituted with one or more substituents. For example, in some embodiments, $AA^4$ is 3-(3-benzothienyl)-alanine; and, in some embodiments, m is 1 and $AA^5$ is pipecolic acid.

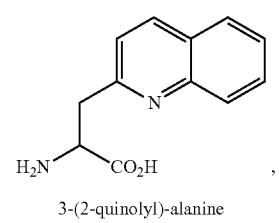

3-(2-quinolyl)-alanine

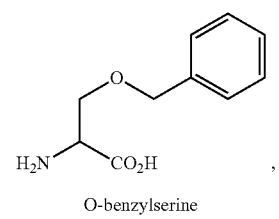

O-benzylserine

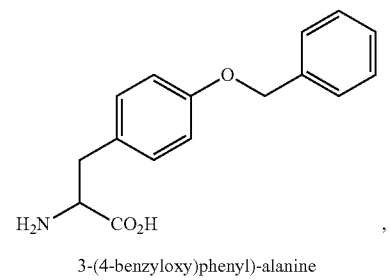

3-(4-benzyloxy)phenyl)-alanine

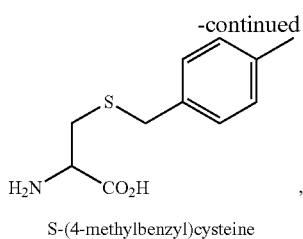

S-(4-methylbenzyl)cysteine

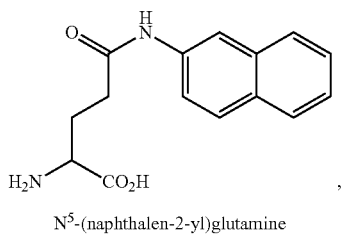

N⁵-(naphthalen-2-yl)glutamine

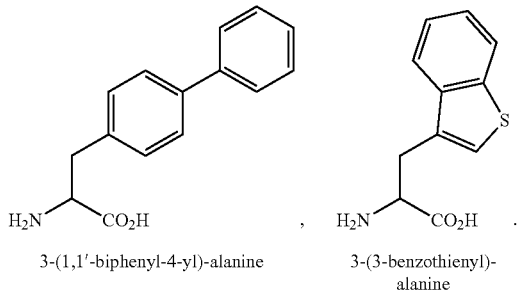

3-(1,1'-biphenyl-4-yl)-alanine    3-(3-benzothienyl)-alanine

The optional substituent can be any atom or group which does not significantly reduce the cytosolic delivery efficiency of the cCPP, e.g., compared to an otherwise identical cCCP which does not include the optional substituent. In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a cCPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the cCPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the cCPPs described herein comprise at least two consecutive hydrophobic amino acids and at least two consecutive arginines. In further embodiments, one hydrophobic amino acid is adjacent to one of the arginines. In still other embodiments, the cCPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the cCPPs described herein (e.g., $AA^1$, $AA^2$, $AA^3$, $AA^4$ and $AA^5$ at each instance and when present) can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid.

Each of $AA_{H1}$ and $AA_{H2}$ are independently selected from any hydrophobic amino acid, e.g., glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, tert-leucine, or nicotinoyl lysine, each of which is optionally substituted with one or more substituents. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents. In particular embodiments, the hydrophobic amino acid is naphthylalanine or 3-(3-benzothienyl)-alanine, each of which is optionally substituted with one or more substituents. In other particular embodiments, any two hydrophobic amino acids are naphthylalanine and 3-(3-benzothienyl)-alanine, each of which is optionally substituted with one or more substituents.

In some embodiments, each of the hydrophobic amino acids in the peptides disclosed herein (e.g., $AA_{H1}$ and $AA_{H2}$) are independently a hydrophobic amino acid having a hydrophobicity value which is greater than that of glycine. In other embodiments, each of the hydrophobic amino acids in the peptides disclosed herein (e.g., $AA_{H1}$ and $AA_{H2}$) are independently a hydrophobic amino acid having a hydrophobicity value which is greater than that of alanine. In still other embodiments, each of the hydrophobic amino acids in the peptides disclosed herein (e.g., $AA_{H1}$ and $AA_{H2}$) are independently an hydrophobic amino acid having a hydrophobicity value which is greater than that of phenylalanine, e.g., as measured using the hydrophobicity scales described above, including Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also been found to improve the cytosolic uptake of the cCPP (and the attached cargo). For example, in some embodiments, the cCPPs disclosed herein may include $AA_{H1}$-D-Arg or D-Arg-$AA_{H1}$. In other embodiments, the cCPPs disclosed herein may include $AA_{H1}$-L-Arg or L-Arg-$AA_{H1}$.

The size of the hydrophobic amino acid on the N- or C-terminal of the D-Arg or an L-Arg, or a combination thereof (e.g., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 $Å^2$, at least about 210 $Å^2$, at least about 220 $Å^2$, at least about 240 $Å^2$, at least about 250 $Å^2$, at least about 260 $Å^2$, at least about 270 $Å^2$, at least about 280 $Å^2$, at least about 290 $Å^2$, at least about 300 $Å^2$, at least about 310 $Å^2$, at least about 320 $Å^2$, or at least about 330 $Å^2$. In some embodiments, $AA_{H2}$ has a side chain side with a SASA of at least about 200 $Å^2$, at least about 210 $Å^2$, at least about 220 $Å^2$, at least about 240 $Å^2$, at least about 250 $Å^2$, at least about 260 Å², at least about 270 Å², at least about 280 Å², at least about 290 Å², at least about 300 Å², at least about 310 Å², at least about 320 Å², or at least about 330 Å². In some embodiments, the side chains of $AA_{H1}$ and $AA_{H2}$ have a combined SASA of at least about 350 Å², at least about 360 Å², at least about 370 Å², at least about 380 A2, at least about 390 Å², at least about 400 Å², at least about 410 Å², at least about 420 Å², at least about 430 Å², at least about 440 Å², at least about 450 Å², at least about 460 Å², at least about 470 Å², at least about 480 Å², at least about 490 Å², greater than about 500 Å², at least about 510 Å², at least about 520 Å², at least about 530 Å², at least about 540 Å², at least about 550 Å², at least about 560 Å², at least about 570 Å², at least about 580 Å², at least about 590 Å², at least about 600 Å², at least about 610 Å², at least about 620 Å², at least about 630 Å², at least about 640 Å², greater than about 650 Å², at least about 660 Å², at least about 670 Å², at least about 680 Å², at least about 690 Å², or at least about 700 Å². In some embodiments, $AA_{H2}$ is a hydrophobic amino acid with a side chain having a SASA that is less than or equal to the SASA of the hydrophobic side chain of $AA_{H1}$. By way of example, and not by limitation, a cCPP having a Nal-Arg motif exhibits improved cytosolic delivery efficiency compared to an otherwise identical CPP having a Phe-Arg motif; a cCPP having a Phe-Nal-Arg motif exhibits improved cytosolic delivery efficiency compared to an otherwise identical cCPP having a Nal-Phe-Arg motif; and a phe-Nal-Arg motif exhibits improved cytosolic delivery efficiency compared to an otherwise identical cCPP having a nal-Phe-Arg motif.

As used herein, "hydrophobic surface area" or "SASA" refers to the surface area (reported as square Ångstroms; Å²) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635. https://doi.org/10.1371/journal.pone.0080635, which is herein incorporated by reference in its entirety for all purposes.

TABLE 3

| Residue | Theoretical | Empirical | Miller et al. (1987) | Rose et al. (1985) |
| --- | --- | --- | --- | --- |
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |

TABLE 3-continued

| Residue | Theoretical | Empirical | Miller et al. (1987) | Rose et al. (1985) |
| --- | --- | --- | --- | --- |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the cCPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the cCPP does not include a hydrophobic amino acid having a side chain which is larger (as described herein) than at least one of $AA_{H1}$ or $AA_{H1}$. In further embodiments, the cCPP does not include a hydrophobic amino acid with a side chain having a surface area greater than $AA_{H1}$. For example, in embodiments in which at least one of $AA_{H1}$ or $AA_{H2}$ is phenylalanine, the cCPP does not further include a naphthylalanine (although the cCPP include at least one hydrophobic amino acid which is smaller than $AA_{H1}$ and $AA_{H1}$, e.g., leucine). In still other embodiments, the cCPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the cCPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the cCPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_H$ can be D-nal, D-trp, or D-phe. In another non-limiting example, when arginine is L-Arg, $AA_H$ can be L-Nal, L-Trp, or L-Phe.

In some embodiments, the cCPPs described herein include three arginines. Accordingly, in some embodiments, the cCPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R-R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the cCPPS have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AA_{H1}$ and $AA_{H2}$ can be selected to improve cytosolic uptake efficiency, e.g., as described above, where $AA_{H1}$ has the same chirality as the adjacent arginine, and $AA_{H1}$ and $AA_{H2}$ have the opposite chirality.

In some embodiments, the cCPPs described herein include three hydrophobic amino acids. Accordingly, in some embodiments, the cCPPs described herein include one of the following sequences: $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any hydrophobic amino acid described above, e.g., piperidine-2-carboxylic acid (also referred to herein as pipecolic acid), naphthylalanine, 3-(3-benzothienyl)-alanine, tryptophan, or phenylalanine. In particular embodiments, $AA_{H3}$ piperidine-2-carboxylic acid (aka pipecolic acid). In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the cCPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-$AA_{H1}$ and L-$AA_{H2}$ is L-Nal. In other particular embodiments, L-$AA_{H1}$ is L-Nal.

As discussed above, the disclosure provides for various modifications to a cyclic peptide sequence which improves cytosolic delivery efficiency. In some embodiments, improved cytosolic uptake efficiency can be measured by comparing the cytosolic delivery efficiency of the CPP having the modified sequence to a proper control sequence. In some embodiments, the control sequence does not include a particular modification (e.g., matching chirality of R and $AA_{H1}$) but is otherwise identical to the modified sequence. In other embodiments, the control has the following sequence: cyclic(fΦRrRrQ) (also referred to as cCPP9).

As used herein cytosolic delivery efficiency refers to the ability of a peptide (e.g., cCPP conjugated to a CAL PDZ binding sequence) to traverse a cell membrane and enter the cytosol. In embodiments, cytosolic delivery efficiency of the peptide is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a peptide over the concentration of the peptide in the growth medium. Relative cytosolic delivery efficiency refers to the concentration of a peptide in the cytosol compared to the concentration of a control peptide in the cytosol. Quantification can be achieved by fluorescently labeling the peptide (e.g., with a FITC dye) and measuring the fluorescence intensity using techniques well-known in the art.

In particular embodiments, relative cytosolic delivery efficiency is determined by comparing (i) the amount of a peptide of the invention internalized by a cell type (e.g., HeLa cells) to (ii) the amount of the control peptide internalized by the same cell type. To measure relative cytosolic delivery efficiency, the cell type may be incubated in the presence of a peptide of the invention for a specified period of time (e.g., 30 minutes, 1 hour, 2 hours, etc.) after which the amount of the peptide internalized by the cell is quantified using methods known in the art, e.g., fluorescence microscopy. Separately, the same concentration of the control peptide is incubated in the presence of the cell type over the same period of time, and the amount of the control peptide internalized by the cell is quantified.

In other embodiments, relative cytosolic delivery efficiency can be determined by measuring the $IC_{50}$ of a peptide having a modified sequence for an intracellular target, and comparing the $IC_{50}$ of said peptide to a proper control sequence (as described herein, e.g., cCPP9).

In some embodiments, the relative cytosolic delivery efficiency of the cCPPs described herein in the range of from about 1% to about 700% compared to cyclo(fΦRrRrQ), e.g., about 5%, about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, or about 590%, about 600%, about 610%, about 620%, about 630%, about 640%, about 650%, about 660%, about 670%, about 680%, or about 690%, inclusive of all values and subranges therebetween.

In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

Non-limiting examples of suitable cell penetrating peptide sequences which can be incorporated into a cyclic CPPs of the disclosure are provided in Table 4.

TABLE 4

Examples of cells penetrating peptide s.

| ID | CPP Sequence |
| --- | --- |
| PCT 1 | FΦRRR (SEQ ID NO: 2) |
| PCT 2 | FΦRRRR (SEQ ID NO: 3) |
| PCT 3 | FΦRRRR (SEQ ID NO: 4) |
| PCT 4 | RRRΦF (SEQ ID NO: 5) |
| PCT 5 | RRRRΦF (SEQ ID NO: 6) |
| PCT 6 | FΦRRRRR (SEQ ID NO: 7) |
| PCT 7 | FφRrR (SEQ ID NO: 8) |
| PCT 8 | FφRrR (SEQ ID NO: 9) |
| PCT 9 | FΦRRRR (SEQ ID NO: 10) |
| PCT 10 | fΦRrRr (SEQ ID NO: 11) |
| PCT 11 | RRFRΦR (SEQ ID NO: 12) |
| PCT 12 | FRRRRΦ (SEQ ID NO: 13) |
| PCT 13 | rRFRΦR (SEQ ID NO: 14) |
| PCT 14 | RRΦFRR (SEQ ID NO: 15) |
| PCT 15 | CRRRRFW (SEQ ID NO: 16) |
| PCT 16 | FfΦRrRr (SEQ ID NO: 17) |
| PCT 17 | FFΦRRRR (SEQ ID NO: 18) |
| PCT 18 | RFRFRΦR (SEQ ID NO: 19) |
| PCT 19 | cyclo (URRRRFW) |
| PCT 20 | CRRRRFW (SEQ ID NO: 20) |
| PCT 21 | FΦRRRRQK (SEQ ID NO: 21) |
| PCT 22 | FΦRRRRQC (SEQ ID NO: 22) |
| PCT 23 | FΦRrRr (SEQ ID NO: 23) |
| PCT 24 | FΦRRRRR (SEQ ID NO: 24) |
| PCT 25 | RRRRΦFDΩC (SEQ ID NO: 25) |
| PCT 26 | FΦRRR (SEQ ID NO: 26) |
| PCT 27 | FWRRR (SEQ ID NO: 27) |
| PCT 28 | RRRΦF (SEQ ID NO: 28) |

TABLE 4-continued

Examples of cells penetrating peptides.

| ID | CPP Sequence |
|---|---|
| PCT 29 | RRRWF (SEQ ID NO: 29) |
| SAR 1 | FΦRRRR (SEQ ID NO: 30) |
| SAR 19 | FFRRR (SEQ ID NO: 31) |
| SAR 20 | FFrRr (SEQ ID NO: 32) |
| SAR 21 | FFRrR (SEQ ID NO: 33) |
| SAR 22 | FRFRR (SEQ ID NO: 34) |
| SAR 23 | FRRFR (SEQ ID NO: 35) |
| SAR 24 | FRRRF (SEQ ID NO: 36) |
| SAR 25 | GΦRRR (SEQ ID NO: 37) |
| SAR 26 | FFFRA (SEQ ID NO: 38) |
| SAR 27 | FFFRR (SEQ ID NO: 39) |
| SAR 28 | FFRRRR (SEQ ID NO: 40) |
| SAR 29 | FRRFRR (SEQ ID NO: 41) |
| SAR 30 | FRRRFR (SEQ ID NO: 42) |
| SAR 31 | RFFRRR (SEQ ID NO: 43) |
| SAR 32 | RFRRFR (SEQ ID NO: 44) |
| SAR 33 | FRFRRR (SEQ ID NO: 45) |
| SAR 34 | FFFRRR (SEQ ID NO: 46) |
| SAR 35 | FFRRRF (SEQ ID NO: 47) |
| SAR 36 | FRFFRR (SEQ ID NO: 48) |
| SAR 37 | RRFFRR (SEQ ID NO: 49) |
| SAR 38 | FFRFRR (SEQ ID NO: 50) |
| SAR 39 | FFRRFR (SEQ ID NO: 51) |
| SAR 40 | FRRFFR (SEQ ID NO: 52) |
| SAR 41 | FRRFRF (SEQ ID NO: 53) |
| SAR 42 | FRFRFR (SEQ ID NO: 54) |
| SAR 43 | RFFRFR (SEQ ID NO: 55) |
| SAR 44 | GΦRRRR (SEQ ID NO: 56) |
| SAR 45 | FFFRRRR (SEQ ID NO: 57) |
| SAR 46 | RFFRRRR (SEQ ID NO: 58) |
| SAR 47 | RRFFRRR (SEQ ID NO: 59) |
| SAR 48 | RFFFRRR (SEQ ID NO: 60) |
| SAR 49 | RRFFFRR (SEQ ID NO: 61) |
| SAR 50 | FFRRFRR (SEQ ID NO: 62) |
| SAR 51 | FFRRRRF (SEQ ID NO: 63) |
| SAR 52 | FRRFFRR (SEQ ID NO: 64) |
| SAR 53 | FFFRRRRR (SEQ ID NO: 65) |
| SAR 54 | FFFRRRRRR (SEQ ID NO: 66) |
| SAR 55 | FΦRrRr (SEQ ID NO: 67) |
| SAR 56 | XXRRRR (SEQ ID NO: 68) |
| SAR 57 | FfFRrR (SEQ ID NO: 69) |
| SAR 58 | fFfRrR (SEQ ID NO: 70) |
| SAR 59 | fFfRrR (SEQ ID NO: 71) |
| SAR 60 | FfFrRr (SEQ ID NO: 72) |
| SAR 61 | fFφRr (SEQ ID NO: 73) |
| SAR 62 | fΦfrRr (SEQ ID NO: 74) |
| SAR 63 | φFfrRr (SEQ ID NO: 75) |
| SAR 64 | FΦrRr (SEQ ID NO: 76) |
| SAR 65 | fΦrRr (SEQ ID NO: 77) |
| SAR 66 | Ac-(Lys-fFRrRrD) (SEQ ID NO: 78, underlined portion) |
| SAR 67 | Ac-(Dap-fFRrRrD) (SEQ ID NO: 79, underlined portion) |
| SAR 68 | CWWRRRRC (disulfide cyclized) |
| SAR 69 | CWWWRRRRC (disulfide cyclized) |
| SAR 70 | CFWRRRRC (disulfide cyclized) |
| SAR 71 | CWWWRRRRC (disulfide cyclized) |
| Pin1 15 | Pip-Nal-Arg-Glu-arg-arg (SEQ ID NO: 80) |
| Pin1 16 | Pip-Nal-Arg-Arg-arg-arg (SEQ ID NO: 81) |
| Pin1 17 | Pip-Nal-Arg-arg-arg-arg (SEQ ID NO: 82) |
| Pin1 18 | Pip-Nal-Arg-arg-arg-arg (SEQ ID NO: 83) |
| Pin1 19 | Pip-Nal-Phe-Arg-arg-arg (SEQ ID NO: 84) |
| Pin1 20 | Pip-Nal-Phe-Arg-arg-arg (SEQ ID NO: 85) |
| Pin1 21 | Pip-Nal-phe-Arg-arg-arg (SEQ ID NO: 86) |
| Pin1 22 | Pip-Nal-phe-Arg-arg-arg-(SEQ ID NO: 87) |
| Pin1 23 | Pip-Nal-nal-Arg-arg-arg-(SEQ ID NO: 156) |
| Pin1 24 | Pip-Nal-nal-Arg-arg-arg (SEQ ID NO: 157) |
| Rev-13 | [Pim-RQRR-Nlys]GRRR[b] |
| hLF | KCFQWQRNMRKVRGPPVSC (disulfide cyclized) |
| cTat | [KrRrGrKkRrE][c] |
| cR10 | [KrRrRrRrRrRE][c] |
| L-50 | [RVRTRGKRRIRRpP] (SEQ ID NO: 88) |
| L-51 | [RTRTRGKRRIRVpP] (SEQ ID NO: 89) |
| [WR]4 | [WRWRWRWR] (SEQ ID NO: 90) |
| MCoTI-II | [GGVCPKILKKCRRDSDCPGACICRGNGYCGSGSD] (multiply cyclized) |
| Rotstein et al. Chem. Eur. J. 2011 | [P-Cha-r-Cha-r-Cha-r-Cha-r-G][d] |
| Lian et al. J. Am. Chem. Soc. 2014 | Tm(SvP-F2Pmp-H)-Dap-(FΦRRRR-Dap)[f] |
| Lian et al. J. Am. Chem. Soc. 2014 | [Tm(a-Sar-D-pThr-Pip-ΦRAa)-Dap-(FΦRRRR-Dap)[f] |
| IA8b | [CRRSRRGCGRRSRRCG][g] |
| Dod-[R5] | [K(Dod)RRRR] (SEQ ID NO: 91) |
| LK-3 | LKKLCKLLKKLCKLAG / LKKLCKLLKKLCKLAG |
| | RRRR-[KRRRE][c] |
| | RRR-[KRRRRE][c] |
| | RR-[KRRRRRE][c] |
| | R-[KRRRRRRE][c] |
| [CR]4 | [CRCRCRCR] (SEQ ID NO: 92) |
| cyc3 | [Pra-LRKRLRKFRN-AzK][h] |
| PMB | T-Dap-[Dap-Dap-f-L-Dap-Dap-T] (SEQ ID NO: 93) |
| GPMB | T-Agp-[Agp-Agp-f-L-Agp-Agp-T] (SEQ ID NO: 94) |
| cCPP1 | FΦRRRR (SEQ ID NO: 95) |
| cCPP12 | FΦRrRr (SEQ ID NO: 96) |
| cCPP9 | fΦRrRr (SEQ ID NO: 97) |
| cCPP11 | fΦRrRrR (SEQ ID NO: 98) |
| cCPP18 | FΦrRrR (SEQ ID NO: 99) |
| cCPP13 | FΦRRRR (SEQ ID NO: 100) |
| cCPP6 | FΦRRRRR (SEQ ID NO: 101) |
| cCPP3 | RRFRΦR (SEQ ID NO: 102) |
| cCPP7 | FFΦRRRR (SEQ ID NO: 103) |
| cCPP8 | RFRFRΦR (SEQ ID NO: 104) |
| cCPP5 | FΦRRR (SEQ ID NO: 105) |
| cCPP4 | FRRRRΦ (SEQ ID NO: 106) |
| cCPP10 | rRFRΦR (SEQ ID NO: 107) |
| cCPP2 | RRΦFRR (SEQ ID NO: 108) |

Φ, L-2-naphthylalanine; Pim, pimelic acid; Nlys, lysine peptoid residue; D-pThr, D-phosphothreonine; Pip, L-piperidine-2-carboxylic acid; Cha, L-3-cyclohexyl-alanine; Tm, trimesic acid; Dap, L-2,3-diaminopropionic acid; Sar, sarcosine; F2Pmp, L-difluorophosphonomethyl phenylalanine; Dod, dodecanoyl; Pra, L-propargylglycine; AzK, L-6-Azido-2-amino-hexanoic; Agp, L-2-amino-3-guanidinyl-propionic acid; [b]Cyclization between Pim and Nlys; [c]Cyclization between Lys and Glu; [d]Macrocyclization by multicomponent reaction with aziridine aldehyde and isocyanide; [e]Cyclization between the main-chain of Gln residue; [f]N-terminal amine and side chains of two Dap residues bicyclized with Tm; [g]Three Cys side chains bicyclized with tris(bromomethyl)benzene; [h]Cyclization by the click reaction between Pra and Azk.

Additionally, the cCPP used in the polypeptide conjugates and methods described herein can include any sequence disclosed in: U.S. application Ser. No. 15/312,878; U.S. application Ser. No. 15/360,719; International PCT Application No. PCT/US2017/060881 (including the corresponding U.S. Publication); and International Application Publication No. WO 2018/098231 (including the corresponding U.S. Publication), each of which is incorporated by reference in its entirety for all purposes.

CAL PDZ Binding Sequence

As discussed above, the peptide disclosed herein comprise a CAL PDZ binding sequence. Any sequence of amino acids (which may be optionally substituted with one or more a non-peptidyl moieties) which binds (covalently or non-covalently) to the CAL PDZ binding domain may be used with the peptides disclosed herein. In some embodiments, the CAL PDZ binding sequence can be peptide sequence consisting of a few amino acids (e.g., 3 amino acids), a protein fragment, or a protein. Non-limiting examples of suitable CAL PDZ binding sequences are provided in Roberts et al., PLoS Computational Biology, 8(4), 2002, e1002477.

In some embodiments, the CAL PDZ binding sequence is represented by -$AA^6$-$AA^7$-$AA^8$-$(AA^9)_n$, wherein n may be any number in the range of from 0 to 2000 (e.g., any number of amino acid residues as defined above). In some embodiments, at least one of $AA^6$, $AA^7$, $AA^8$, and $AA^9$ at each instance and when present, is independently selected from a hydrophobic amino acid. In some embodiments, the at least one hydrophobic amino acid is independently selected from tert-butyl-glycine, valine, leucine, isoleucine, methyl-leucine, phenylalanine, tryptophan, proline, naphthylalanine, phenylglycine, homophenylalanine, tyrosine, cyclohexylalanine, norleucine, 3-(3-benzothienyl)-alanine, triflouroacetyl-lysine, or nicotinoyl lysine, each of which is optionally substituted with one or more substituents. In some embodiments, the at least one hydrophobic amino acid is tert-butyl-glycine.

In some embodiments, at least one of $AA^6$, $AA^7$, $AA^8$, and $AA^9$ at each instance and when present, is arginine or homoarginine. In some embodiments, any three of $AA^6$, $AA^7$, $AA^8$, and $AA^9$ at each instance and when present, are independently selected from threonine, serine, tert-butyl-glycine, valine, leucine, isoleucine, lysine, and arginine. In some embodiments, at three of $AA^6$, $AA^7$, $AA^8$, and $AA^9$ at each instance and when present, are each independently, threonine, tert-butyl-glycine, and arginine. In some embodiments, $AA^6$ is threonine, $AA^7$ is arginine, and $AA^8$ is tert-butyl-glycine.

Non-limiting examples of CAL PDZ binding sequences for use in the peptides disclosed herein are provided in Table 5.

TABLE 5

| Sequence | Ki (µM) |
|---|---|
| WQVTRV (SEQ ID NO: 109) | 2.3 ± 0.2 |
| WQFTRL (SEQ ID NO: 110) | 7.6 ± 0.7 |
| WQKTRL (SEQ ID NO: 111) | 9.0 ± 0.6 |
| WQRTRL (SEQ ID NO: 112) | 10.8 ± 0.7 |
| WQKTRI (SEQ ID NO: 113) | 12.0 ± 0.9 |
| WQKTRV (SEQ ID NO: 114) | 16 ± 2 |
| WQFTKL (SEQ ID NO: 115) | 16 ± 1 |
| WQRTRI (SEQ ID NO: 116) | 16 ± 2 |

TABLE 5-continued

| Sequence | Ki (µM) |
|---|---|
| WQLTKL (SEQ ID NO: 117) | 17 ± 1 |
| WQKTKL (SEQ ID NO: 118) | 17.8 ± 0.8 |
| WQRTRV (SEQ ID NO: 119) | 18 ± 1 |
| Thr-Arg-Val | ND |
| Thr-Arg-Ile | ND |
| Thr-Arg-Cha | ND |
| Thr-Arg-MeLeu | ND |
| Thr-Arg-Tle | ND |
| Thr-Leu-Tle | ND |
| Thr-Lys(NIC)-Tle | ND |
| Thr-Lys(TFA)-Tle | ND |
| Tle-Thr-Arg-Tle (SEQ ID NO: 120) | ND |

In some embodiments, the CAL PDZ binding sequence independently has a Ki in the range of from about 0.01 µM to about 1000 µM, e.g., about 0.05 µM, about 0.1 µM, about 0.5 µM, about 1 µM, about 5 µM, about 10 µM, about 15 µM, about 20 µM, about 25 µM, about 30 µM, about 35 µM, about 40 µM, about 45 µM, about 50 µM, about 65 µM, about 70 µM, about 75 µM, about 80 µM, about 85 µM, about 90 µM, about 95 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 950 µM, and about 1000 µM, inclusive of all values and subranges therebetween.

Physiologically Cleavable Group

In certain embodiments, the peptides described herein further comprising a physiologically cleavable group. After entering the cell, the physiologically cleavable group is reduced (e.g., enzymatically reduced) to provide a linear peptide, comprising both the cCPP and CAL PDZ binding sequence.

In some embodiments, the cCPP is cyclized through the physiologically cleavable bond. That is, the amino acids at the N and C terminus, respectively, of a precursor (i.e., uncyclized) sequence of a cCPP can be conjugated through a physiologically cleavable bond to thereby form the cCCP. Any group which can be cleaved at physiological conditions and/or by physiological process are suitable for the peptides disclosed herein. In some embodiments, the physiologically cleavable group is a disulfide, carbonate, thiocarbonate, thioester, sulfoxide, hydrazine, or protease-cleavable dipeptide linker. In particular embodiments, the physiologically cleavable group is a disulfide. Without being bond by any particular theory, intracellular GSH reduces of the disulfide bond to generate a linear peptide, comprising both the cCPP and CAL PDZ binding sequence.

In some embodiments, the peptides disclosed herein comprise at least two amino acids form a disulfide bond—$AA^{S1}$ and $AA^{S2}$. In some such embodiments, $AA^{S1}$ is independently an amino acid having a side chain which forms a disulfide bond with AAR. $AA^{S1}$ and $AA^{S2}$ may be the same or different. Thus, in various embodiments, $AA^{S1}$ and $AA^{S2}$ may be independently selected from:

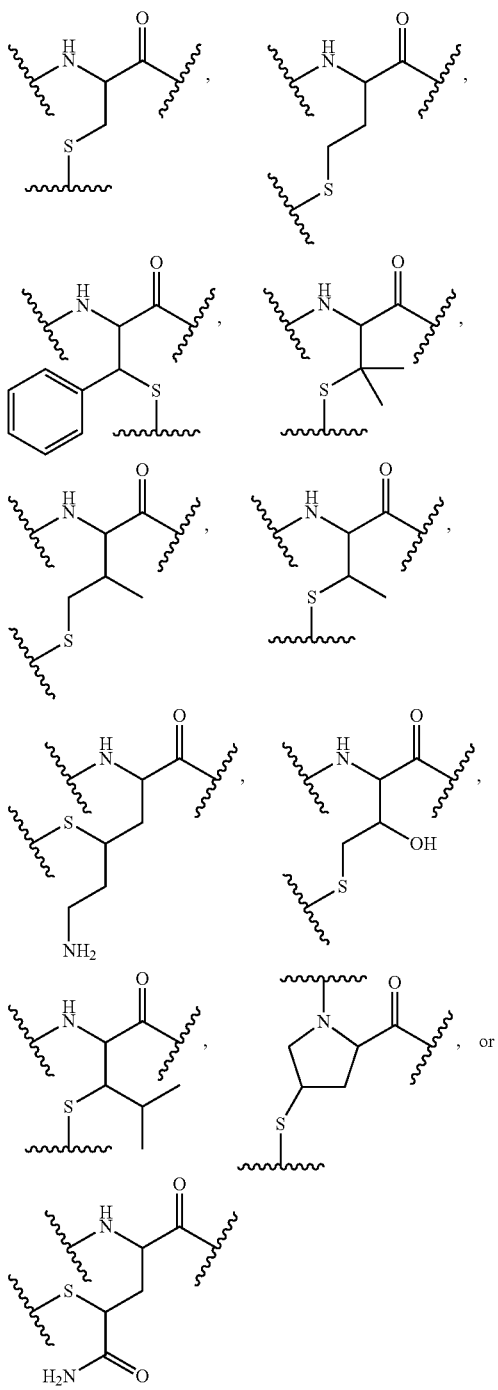

In particular embodiments, wherein at least one of $AA^{S1}$ and $AA^{S2}$ is:

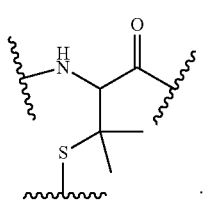 [SMILES: *NC(C(*)=O)C(C)(C)S*]

In other particular embodiments, wherein at least one of $AA^{S1}$ and $AA^{S2}$ is:

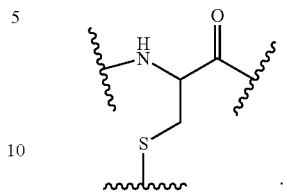

As discussed above, upon entry into the cytosol of a cell, the peptides of the present disclosure generate linear sequences comprising the cell penetrating peptide sequence and the CAL PDZ binding sequence. Thus, after entry into the cytosol, and generation of the linear sequence, the peptides of the disclosure have a structure according to Formula IA or IIA:

$$(AA^{10})_p\text{-}AA^{S1'}\text{-}AA^1\text{-}AA^2\text{-}AA^3\text{-}AA^4\text{-}(AA^5)_m\text{-}AA^{S2'}\text{-}AA^6\text{-}AA^7\text{-}AA^8\text{-}(AA^9)_n \quad \text{(IA), or}$$

$$_n(AA^9)\text{-}AA^8\text{-}AA^7\text{-}AA^6\text{-}AA^{S1'}\text{-}AA^1\text{-}AA^2\text{-}AA^3\text{-}AA^4\text{-}(AA^5)_m\text{-}AA^{S2'}\text{-}(AA^{10})_p \quad \text{(IIA)}$$

Each of $AA^1$, $AA^2$, $AA^3$, $AA^4$, $AA^5$, $AA^6$, $AA^7$, $AA^8$, $AA^9$, and $AA^{10}$, are defined herein above, e.g., independently selected from an amino acid, which is optionally substituted with one or more substituents, wherein at least two of $AA^1$, $AA^2$, $AA^3$, $AA^4$, and $AA^5$ at each instance and when present, are arginine, and at least two of $AA^1$, $AA^2$, $AA^3$, $AA^4$, and $AA^5$ at each instance and when present are independently a hydrophobic amino acid which is optionally substituted.

In some embodiments, any four consecutive amino acids of $AA^1$, $AA^2$, $AA^3$, $AA^4$ and $AA^5$ are selected from the group consisting of: (i) $AA_{H2}$-$AA_{H1}$-R-r; (ii) $AA_{H2}$-$AA_{H1}$-r-R; (iii) R-r-$AA_{H1}$-$AA_{H2}$; and (iv) r-R-$AA_{H1}$-$AA_{H2}$, wherein each of $AA_{H1}$ and $AA_{H2}$ are independently a hydrophobic amino acid. In some embodiments, the hydrophobic amino acid is selected from glycine, alanine, tert-butyl-glycine, valine, leucine, isoleucine, methionine, phenylalanine, tryptophan, proline, naphthylalanine, phenylglycine, homophenylalanine, tyrosine, cyclohexylalanine, norleucine, 3-(3-benzothienyl)-alanine, tert-leucine, pipecolic acid or nicotinoyl lysine, each of which is optionally substituted with one or more substituents. In particular embodiments, any two of $AA^1$, $AA^2$, $AA^3$, $AA^4$, and $AA^5$ are naphthylalanine or 3-(3-benzothienyl)-alanine, each of which is optionally substituted with one or more substituents. In other particular embodiments, any two of $AA^1$, $AA^2$, $AA^3$, $AA^4$, and $AA^5$, at each instance and when present, are pipecolic acid and 3-(3-benzothienyl)-alanine, each of which is optionally substituted with one or more substituents. In still other particular embodiments, any two of $AA^1$, $AA^2$, $AA^3$, $AA^4$, and $AA^5$, at each instance and when present, are arginine, one of $AA^1$, $AA^2$, $AA^3$, $AA^4$, and $AA^5$, at each instance and when present, is 3-(3-benzothienyl)-alanine. In yet still other embodiments, one of $AA^1$, $AA^2$, $AA^3$, $AA^4$, and $AA^5$, at each instance and when present, is pipecolic acid.

Similarly, the values for m, n, and p are defined above. That is, in some embodiments, m is any number which allows for cyclization of the amino acid sequence and still allows for uptake by the cell. In certain embodiments, m is a number in the range of from 0 to 10 (e.g., 0, 1, 2, 3, 4, 5, 6, 7, 8, 9, and 10, inclusive of all values and subranges therebetween). In some embodiments, n is a number in the range of from 0 to 2000 (e.g., 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, 1800, 1850, 1900, 1950, and 2000, inclusive of all values and subranges therebetween). In some embodiments, p is a number in the range of from 0 to 10 (e.g., 0, 1, 2, 3, 4, 5, 6, 7, 8, 9, and 10, inclusive of all values and subranges therebetween).

As discussed above, N and/or C terminus of the peptide disclosed herein may be protected with a suitable non-peptidyl moiety, e.g., those described herein. For example, in Formula IA, when p is 0, the N-terminus of AA' may be H, —C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; in Formula IIA, when p is 0, the C-terminus of $AA^{S2}$ may be OH, $OR^2$, or $NHR^2$, wherein $R^2$ is an alkyl, aryl, or heteroaryl. Similarly, when p is 1 or more, the N or C terminus of AA' may be protected with any suitable non-peptidyl moiety. For example, in Formula IA, when p is a number from 1 to 10, the N-terminus of AA' may be —C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl; in Formula IIA, when p is a number from 1 to 10, the C-terminus of AA' is OH, $OR^2$, or $NHR^2$, wherein $R^2$ is an alkyl, aryl, heteroaryl, or at least one amino acid.

In some embodiments, the CAL PDZ binding sequence is represented by -$AA^6$-$AA^7$-$AA^8$-$(AA^9)_n$, wherein n may be any number in the range of from 0 to 2000 (e.g., any number of amino acid residues as defined above). In some embodiments, at least one of $AA^6$, $AA^7$, $AA^8$, and $AA^9$ at each instance and when present, is independently selected from a hydrophobic amino acid. In some embodiments, the at least one hydrophobic amino acid is independently selected from tert-butyl-glycine, valine, leucine, isoleucine, methyl-leucine, phenylalanine, tryptophan, proline, naphthylalanine, phenylglycine, homophenylalanine, tyrosine, cyclohexylalanine, norleucine, 3-(3-benzothienyl)-alanine, triflouroacetyl-lysine, or nicotinoyl lysine, each of which is optionally substituted with one or more substituents. In some embodiments, the at least one hydrophobic amino acid is tert-butyl-glycine. In some embodiments, at least one of $AA^6$, $AA^7$, $AA^8$, and $AA^9$ at each instance and when present, is arginine. In some embodiments, any three of $AA^6$, $AA^7$, $AA^8$, and $AA^9$ at each instance and when present, are independently selected from threonine, serine, tert-butyl-glycine, valine, leucine, isoleucine, lysine, and arginine. In some embodiments, any three of $AA^6$, $AA^7$, $AA^8$, and $AA^9$ at each instance and when present, are independently selected from threonine, tert-butyl-glycine, and arginine.

As discussed above, in certain embodiments (i.e., prior cyclization, or after reduction of the physiologically cleavable group and generation of a linear peptide), the peptides disclosed herein comprise two amino acids having a side chain comprising a thiol group (referred to herein as $AA^{S1'}$ and $AA^{S2'}$). Thus, in various embodiments, $AA^{S1'}$ and $AA^{S2'}$ may be selected from any of the following amino acids:

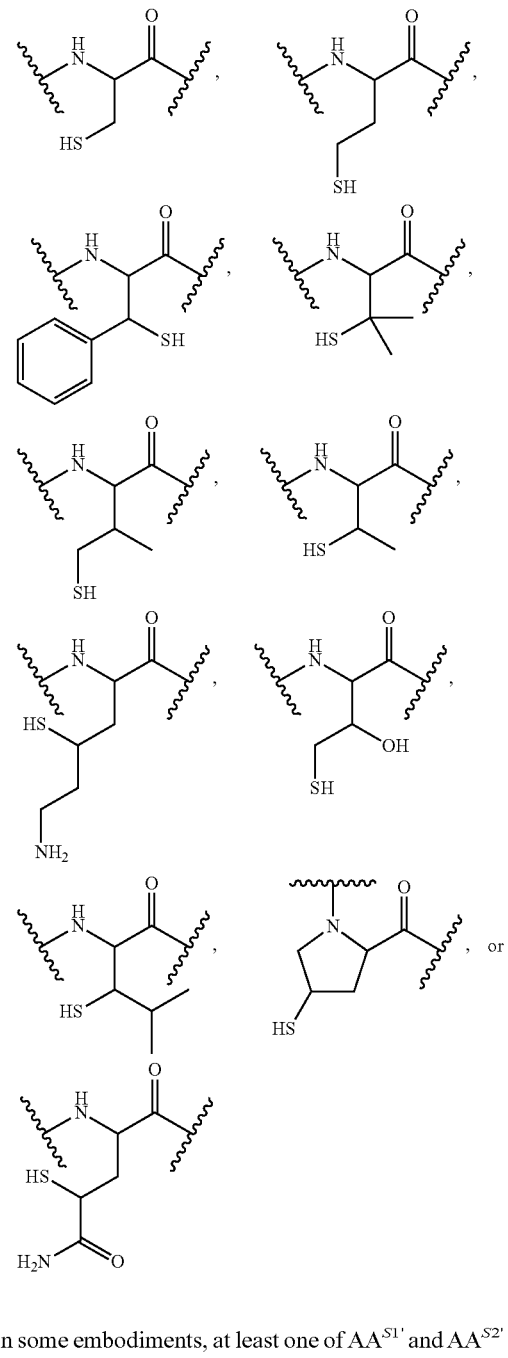

In some embodiments, at least one of $AA^{S1'}$ and $AA^{S2'}$ are:

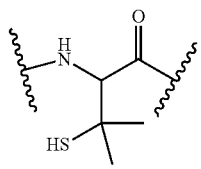

In some embodiments, the peptides of Formula IA is not CRRRRFWQCTRV (SEQ ID NO:1).

Non-limiting examples of the peptides of the disclosure (in the reduced form) are provided in Table 6.
TABLE 6
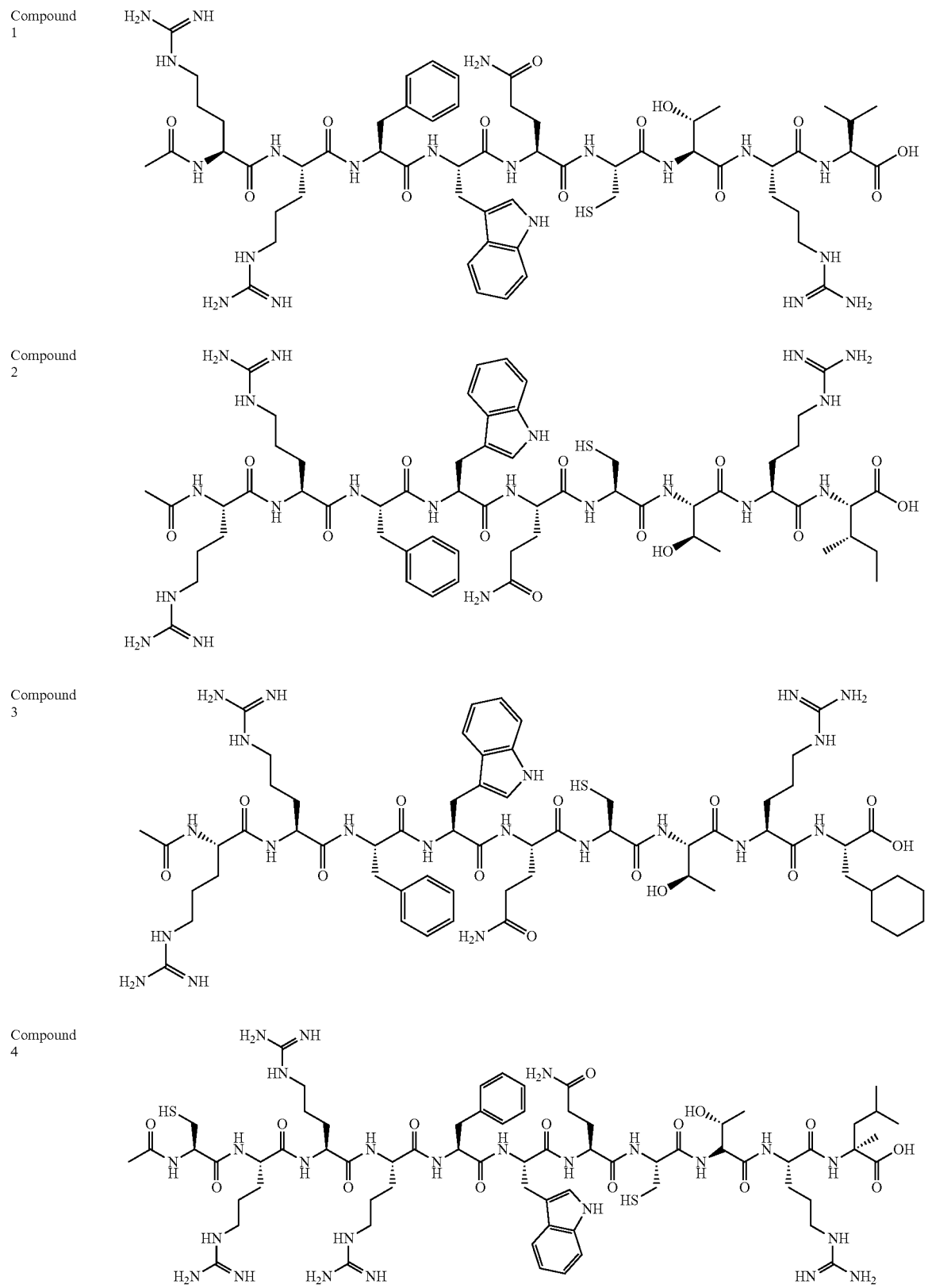

TABLE 6-continued
Compound 5
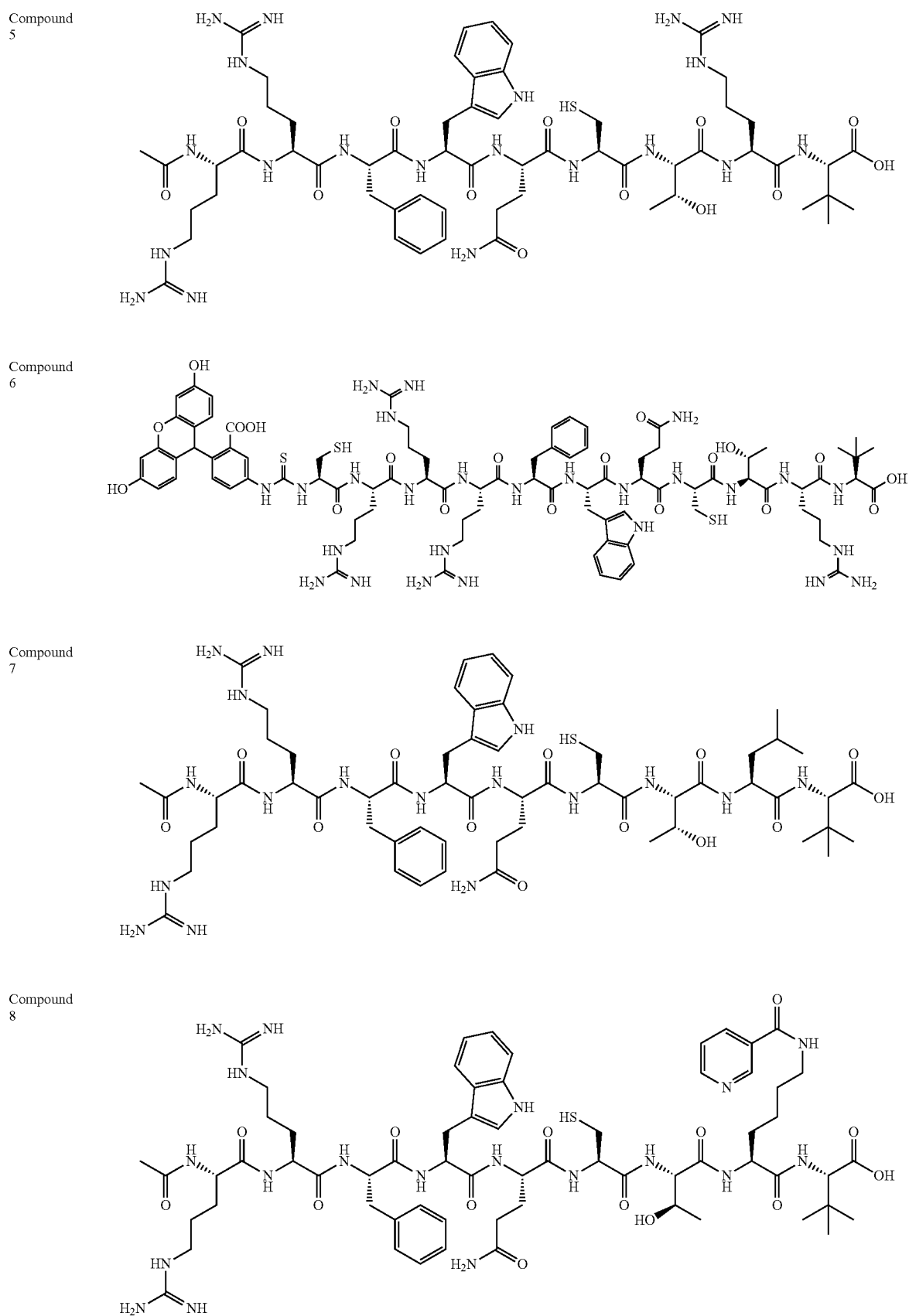
Compound 6
Compound 7
Compound 8

TABLE 6-continued
Compound 9
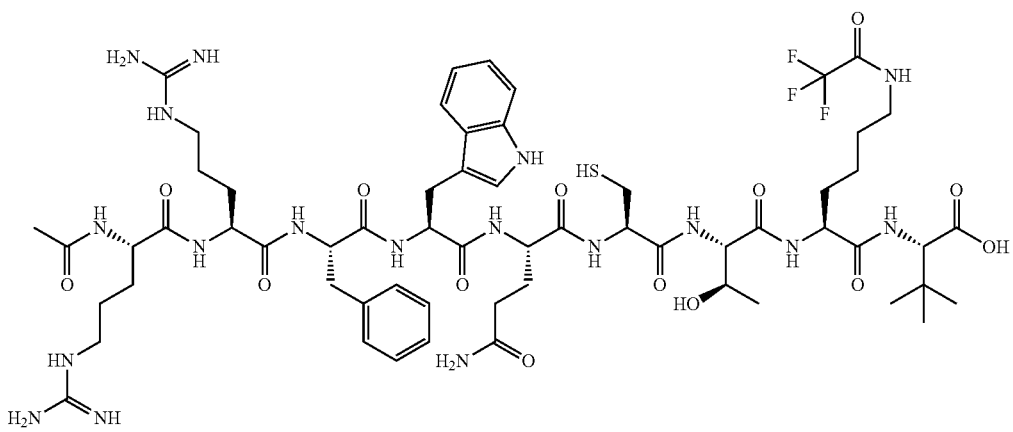 [SMILES: CC(=O)N[C@@H](CCCNC(=N)N)C(=O)N[C@@H](CCCNC(=N)N)C(=O)N[C@@H](Cc1ccccc1)C(=O)N[C@@H](Cc1c[nH]c2ccccc12)C(=O)N[C@@H](CCC(N)=O)C(=O)N[C@@H](CS)C(=O)N[C@H](C(=O)N[C@@H](CCCCNC(=O)C(F)(F)F)C(=O)N[C@H](C(=O)O)C(C)(C)C)[C@@H](C)O]
Compound 10
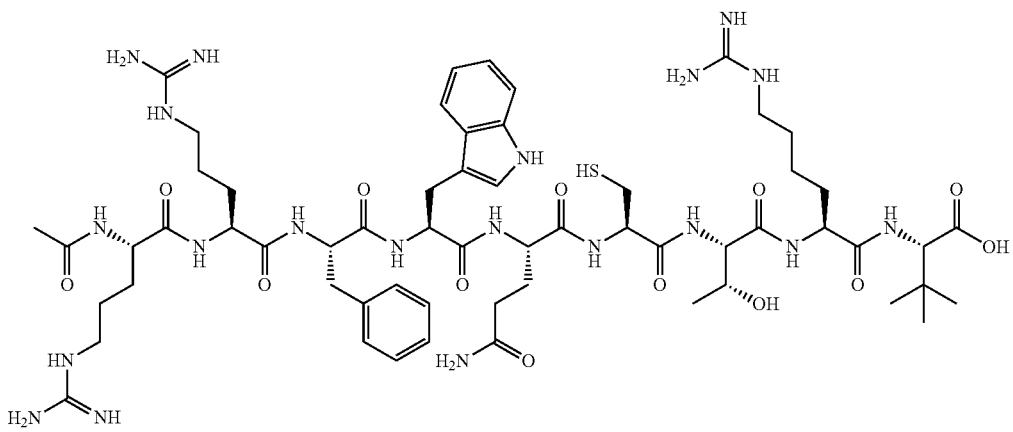 [SMILES: CC(=O)N[C@@H](CCCNC(=N)N)C(=O)N[C@@H](CCCNC(=N)N)C(=O)N[C@@H](Cc1ccccc1)C(=O)N[C@@H](Cc1c[nH]c2ccccc12)C(=O)N[C@@H](CCC(N)=O)C(=O)N[C@@H](CS)C(=O)N[C@H](C(=O)N[C@@H](CCCCNC(=N)N)C(=O)N[C@H](C(=O)O)C(C)(C)C)[C@@H](C)O]
Compound 11
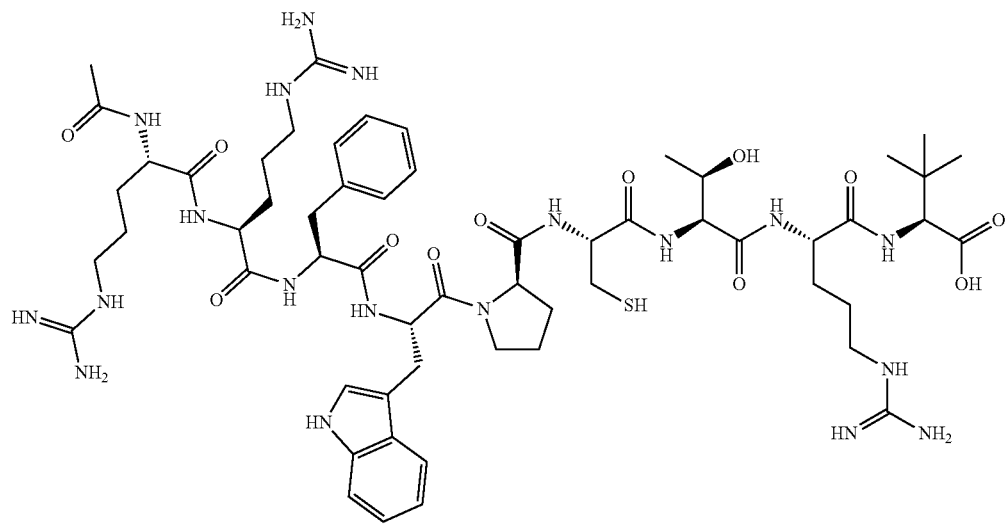 [SMILES: CC(=O)N[C@@H](CCCNC(=N)N)C(=O)N[C@@H](CCCNC(=N)N)C(=O)N[C@@H](Cc1ccccc1)C(=O)N[C@@H](Cc1c[nH]c2ccccc12)C(=O)N1CCC[C@@H]1C(=O)N[C@@H](CS)C(=O)N[C@H](C(=O)N[C@@H](CCCNC(=N)N)C(=O)N[C@H](C(=O)O)C(C)(C)C)[C@@H](C)O]

TABLE 6-continued
Compound 12
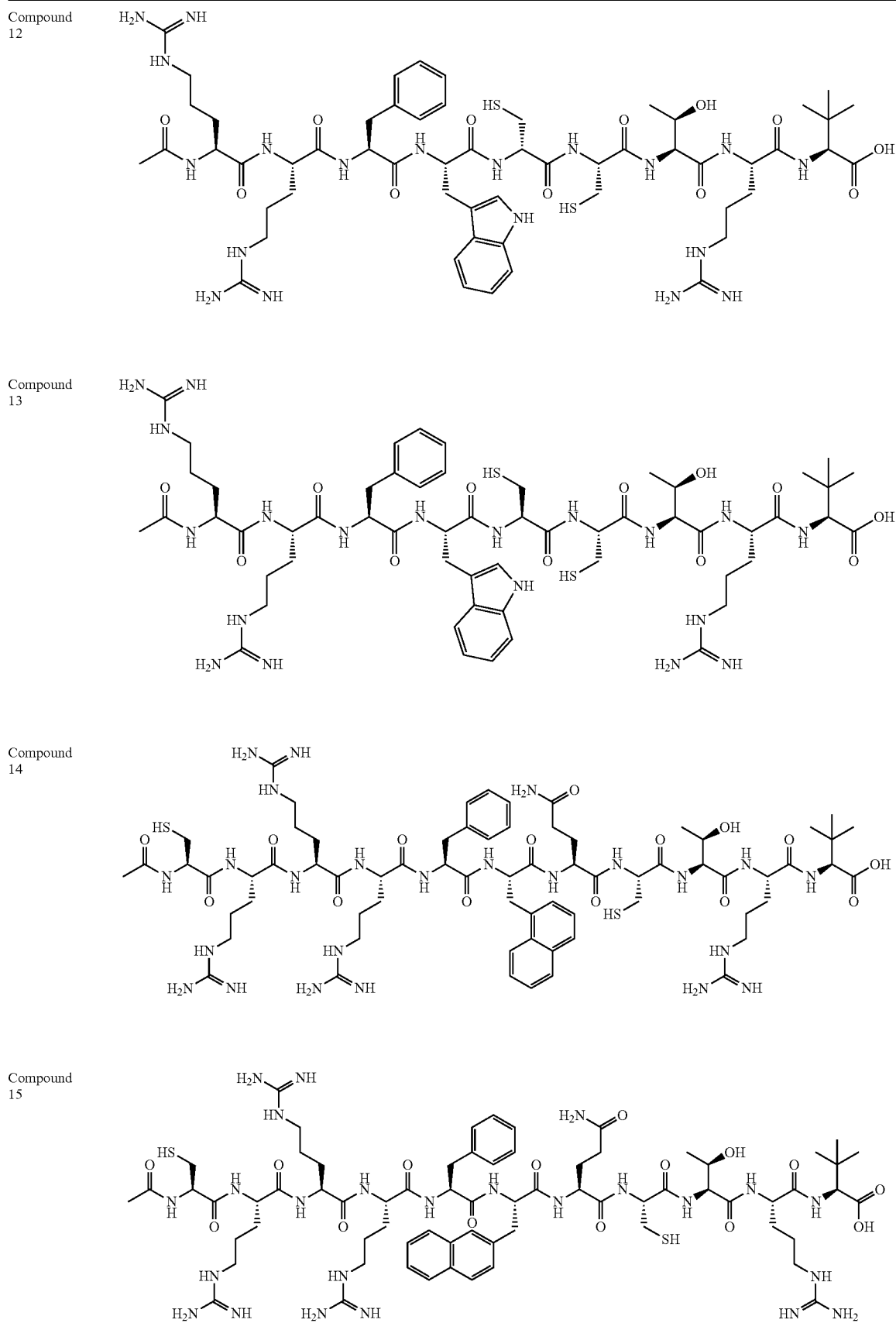
Compound 13
Compound 14
Compound 15

TABLE 6-continued
Compound 16
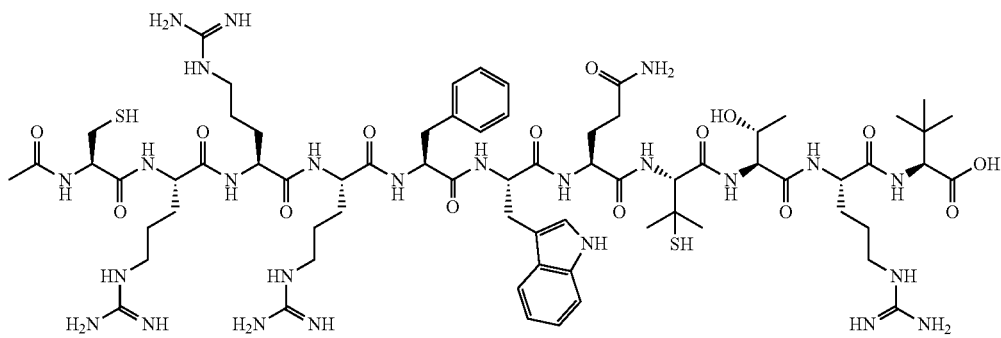 [SMILES: CC(=O)N[C@@H](CS)C(=O)N[C@@H](CCCNC(=N)N)C(=O)N[C@@H](CCCNC(=N)N)C(=O)N[C@@H](CCCNC(=N)N)C(=O)N[C@@H](Cc1ccccc1)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]
Compound 17
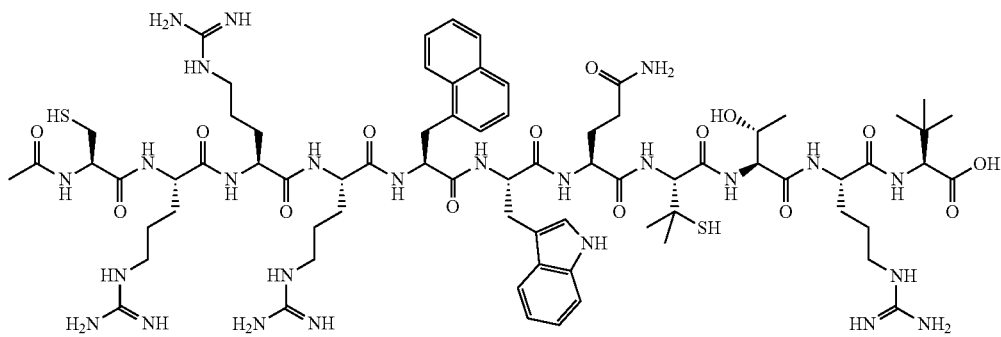 [SMILES: CC(=O)N[C@@H](CS)C(=O)N[C@@H](CCCNC(=N)N)C(=O)N[C@@H](CCCNC(=N)N)C(=O)N[C@@H](CCCNC(=N)N)C(=O)N[C@@H](Cc1cccc2ccccc12)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]
Compound 18
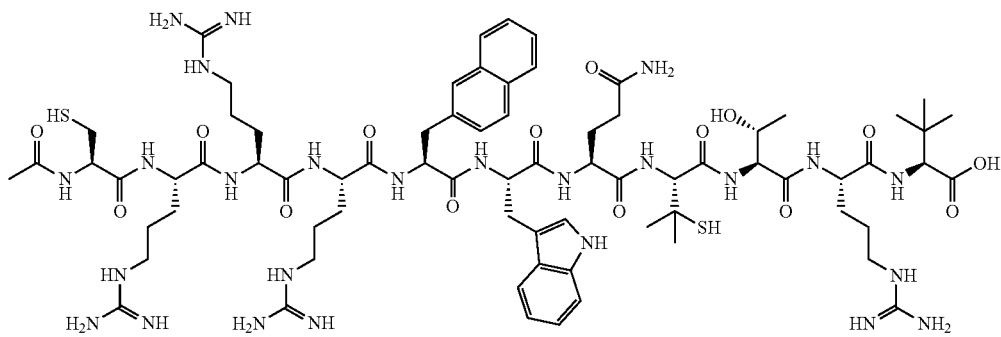 [SMILES: CC(=O)N[C@@H](CS)C(=O)N[C@@H](CCCNC(=N)N)C(=O)N[C@@H](CCCNC(=N)N)C(=O)N[C@@H](CCCNC(=N)N)C(=O)N[C@@H](Cc1ccc2ccccc2c1)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]
Compound 19
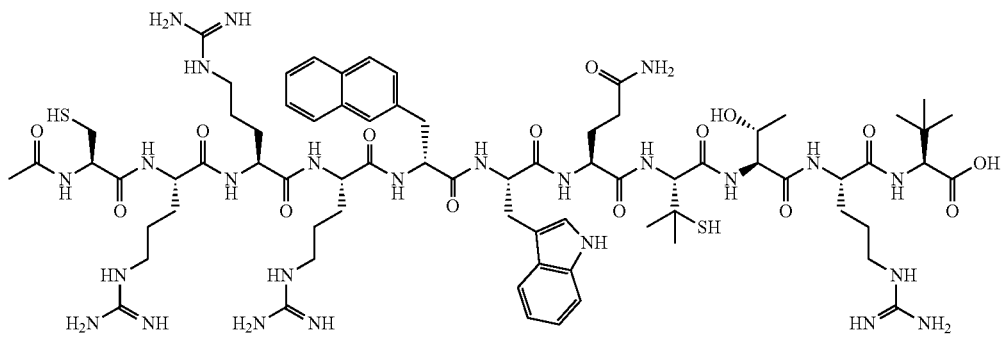 [SMILES: CC(=O)N[C@@H](CS)C(=O)N[C@@H](CCCNC(=N)N)C(=O)N[C@@H](CCCNC(=N)N)C(=O)N[C@@H](CCCNC(=N)N)C(=O)N[C@H](Cc1ccc2ccccc2c1)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]

TABLE 6-continued
Compound 20
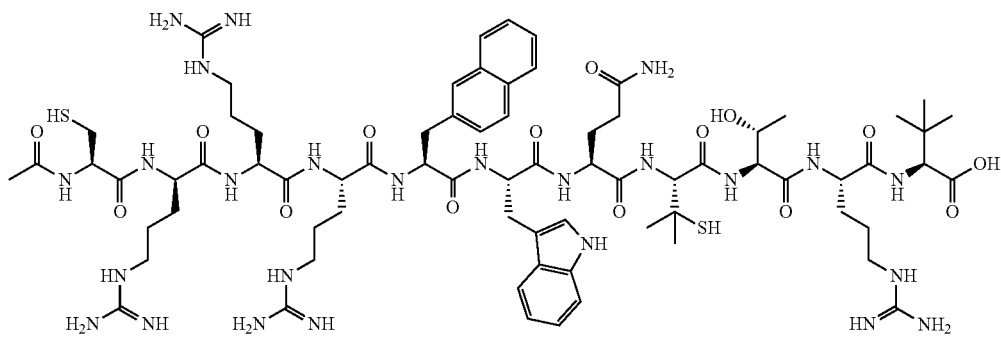 [SMILES: CC(=O)N[C@@H](CS)C(=O)N[C@H](CCCNC(=N)N)C(=O)N[C@@H](CCCNC(=N)N)C(=O)N[C@@H](CCCNC(=N)N)C(=O)N[C@@H](Cc1ccc2ccccc2c1)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]
Compound 21
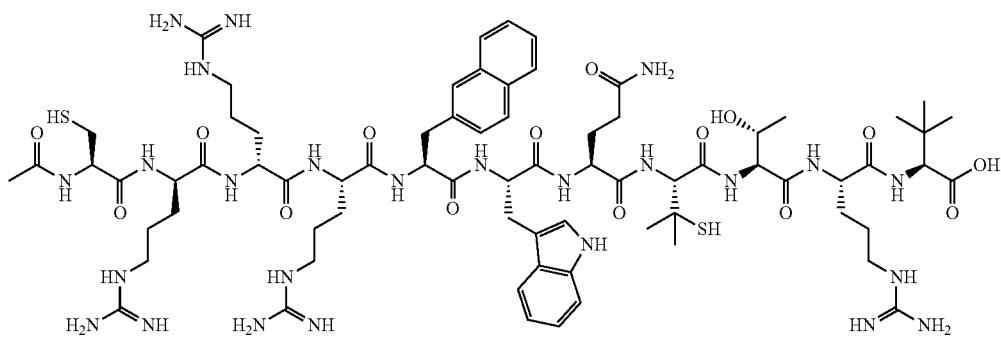 [SMILES: CC(=O)N[C@@H](CS)C(=O)N[C@H](CCCNC(=N)N)C(=O)N[C@H](CCCNC(=N)N)C(=O)N[C@@H](CCCNC(=N)N)C(=O)N[C@@H](Cc1ccc2ccccc2c1)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]
Compound 22
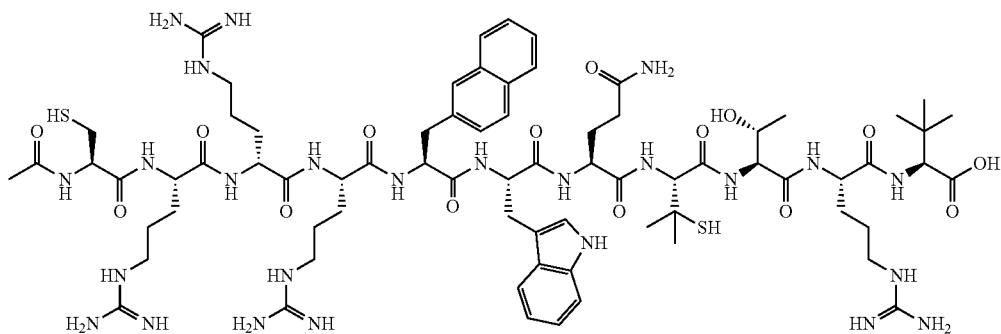 [SMILES: CC(=O)N[C@@H](CS)C(=O)N[C@@H](CCCNC(=N)N)C(=O)N[C@H](CCCNC(=N)N)C(=O)N[C@@H](CCCNC(=N)N)C(=O)N[C@@H](Cc1ccc2ccccc2c1)C(=O)N[C@@H](Cc1c[nH]c2ccccc12)C(=O)N[C@@H](CCC(N)=O)C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]
Compound 23
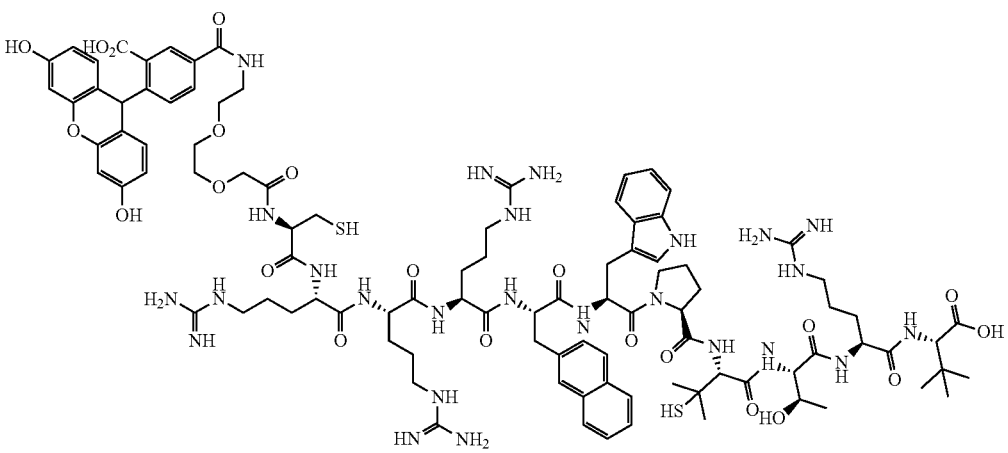 [SMILES: C[C@@H](O)[C@H](NC(=O)[C@@H](NC(=O)[C@@H]1CCCN1C(=O)[C@H](Cc1c[nH]c2ccccc12)NC(=O)[C@H](Cc1ccc2ccccc2c1)NC(=O)[C@H](CCCNC(=N)N)NC(=O)[C@H](CCCNC(=N)N)NC(=O)[C@H](CCCNC(=N)N)NC(=O)[C@H](CS)NC(=O)COCCOCCNC(=O)c1ccc(C2c3ccc(O)cc3Oc3cc(O)ccc32)c(C(=O)O)c1)C(C)(C)S)C(=O)N[C@@H](CCCNC(=N)N)C(=O)N[C@H](C(=O)O)C(C)(C)C]

TABLE 6-continued
Compound 24
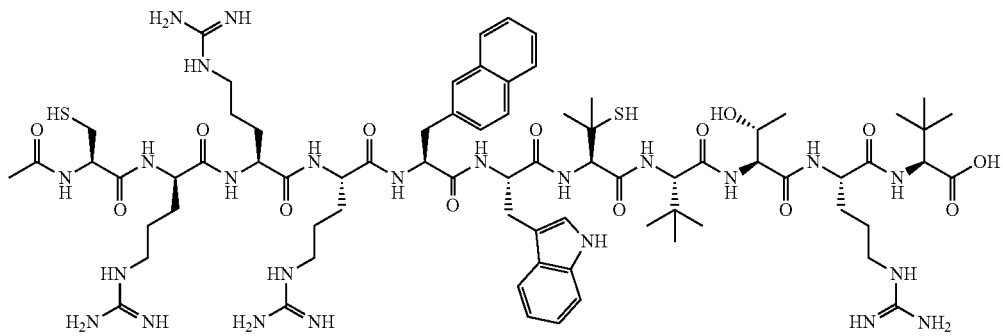 [SMILES: CC(=O)N[C@@H](CS)C(=O)N[C@H](CCCNC(=N)N)C(=O)N[C@@H](CCCNC(=N)N)C(=O)N[C@@H](CCCNC(=N)N)C(=O)N[C@@H](Cc1ccc2ccccc2c1)C(=O)N[C@@H](Cc1c[nH]c2ccccc12)C(=O)N[C@H](C(=O)N[C@H](C(=O)N[C@H](C(=O)N[C@@H](CCCNC(=N)N)C(=O)N[C@H](C(=O)O)C(C)(C)C)[C@@H](C)O)C(C)(C)C)C(C)(C)S]
Compound 25
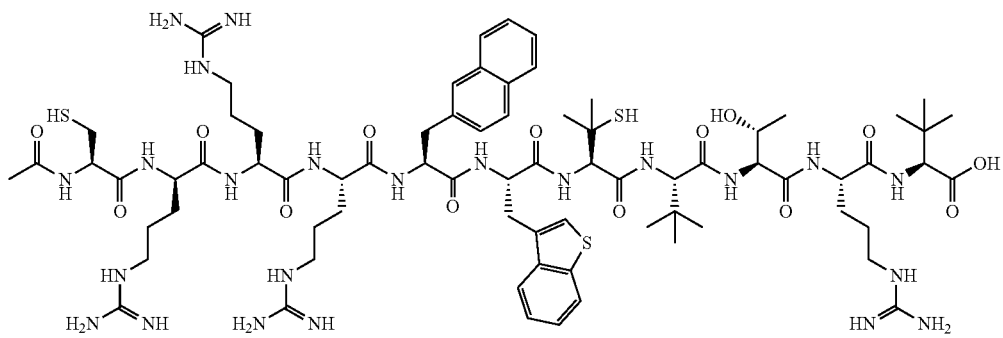 [SMILES: CC(=O)N[C@@H](CS)C(=O)N[C@H](CCCNC(=N)N)C(=O)N[C@@H](CCCNC(=N)N)C(=O)N[C@@H](CCCNC(=N)N)C(=O)N[C@@H](Cc1ccc2ccccc2c1)C(=O)N[C@@H](Cc1csc2ccccc12)C(=O)N[C@H](C(=O)N[C@H](C(=O)N[C@H](C(=O)N[C@@H](CCCNC(=N)N)C(=O)N[C@H](C(=O)O)C(C)(C)C)[C@@H](C)O)C(C)(C)C)C(C)(C)S]
Compound 26
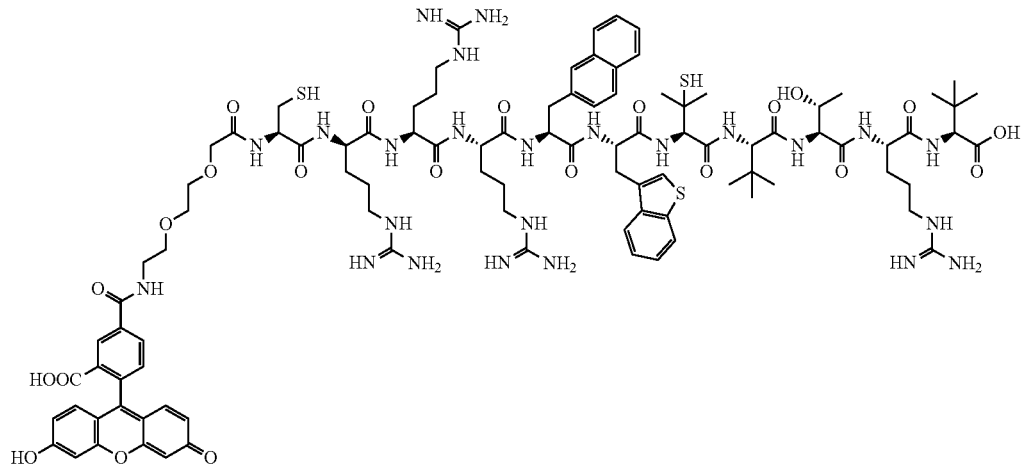 [SMILES: C[C@@H](O)[C@H](NC(=O)[C@@H](NC(=O)[C@@H](NC(=O)[C@H](Cc1csc2ccccc12)NC(=O)[C@H](Cc1ccc2ccccc2c1)NC(=O)[C@H](CCCNC(=N)N)NC(=O)[C@H](CCCNC(=N)N)NC(=O)[C@@H](CCCNC(=N)N)NC(=O)[C@H](CS)NC(=O)COCCOCCNC(=O)c1ccc(-c2c3ccc(=O)cc-3oc3cc(O)ccc23)c(C(=O)O)c1)C(C)(C)S)C(C)(C)C)C(=O)N[C@@H](CCCNC(=N)N)C(=O)N[C@H](C(=O)O)C(C)(C)C]
Compound 27
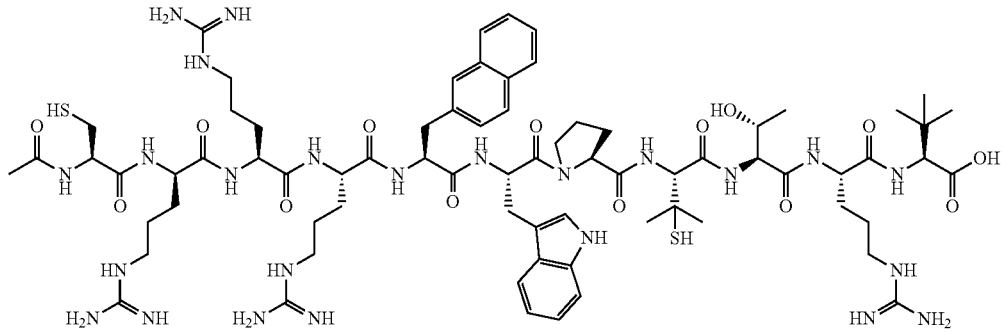 [SMILES: CC(=O)N[C@@H](CS)C(=O)N[C@H](CCCNC(=N)N)C(=O)N[C@@H](CCCNC(=N)N)C(=O)N[C@@H](CCCNC(=N)N)C(=O)N[C@@H](Cc1ccc2ccccc2c1)C(=O)N[C@@H](Cc1c[nH]c2ccccc12)C(=O)N1CCC[C@H]1C(=O)N[C@H](C(=O)N[C@H](C(=O)N[C@@H](CCCNC(=N)N)C(=O)N[C@H](C(=O)O)C(C)(C)C)[C@@H](C)O)C(C)(C)S]

TABLE 6-continued
Compound 27-FITC
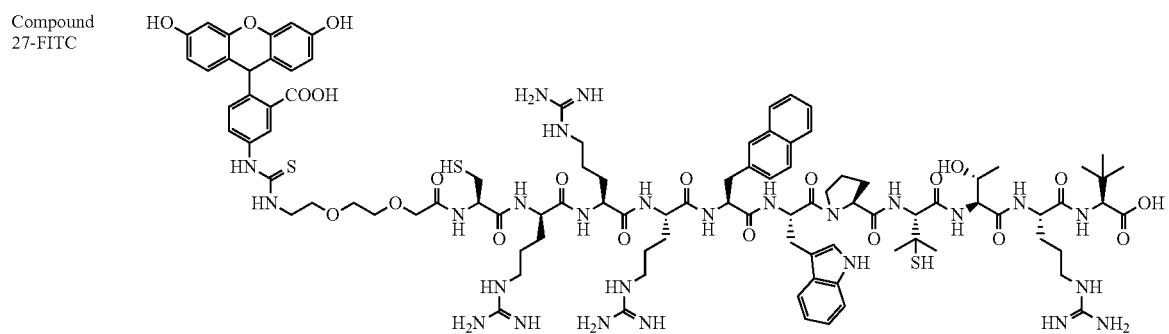
Compound 28
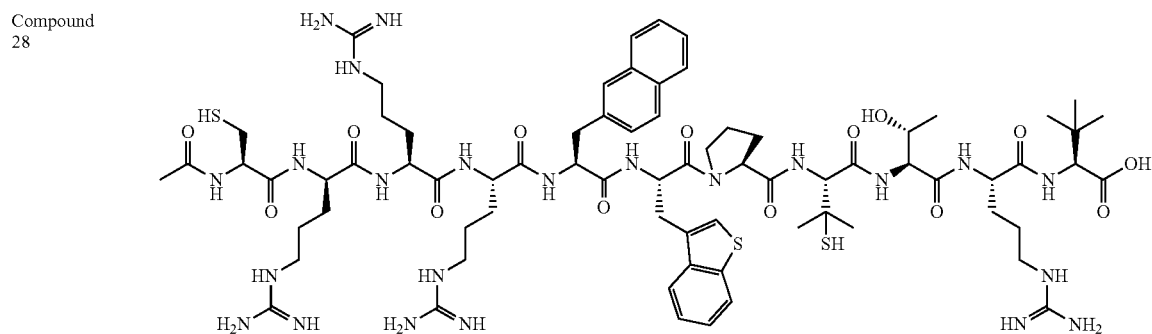
Compound 28-FITC
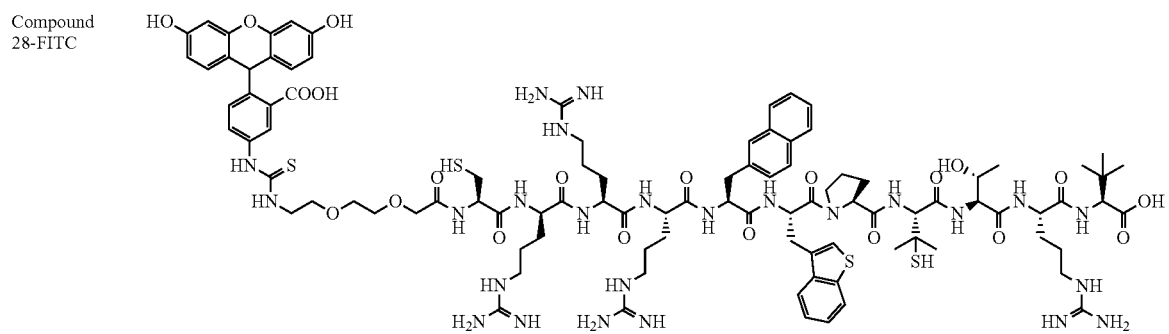
Compound 29
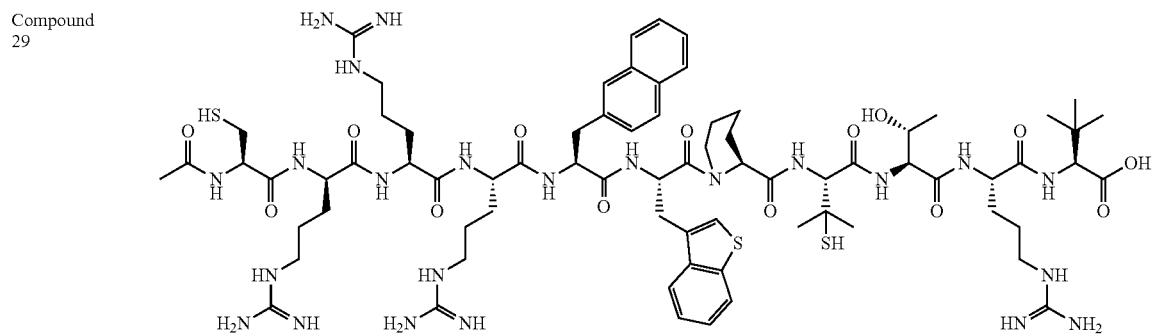

TABLE 6-continued
Compound 29-FITC
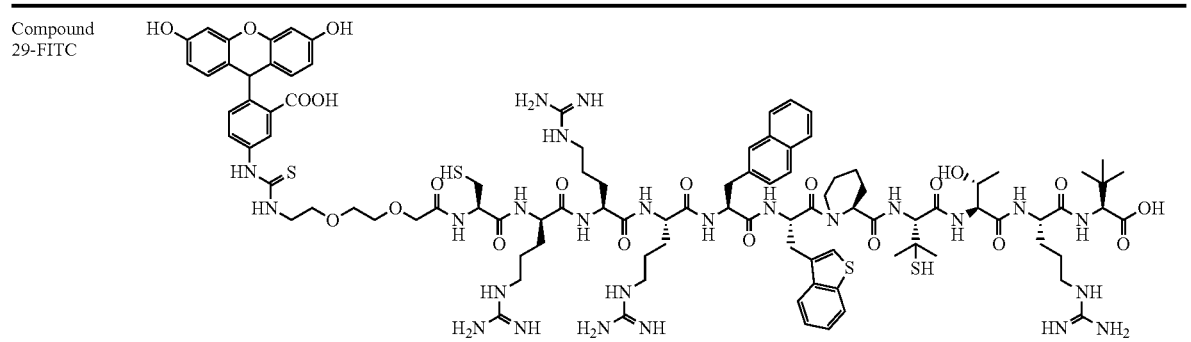
Compound 30
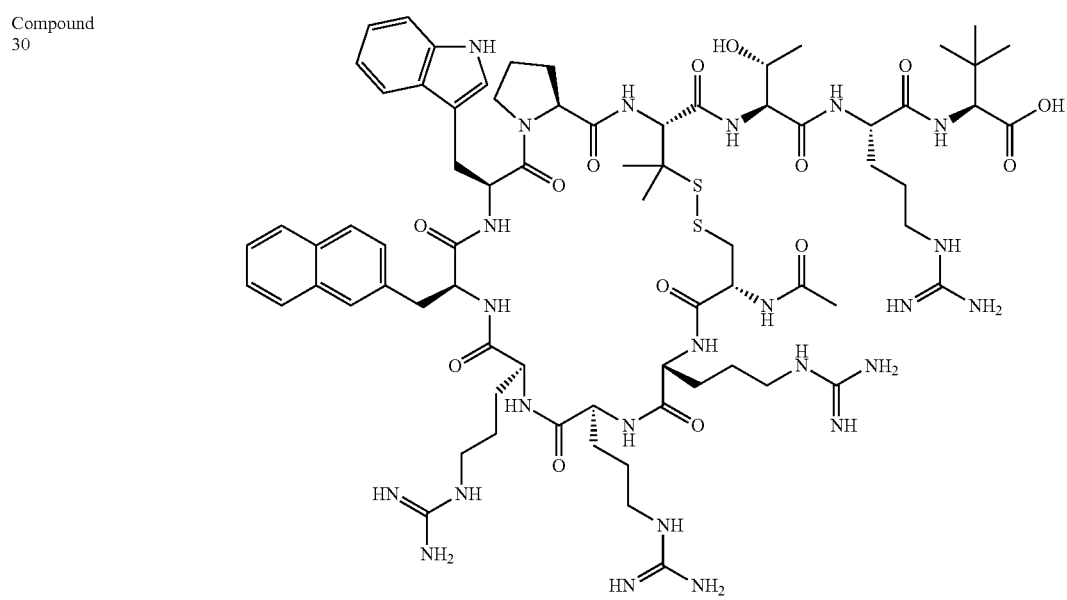
Compound 31
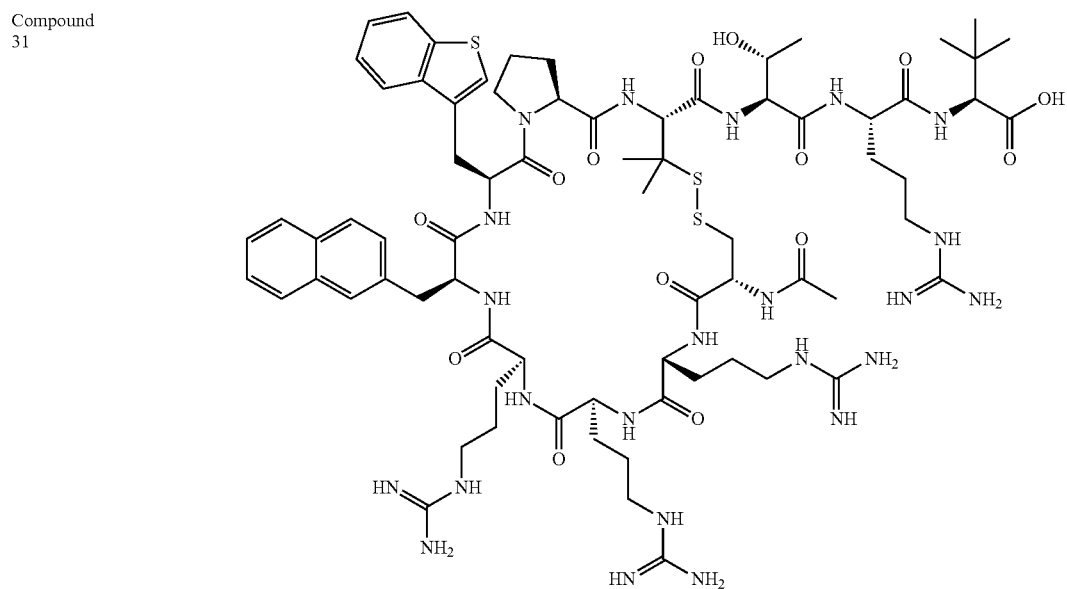

TABLE 6-continued

Compound 32 (PGD97)

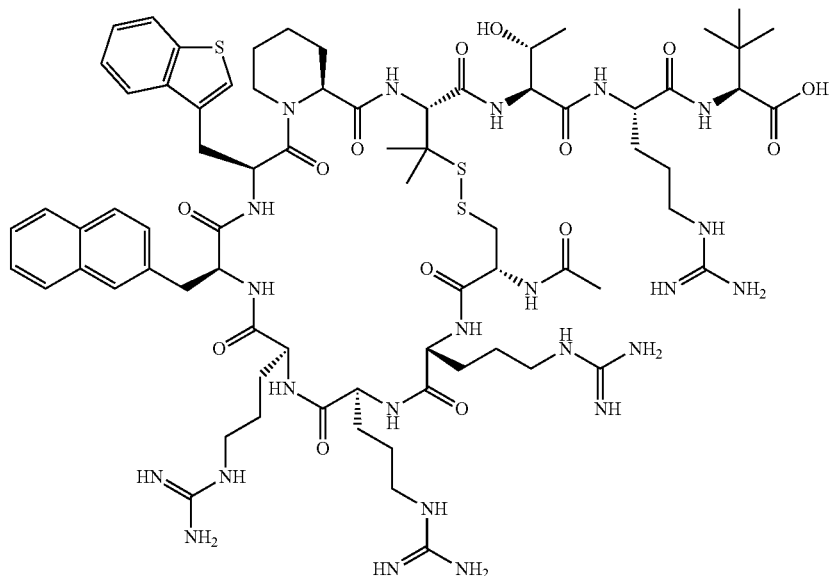 [SMILES: CC(=O)N[C@H]1CSSC(C)(C)[C@@H](C(=O)N[C@H](C(=O)N[C@@H](CCCNC(=N)N)C(=O)N[C@H](C(=O)O)C(C)(C)C)[C@@H](C)O)NC(=O)[C@@H]2CCCCN2C(=O)[C@H](Cc2csc3ccccc23)NC(=O)[C@H](Cc2ccc3ccccc3c2)NC(=O)[C@H](CCCNC(=N)N)NC(=O)[C@H](CCCNC(=N)N)NC(=O)[C@@H](CCCNC(=N)N)NC1=O]

Combination Therapies

The peptides disclosed herein can be administered in combination with one or more additional therapeutic agents used in the treatment of CF.

In one embodiment, the one or more additional agents is selected from a mucolytic agent, bronchodialator, an antibiotic, an anti-infective agent, an anti-inflammatory agent, a nutritional agent, a therapeutic agents corrects an improperly folded mutant CFTR protein, and a potentiator of ion channel gating.

In some embodiments, one or more of the additional therapeutic agents corrects an improperly folded mutant CFTR protein (referred to as a corrector). In some embodiments, the drug which corrects an improperly folded mutant CFTR protein is Lumacaftor, Tezacaftor, VX-152, or VX-440, or combinations thereof. In some embodiments, one or more of the additional therapeutic agent is a potentiator of ion channel gating (referred to as a potentiator). In some embodiments, the potentiator is Ivacaftor. Non-limiting examples of correctors and potentiators can be found in U.S. Patent App. Pub. 2012/0071504A1 and U.S. Pat. Nos. 9,139,530; 9,216,969; 8,754,224; 8,507,534; and 7,495,103, each of which is herein incorporated by reference in its entirety.

In some embodiments, the peptides of the disclosure can be administered in combination with a corrector and a potentiator. For example, the peptides (e.g., peptides according to Formula I and II), compositions, and methods disclosed herein can further comprise administering FDA-approved Vertex CFTR modulators, Lumacaftor (the corrector VX-809) and Ivacaftor (the potentiator VX-770). The potentiator Ivacaftor has been shown to improve the channel function of some of the less prevalent CFTR mutants (e.g., G551D). However, the FDA-approved combination (Lumacaftor/Ivacaftor) offers only modest benefits to patients with the most common mutation, F508del (~70% of all CF patients). Most recent data released by Vertex indicate that a triple combination of two correctors (Tezacaftor, and VX-152 or VX-440) and a potentiator (Ivacaftor) is able to improve the lung function of CF patients who have one F508del mutation by ~10%. Coadministering an inhibitor against lysosomal degradation of mutant CFTRs would further enhance the therapeutic effects of correctors (e.g., the newly developed corrector VX-661, Tezacaftor) and potentiators (e.g., Ivacaftor) against mutant CFTRs.

Methods of Making

The peptides described herein can be prepared using synthetic techniques known to one skilled in the art of organic synthesis or variations thereon as appreciated by those skilled in the art. The peptides described herein can be prepared from readily available starting materials. Optimum reaction conditions can vary with the particular reactants or solvents used, but such conditions can be determined by one skilled in the art.

Variations on the peptides described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenyl sulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carb oxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N, N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Compositions, Formulations and Methods of Administration

In vivo application of the disclosed peptides, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The peptides disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Compounds can also be incorporated into polymers, examples of which include poly (D-L lactide-co-glycolide) polymer; poly[bis(p-carboxyphenoxy) propane:sebacic acid] in a 20:80 molar ratio (as used in GLIADEL); chondroitin; chitin; and chitosan.

In certain examples, the peptides and compositions disclosed herein can be locally administered at one or more anatomical sites, optionally in combination with a pharmaceutically acceptable carrier such as an inert diluent. Peptides and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the peptide can be combined with one or more excipients and used in the form of ingestible tablets, buccal tablets, troches, capsules, elixirs, suspensions, syrups, wafers, aerosol sprays, and the like.

In some embodiments, the disclosed peptides and compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the peptide, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the peptide can be incorporated into sustained-release preparations and devices.

Peptides and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride.

Prolonged absorption of the injectable compositions can be brought about by the inclusion of agents that delay absorption, for example, aluminum monostearate and gelatin.

Sterile injectable solutions are prepared by incorporating a peptide disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, peptides disclosed herein can be applied in as a liquid or solid. However, it will generally be desirable to administer them topically to the skin as compositions, in combination with a dermatologically acceptable carrier, which can be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the peptides and compositions disclosed herein can be determined by comparing their in vitro activity, and in vivo activity in animal models. Methods for the extrapolation of effective dosages in mice, and other animals, to humans are known to the art.

The dosage ranges for the administration of the peptides are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a peptide disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more therapeutic agents used in the treatment of CF, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a peptide disclosed herein is provided in the kit as a solid, such as a tablet, pill, or powder form. In another embodiment, a peptide disclosed herein is provided in the kit as a liquid or solution. In one embodiment, the kit comprises an ampoule or syringe containing a compound and/or agent disclosed herein in liquid or solution form.

Methods of Use

Also provided herein are methods of use of the peptides compositions described herein. Also provided herein are methods for treating a disease or pathology in a subject in need thereof comprising administering to the subject an effective amount of any of the compounds or compositions described herein.

Also provided herein are methods of treating CF in a subject. The methods include administering to a subject an effective amount of one or more of the peptides (e.g., the peptides according to Formula I and II) or compositions described herein, or a pharmaceutically acceptable salt thereof.

The methods of treatment of CF described herein can further include treatment with one or more additional agents (e.g., a therapeutic agent used in the treatment of CF). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the peptides or pharmaceutically acceptable salts thereof and compositions as described herein. The administration of the one or more additional agents and the compounds and compositions or pharmaceutically acceptable salts thereof as described herein can be by the same or different routes. When treating with one or more additional agents, the peptides or pharmaceutically acceptable salts thereof as described herein can be combined into a pharmaceutical composition that includes the one or more additional agents.

Also described herein are methods of preventing CFTR from lysosomal degradation. The method includes contacting a CAL PDZ binding domain with an effective amount of peptide (e.g., the peptides according to Formula I and II) or composition as described herein. Also described herein are methods of inhibiting ligand binding to CAL-PDZ binding domain in a patient in need thereof. The method includes contacting a CAL PDZ binding domain with an effective amount of peptide (e.g., the peptides according to Formula I and II) or composition as described herein.

A number of embodiments of the invention have been described. Nevertheless, it will be understood that various modifications may be made without departing from the spirit and scope of the invention. Accordingly, other embodiments are within the scope of the following claims.

EXAMPLES

Example 1. Inhibitor Design Strategy

Figure 2:
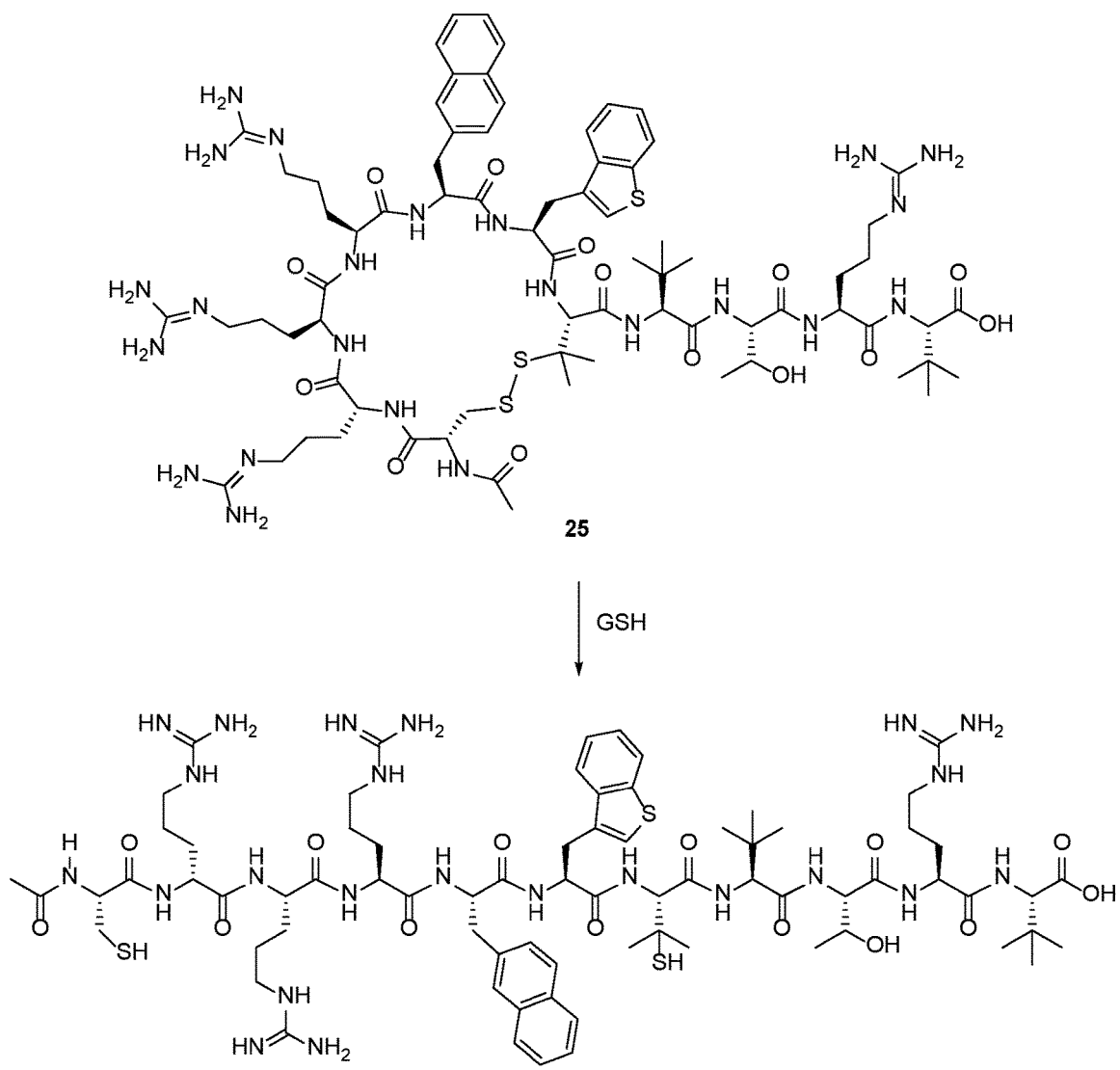
FIG. 2 illustrates the structures of peptide 25 before and after reductive ring opening.

FIG. 2 shows the strategy of CAL PDZ domain inhibitor design, by using peptide 25 as an example. Peptides were synthesized as disulfide-mediated cyclic peptides (i.e., cyclization of the peptides was achieved by forming an intramolecular disulfide bond between two moieties independently having thiol groups). When outside the cell (e.g., in circulation), the cyclic peptides have enhanced stability against proteolytic degradation and enhanced cell-permeability. Once inside the cytosol, the disulfide is reduced to generate the linear peptides as the active CAL PDZ domain inhibitors.

Example 2. Development of Inhibitors Having High Potency and Cell-Permeability

Computational and medicinal chemistry approaches were employed to improve the potency, cell-permeability, and proteolytic stability of peptide 8, starting from the C-terminus. First, the C-terminal valine (position 0) was replaced with a variety of residues and evaluated for binding to CAL PDZ domain in silico. Peptides containing the top four performing residues, isoleucine (Ile), β-cyclohexylalanine (Cha), α-methylleucine (MeLeu), and tert-leucine (Tle) were chemically synthesized and experimentally tested for binding using a fluorescence anisotropy (FA)-based competition assay. Compared to the original lead peptide (peptide 8), Tle increased the binding affinity by 2.7-fold, whereas the other three residues did not significantly improve binding (Table 7, peptides 1-5). Tle has the additional benefit of improving the proteolytic stability against carboxypeptidases and endopeptidases due to its bulky tert-butyl side chain. Tle was thus selected as the P0 residue in all further studies.

The same approach was applied to the more N-terminal positions. At the P-1 position, Arg was replaced with leucine (Leu), $N^\varepsilon$-nicotinoyllysine [Lys(NIC)], $N^\varepsilon$-trifluoroacetyllysine [Lys(TFA)], or homoarginine (homoArg). However, none of the substitutions further increased the CAL-binding affinity (Table 7, peptides 7-10) and therefore L-arginine was retained as the P-1 residue.

We next replaced the Gln at P-4 position with D-proline, D-cysteine, or L-cysteine (Table 7, peptides 11-13). A D-amino acid at the P-4 position would increase the proteolytic stability, whereas D/L-cysteine would provide an alternative site of cyclization. Cyclization at position P-4 (instead of P-3) would generate a smaller and more rigid ring, which would improve the metabolic stability and the cell-permeability of the peptide. At the P-5 site, replacement of Trp with 1- or 2-naphthylalanine did not significantly affect the binding (peptides 14 and 15).

We substituted L-penicillamine (Pen) for cysteine at the P-3 position, anticipating that the sterically hindered side chain of Pen would protect the peptide bonds N- and C-terminal to it from enzymatic degradation and stabilize the disulfide bond as well. Indeed, substitution of Pen also improved CAL binding by ~2-fold (IC50=680 nM for peptide 16). At position P-6, substitution of 1- or 2-naphthylalanine for Phe resulted in ~5-fold increase in CAL binding affinity, while D-2-naphthylalanine was less effective (peptides 17-19).

Next, we varied the stereochemical configuration of the N-terminal arginines, anticipating that D-arginine might improve the proteolytic stability and cell-permeability of the peptides. We found that a D-arginine at the P-9 position is tolerated.

We replaced the Gln at P-4 position of peptide 22 with a Pen and the Pen at the P-3 position with the isosteric Tle, to form a smaller ring (7 aa instead of 8 aa) and improve the proteolytic stability and cell-permeability (Table 7, peptide 24). Indeed, although these changes decreased CAL binding by ~2-fold, cyclization by disulfide formation greatly increased the cell-permeability of peptide 24 (4-fold higher than peptide 22). Finally, we replaced the Trp at the P-5 position with 3-(3-benzothienyl)-L-alanine (Bta), which is isosteric with Trp but is less prone to oxidative degradation. This substitution gave peptide 25, which is 1.5-fold more potent than peptide 24 in CAL binding (IC50=235 nM) and has >5-fold improvement in cell-permeability, most likely due to the greater hydrophobicity of the benzothienyl group relative to the indolyl ring of Trp. When labeled at the N-terminus with fluorescein and tested for binding to CAL PDZ domain by FA, a $K_D$ value of 49±3 nM was obtained (Table 1, peptide 26).

Peptide 25 has similar in vitro potency for CAL binding to peptide 20, but has excellent cell-permeability (~20-fold better than peptide 20 or 5-fold better than CPP9) and proteolytic stability (e.g., orally active).

TABLE 7

Sequences and CAL PDZ-Binding Affinities of Peptides of this Disclosure

| Compd | Sequence | $IC_{50}$ (nM) | Uptake (% rel.)$^d$ |
|---|---|---|---|
| 1 | Ac-<u>Arg-Arg-Phe-Trp-Gln-Cys-Thr-Arg-Val</u>-OH (SEQ ID NO: 121, underlined portion only) | 4520$^a$ | ND |
| 2 | Ac-<u>Arg-Arg-Phe-Trp-Gln-Cys-Thr-Arg-Ile</u>-OH (SEQ ID NO: 122, underlined portion only) | 3690$^a$ | ND |
| 3 | Ac-<u>Arg-Arg-Phe-Trp-Gln-Cys-Thr-Arg-Cha</u>-OH (SEQ ID NO: 123, underlined portion only) | 7880$^a$ | ND |
| 4 | Ac-<u>Cys-Arg-Arg-Arg-Phe-Trp-Gln-Cys-Thr-Arg-MeLeu</u>-OHn (SEQ ID NO: 124, underlined portion only) | >20000$^b$ | ND |
| 5 | Ac-<u>Arg-Arg-Phe-Trp-Gln-Cys-Thr-Arg-Tle</u>-OH (SEQ ID NO: 125, underlined portion only) | 1700$^a$ | ND |
| 6 | FITC-<u>Cys-Arg-Arg-Arg-Phe-Trp-Gln-Cys-Thr-Arg-Tle</u>-OH (SEQ ID NO: 126, underlined portion only) | 996 ± 104 ($K_D$)$^c$ | ND |
| 7 | Ac-<u>Arg-Arg-Phe-Trp-Gln-Cys-Thr-Leu-Tle</u>-OH (SEQ ID NO: 127, underlined portion only) | 2020$^a$ | ND |

TABLE 7-continued

Sequences and CAL PDZ-Binding Affinities of Peptides of this Disclosure

| Compd | Sequence | IC$_{50}$ (nM) | Uptake (% rel.)[d] |
|---|---|---|---|
| 8 | Ac-Arg-Arg-Phe-Trp-Gln-Cys-Thr-Lys(NIC)-Tle-OH (SEQ ID NO: 128, underlined portion only) | 2440[a] | ND |
| 9 | Ac-Arg-Arg-Phe-Trp-Gln-Cys-Thr-Lys(TFA)-Tle-OH (SEQ ID NO: 129, underlined portion only) | 2520[a] | ND |
| 10 | Ac-Arg-Arg-Phe-Trp-Gln-Cys-Thr-(HomoArg)-Tle-OH (SEQ ID NO: 130, underlined portion only) | 2220[a] | ND |
| 11 | Ac-Arg-Arg-Phe-Trp-(D-Pro)-Cys-Thr-Arg-Tle-OH (SEQ ID NO: 131, underlined portion only) | 7390[a] | ND |
| 12 | Ac-Arg-Arg-Phe-Trp-(D-Cys)-Cys-Thr-Arg-Tle-OH (SEQ ID NO: 132, underlined portion only) | 10300[a] | ND |
| 13 | Ac-Arg-Arg-Phe-Trp-Cys-Cys-Thr-Arg-Tle-OH (SEQ ID NO: 133, underlined portion only) | 8010[a] | ND |
| 14 | Ac-Cys-Arg-Arg-Arg-Phe-(1-Nal)-Gln-Cys-Thr-Arg-Tle-OH (SEQ ID NO: 134, underlined portion only) | 1770[b] | ND |
| 15 | Ac-Cys-Arg-Arg-Arg-Phe-(2-Nal)-Gln-Cys-Thr-Arg-Tle-OH (SEQ ID NO: 135, underlined portion only) | 1490[b] | ND |
| 16 | Ac-Cys-Arg-Arg-Arg-Phe-Trp-Gln-Pen-Thr-Arg-Tle-OH (SEQ ID NO: 136, underlined portion only) | 680[b] | ND |
| 17 | Ac-Cys-Arg-Arg-Arg-(1-Nal)-Trp-Gln-Pen-Thr-Arg-Tle-OH (SEQ ID NO: 137, underlined portion only) | 148[b] | ND |
| 18 | Ac-Cys-Arg-Arg-Arg-(2-Nal)-Trp-Gln-Pen-Thr-Arg-Tle-OH (SEQ ID NO: 138, underlined portion only) | 146[b] | ND |
| 19 | Ac-Cys-Arg-Arg-Arg-(D-2-Nal)-Trp-Gln-Pen-Thr-Arg-Tle-OH (SEQ ID NO: 139, underlined portion only) | 370[b] | ND |
| 20 | Ac-Cys-(D-Arg)-Arg-Arg-(2-Nal)-Trp-Gln-Pen-Thr-Arg-Tle-OH (SEQ ID NO: 140, underlined portion only) | 165[b] | 28 ± 1 |
| 21 | Ac-Cys-(D-Arg)-(D-Arg)-Arg-(2-Nal)-Trp-Gln-Pen-Thr-Arg-Tle-OH (SEQ ID NO: 141, underlined portion only) | 270[b] | 23 ± 4 |
| 22 | Ac-Cys-Arg-(D-Arg)-Arg-(2-Nal)-Trp-Gln-Pen-Thr-Arg-Tle-OH (SEQ ID NO: 142, underlined portion only) | 401[a] | 17 ± 2 |
| 23 | FAM-miniPEG-Cys-(D-Arg)-Arg-Arg-(2-Nal)-Trp-Pro-Pen-Thr-Arg-Tle-OH (SEQ ID NO: 143, underlined portion only) | 168 (K$_D$)[c] | ND |
| 24 | Ac-Cys-(D-Arg)-Arg-Arg-(2-Nal)-Trp-Pen-Tle-Thr-Arg-Tle-OH (SEQ ID NO: 144, underlined portion only) | 380[b] | 92 |
| 25 | Ac-Cys-(D-Arg)-Arg-Arg-(2-Nal)-(Bta)-Pen-Tle-Thr-Arg-Tle-OH (SEQ ID NO: 145, underlined portion only) | 235[b] | 518 ± 74 |
| 26 | FAM-miniPEG-Cys-(D-Arg)-Arg-Arg-(2-Nal)-(Bta)-Pen-Tle-Thr-Arg-Tle-OH (SEQ ID NO: 146, underlined portion only) | 49 ± 3 (K$_D$)[c] | ND |

Ac = acetyl, 1-Nal = 3-(1-Naphthyl)-L-alanine, 2-Nal = 3-(2-Naphthyl)-L-alanine, D-2-Nal = 3-(2-Naphthyl)-D-alanine, FITC = 5-fluorescein isothiocyanate, Tle = tert-butyl-L-alanine, Pen = penicillamine, Bta = 3-(3-benzothienyl)-L-alanine, Cha = 3-cyclohexyl-L-alanine, HomoArg = L-homoarginine, Lys(NIC) = Nicotinyl-L-lysine, Lys(TFA) = Trifluoroacetyl-L-Lysine, miniPEG = 2-(2-(2-aminoethoxy)ethoxy)acetamide, FAM = 5-carboxyfluorescein, MeLeu = α-methyl-L-leucine.
[d] All values are relative to that of CPP9 (100%).

Example 3. Ex Vivo Efficacy of CAL PDZ Inhibitors

Figure 3A:
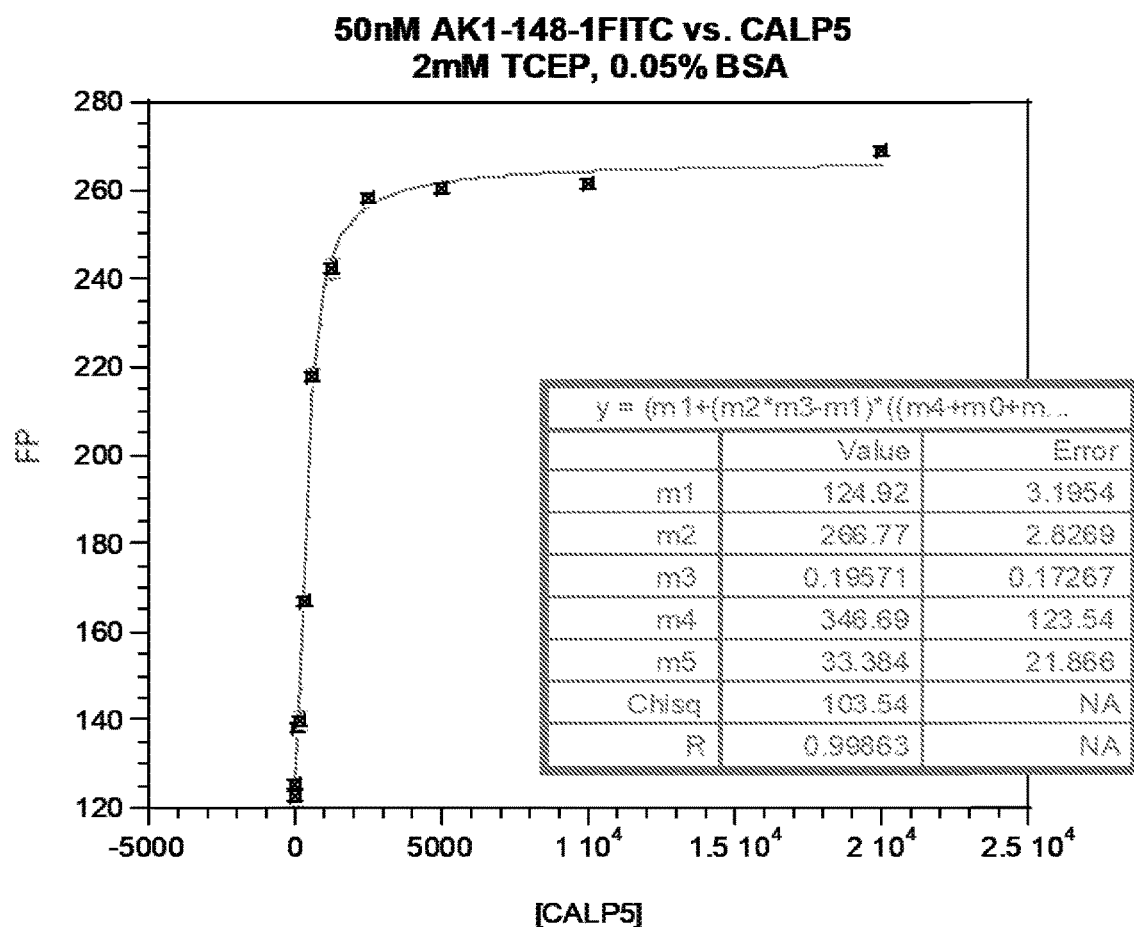
FIG. 3A graphically illustrates binding of FITC-labeled peptide 20 to CAL PDZ domain as monitored by fluorescence polarization (FP), with a $K_D$ (m5) value of 33 nM.
Figure 3B:
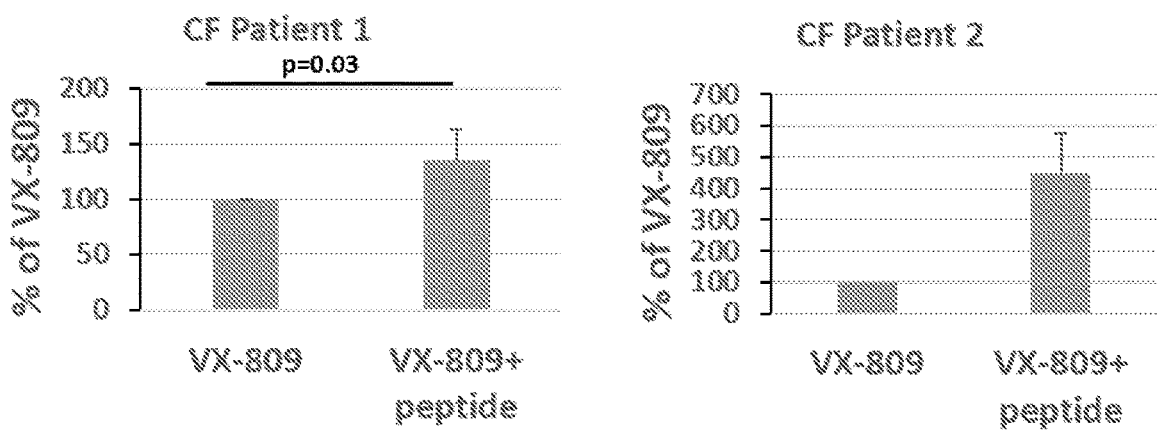
FIG. 3B graphically illustrates increase in CFTR ion currents in the presence of peptide 20.

We tested peptide 20 (K$_D$~50 nM for CAL PDZ; FIG. 3a) against primary bronchial cells derived from two homozygous F508del patients in combination with Lumacaftor using Ussing chambers. Primary HAEC from 2 CF patients homozygous for F508del mutation were treated for 48 h with 5 μM VX-809 and then for 2 h with or without 5 μM peptide 20. CFTR currents were measured using Ussing chambers after addition of forskolin. Peptide 20 (at 5 μM) increased ion transport by 1.5- and 4.8-fold, respectively, relative to the Lumacaftor only control (FIG. 3b).

Preliminary tests with peptide 25 demonstrated robust cellular activity at 50 nM concentration. One hour after oral gavage, tetramethylrhodamine (TMR)-labeled peptide 25

Figure 3C:
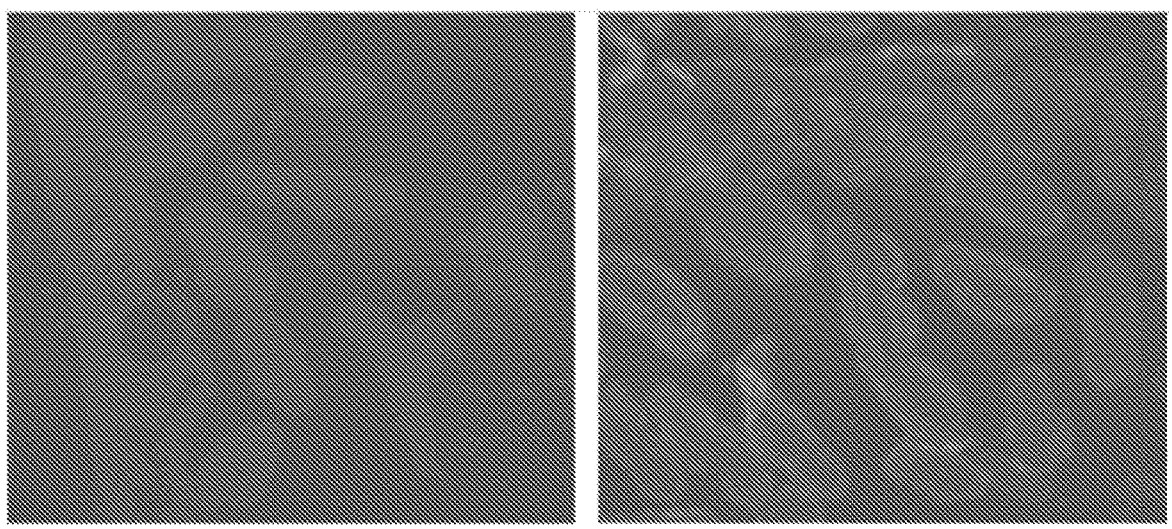
FIG. 3C depicts fluorescence levels in intestinal epithelial cells of healthy mice 1 h after oral gavage of tetramethylrhodamine (TMR, left panel) or TMR-labeled peptide 25 (right panel).

(structurally similar to peptide 26, except that FAM is replaced with TMR) was found at significant levels inside intestinal epithelial cells of healthy mice. The data suggest that at least a fraction of peptide 25 survived the GI tract and entered the intestinal epithelial cells, suggesting that peptide 25 may be given orally to cystic fibrosis patients to alleviate symptoms in the GI tract caused by mutant CFTR (FIG. 3c).

The peptides are effective as a monotherapy against some of the CFTR mutants. Further, the data indicates that a triple combination of a corrector (e.g., Tezacaftor), a potentiator (e.g., Ivacaftor), and a stabilizer (e.g., any of the peptides disclosed herein) would target all three defects described above and significantly increase the ion transport activity of F508del CFTR relative to the current treatment (e.g., the Tezacaftor/Ivacaftor combination).

Example 4. Measuring Binding Affinity

Condition A (denoted with superscript [a]): 50 nM probe (FAM-miniPEG-C-rRR-2-Nal-Bta-Pen-ZTRZ-OH (peptide 26) was incubated with 100 nM CALP5-His in pH 7.4 PBS containing 0.01% Triton-X100 and 2 mM TCEP for 1 h at room temperature. Serial dilutions of each competitor peptide were prepared in PBS containing 0.01% Triton-X100 to which the incubation solution was added. The combined solutions were incubated for 1 h at RT, after which 20 µL from each sample was pipetted into 384-well black-on-black microplates and fluorescence polarization was measured using a TECAN Infinite M1000 plate reader. Data was processed to determine $IC_{50}$ using GraphPad PRISM ver. 6.0.

Condition B (denoted in table with superscript [b]): 100 nM probe (FAM-ANSRWPTSII-OH (SEQ ID NO:158, underlined portion)) was incubated with 500 nM CALP5-His in pH 7.4 PBS containing 5 mM DTT for 1 h. Serial dilutions of each competitor peptide were prepared in PBS and the incubation solution was added to each. The combined solutions were gently mixed for 1 h at RT after which 20 uL sample was pipetted into 384-well black-on-black microplates and fluorescence polarization was measured using a TECAN Infinite M1000 plate reader. Data was processed to determine $IC_{50}$ using GraphPad PRISM ver. 6.0.

Condition C (denoted with superscript [c]): 50 nM labeled peptide was incubated with 2 mM TCEP in PBS at pH 7.4 containing 0.01% Triton-X100. CALP5-His was serially diluted in PBS containing 0.01% Triton-X100 to which was then added the peptide and TCEP solution. This solution was mixed for 1 h at RT then 20 uL was pipetted into 384-well microplates and fluorescence polarization was measured using a TECAN Infinite M1000 plate reader. $K_D$ values were calculated using KaleidaGraph v. 3.6 using the equation:

Cellular Uptake Efficiency: HeLa cells were seeded into 12-well cell-culture treated plates at a final density of $15 \times 10^4$ cells/well in DMEM supplemented with 10% FBS and 1% penicillin/streptomycin and incubated overnight at 37° C. and 5% $CO_2$. After 24 h, the media was aspirated followed by washing the cells three times with warm DPBS. Peptides were diluted to a final concentration of 5 µM in DMEM containing 10% FBS with 1% penicillin/streptomycin, added to each well and then incubated for 2 h at 37° C. and 5% $CO_2$. After 2 h, treatment media was aspirated and the cells were washed three times with ice-cold DPBS. Cells were removed from the plate via treatment with trypsin/EDTA and then harvested in ice-cold DPBS followed by centrifugation at ×300 RCF, 4° C. for 5 min. Cells were resuspended in DPBS and quantified using a BD Biosciences LSR II flow cytometer and gated using FlowJo. Values for uptake are provided as a percentage relative to positive control, CPP9 ([cyclo-fΦRrRrQ]-miniPEG-K[NF]).

Example 5. Cellular Activity

5 µM treatment with each compound on primary cells. Values reported are the percent increase in current compared to treatment with VX809 alone.

Example 6. Additional CAL PDZ Inhibitors

Figure 4:
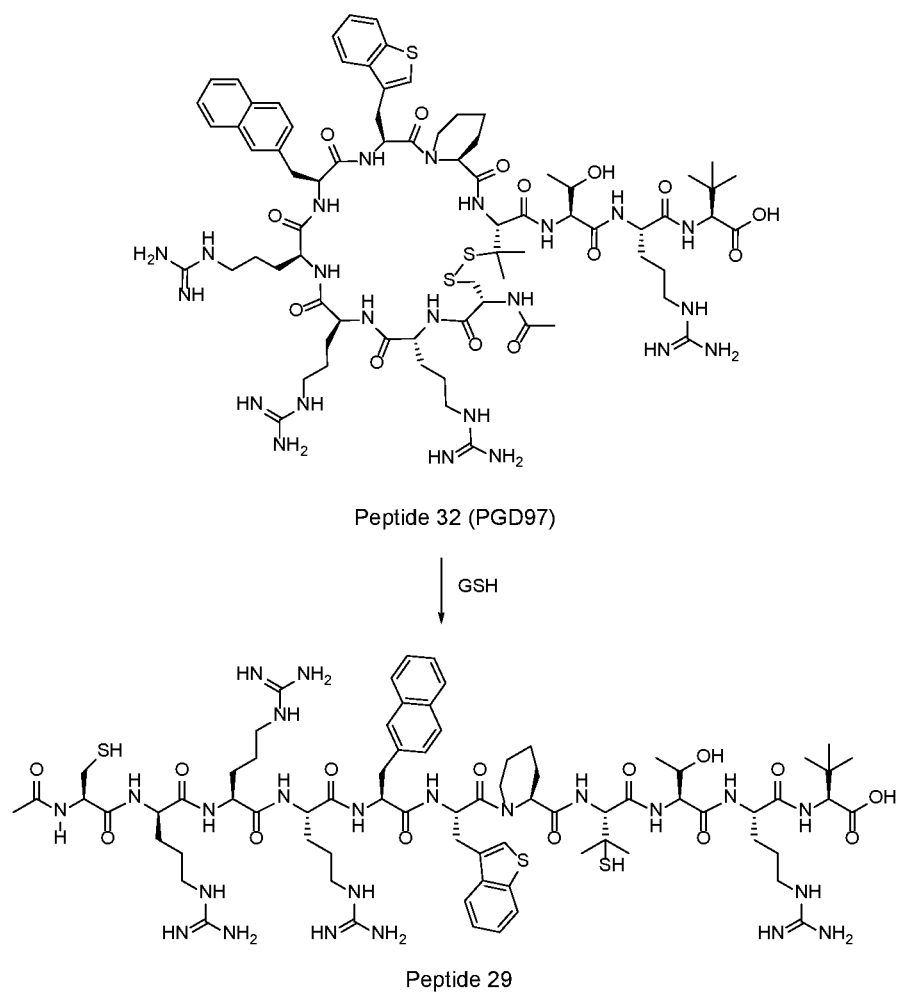
FIG. 4 shows the structure of PGD97, which is converted into peptide 29 by glutathione (GSH) upon entry into the cytosol of mammalian cells.
Figure 5:
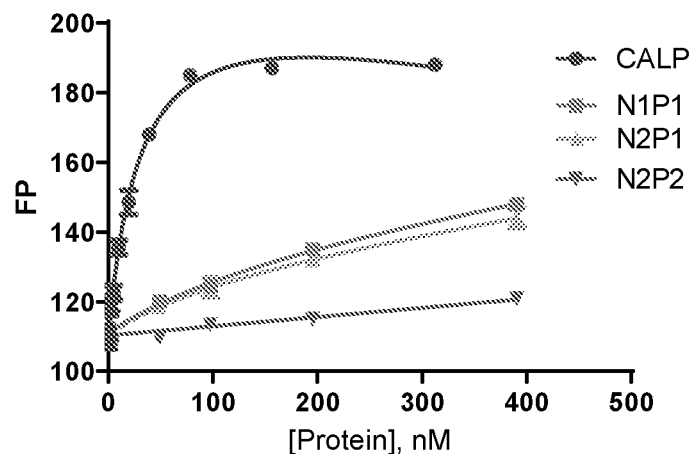
FIG. 5 graphically represents binding of FITC-labeled peptide 29 to CAL and NHERF PDZ domains as measured by FP.

Compound 25 was the most potent CAL PDZ inhibitor and was the basis for further modification. When labeled with an N-terminal fluorescein (FAM), the resulting peptide (26) bound CAL PDZ domain with a $K_D$ value of 49±3 nM, but has relatively low specificity for CAL PDZ domain, relative to other PDZ domains involved in CFTR trafficking (e.g., NHERF PDZ domains). To improve the inhibitor selectivity (and potentially potency), we replaced the Gln residue at position −4 in peptide 20 with a proline, which was previously shown to be tolerated by the CAL PDZ domain, to produce peptide 27 (Table 8; $K_D$=179 nM). Replacement of Trp at the −5 position with 3-(3-benzothienyl)-L-alanine (Bta) resulted in peptide 28 (Table 8; $K_D$=87 nM). Next, we replaced the proline with L-pipecolic acid (Pip), as in silico modeling suggested that Pip is well tolerated at this position. Substitution of Pip for Pro not only improved the CAL PDZ-binding affinity by ~15-fold ($K_D$=6 nM for peptide 29), it also greatly improved its selectivity for CAL vs NHERF PDZ domains (as reported below). Structures of peptides 29 and 32 (named as "PGD97") are shown in FIG. 4. Structures of other compounds are shown in FIG. 5.

$$FP = \frac{\left(A_{min} + \left(A_{max} \times \frac{Q_b}{Q_f} - A_{min}\right)\left(\frac{(L + x + K_d) - \sqrt{(L + x + K_d)^2 - 4Lx}}{2L}\right)\right)}{\left(1 + \left(\frac{Q_b}{Q_f} - 1\right)\left(\frac{(L + x + K_d) - \sqrt{(L + x + K_d)^2 - 4Lx}}{2L}\right)\right)}$$

TABLE 8

Sequences and CAL PDZ-Binding Affinity of Peptides of this Disclosure.

| Peptide No. | Sequence | Affinity ($K_D$, nM) |
|---|---|---|
| 27 | Ac-<u>Cys-(D-Arg)-Arg-Arg-Nal-Trp-Pro-Pen-Thr-Arg-Tle</u>-OH (SEQ ID NO: 147, underlined portion only) | ND |
| 27-FITC | FITC-miniPEG-<u>Cys-(D-Arg)-Arg-Arg-Nal-Trp-Pro-Pen-Thr-Arg-Tle</u>-OH (SEQ ID NO: 148, underlined portion only) | 179 ± 42 |
| 28 | Ac-<u>Cys-(D-Arg)-Arg-Arg-Nal-Bta-Pro-Pen-Thr-Arg-Tle</u>-OH (SEQ ID NO: 149, underlined portion only) | ND |
| 28-FITC | FITC-miniPEG-<u>Cys-(D-Arg)-Arg-Arg-Nal-Bta-Pro-Pen-Thr-Arg-Tle</u>-OH (SEQ ID NO: 150, underlined portion only) | 87 ± 14 |
| 29 | Ac-<u>Cys-(D-Arg)-Arg-Arg-Nal-Bta-Pip-Pen-Thr-Arg-Tle</u>-OH (SEQ ID NO: 151, underlined portion only) | ND |
| 29-FITC | FITC-miniPEG-<u>Cys-(D-Arg)-Arg-Arg-Nal-Bta-Pip-Pen-Thr-Arg-Tle</u>-OH (SEQ ID NO: 152, underlined portion only) | 6.0 ± 3.0 |
| 30 | Ac-<u>Cys\*-(D-Arg)-Arg-Arg-Nal-Trp-Pro-Pen\*-Thr-Arg-Tle</u>-OH (SEQ ID NO: 153, underlined portion only) | ND |
| 31 | Ac-<u>Cys\*-(D-Arg)-Arg-Arg-Nal-Bta-Pro-Pen\*-Thr-Arg-Tle</u>-OH (SEQ ID NO: 154, underlined portion only) | ND |
| 32 | Ac-<u>Cys\*-(D-Arg)-Arg-Arg-Nal-Bta-Pip-Pen\*-Thr-Arg-Tle</u>-OH (SEQ ID NO: 155, underlined portion only) | ND |

Where Ac = acetyl, Bta = 3-(3-benzothienyl)-L-alanine, FITC = fluorescein isothiocyanate, Binding Affinity and Selectivity. The potency and selectivity of inhibitor 29 was first assessed by comparing its binding affinity to the four PDZ domains of CAL, NHERF1, and NHERF2, which are involved in the trafficking of CFTR to and from the plasma membrane. Peptides were labeled with FITC at the N-terminus through a miniPEG linker and tested for binding to various PDZ domains by fluorescence polarization (FP). FITC-labeled peptide (50 nM) was incubated with varying concentrations of PDZ domain in PBS (pH 7.4) containing 0.01% Triton X-100 and 2 mM TCEP for 1 h at room temperature. After 1 h, 20 µL of each sample was pipetted into 384-well black-on-black microplates and fluorescence polarization was measured by using a TECAN Infinite M1000 plate reader. Data was processed using GraphPad PRISM ver. 8.0. Inhibitor 29 bound to the CAL PDZ domain with a $K_D$ of 6.0±3.0 nM, while its $K_D$ values for NHERF1/2 PDZ domains ranged from 780 to 7480 nM, representing ≥130-fold selectivity for the intended CAL PDZ domain (FIG. 5 and Table 9). In comparison, an earlier generation, peptide 20, showed a $K_D$ of 110 nM and only 14- to 36-fold selectivity for CAL vs NHERF PDZ domains. Thus, incorporation of Pip dramatically improved both potency and specificity of the inhibitor for CAL PDZ domain.

TABLE 9

Binding affinity (KD) of peptides 20 and 29 for CAL (CALP), NHERF1-PDZ1 (N1P1), NHERF2-PDZ1 (N2P1), and NHERF2-PDZ2 domains (N2P2).

| Compound | $K_D$ (nM) | | | |
|---|---|---|---|---|
| | CALP | N1P1 | N2P1 | N2P2 |
| 20 | 110 ± 10 | 1640 ± 150 | 2980 ± 150 | 4970 ± 890 |
| 29-FITC | 6.0 ± 3.0 | 780 ± 10 | 1370 ± 380 | 7480 ± 580 |

Figure 6A:
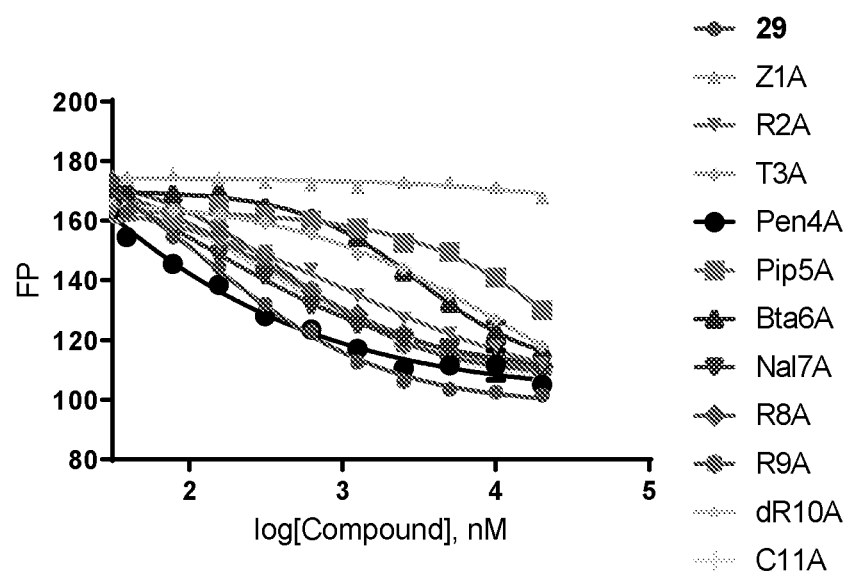
FIG. 6 (*a*) Competition of alanine mutant peptides for binding to CAL PDZ domain as monitored by FP.

SAR by Alanine Scanning. To determine which residues are critical for CAL PDZ domain binding, each residue of peptide 29 was replaced with Ala or D-Ala and the binding affinity of the resulting peptides were determined by an FP-based competition assay (FIG. 6a). Briefly, CAL PDZ domain (100 nM) was incubated with 50 nM probe (FAM-miniPEG-C-rRR-Nal-Bta-Pen-ZTRZ-OH (peptide 26) in PBS (pH 7.4) containing 0.01% Triton X-100 and 2 mM TCEP for 1 h at room temperature. Serial dilutions of competitor peptide were prepared in PBS containing 0.01% Triton X-100 and added to the above incubation solution. The combined solutions were incubated for an additional hour at RT and 20 µL of each sample was pipetted into 384-well black-on-black microplates. FP values were measured using a TECAN Infinite M1000 plate reader. Data was processed to determine $IC_{50}$ using GraphPad PRISM ver. 7.0.

Figure 6B:
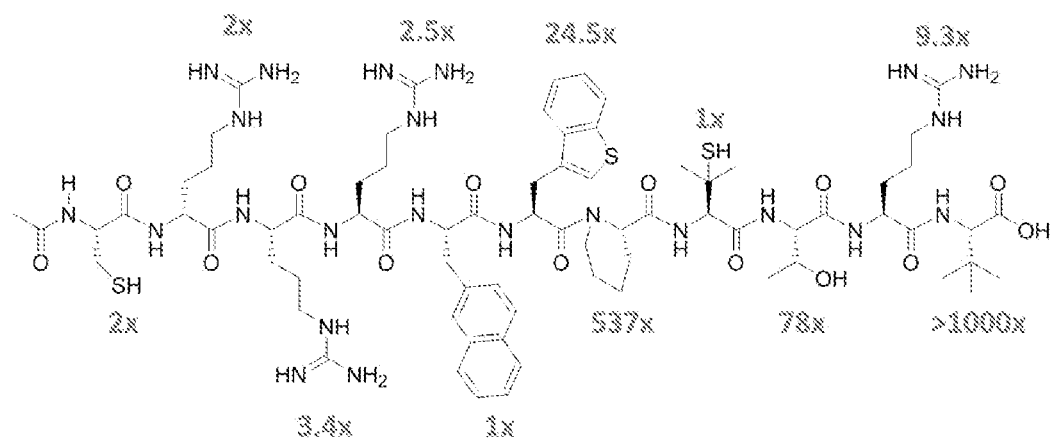

Alanine scan revealed that the C-terminal tert-leucine and Pip residues are most critical for CAL PDZ binding. Substitution of Ala for tert-leucine almost completely abolished CAL binding, whereas replacement of Pip with reduced the binding affinity by 537-fold (FIG. 6b). Thr at position −2, Bta at position −5, and Arg at position −1 also contribute greatly to CAL PDZ binding. The three Arg residues of the CPP motif also make minor contributions to CAL binding. Bta was also determined to be critical for cellular uptake.

Figure 7:
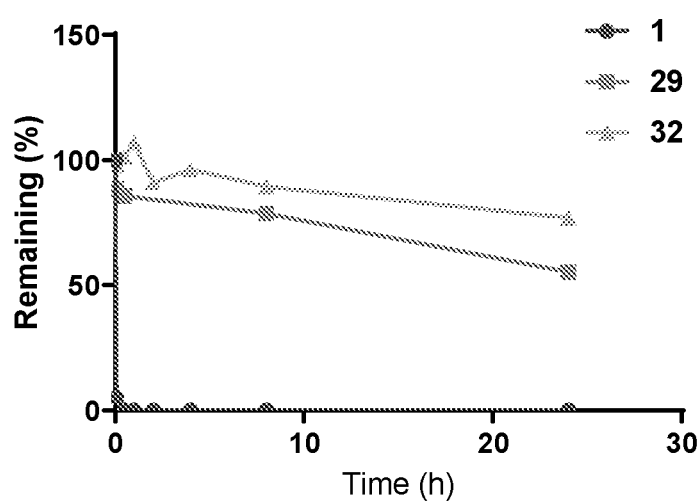
FIG. 7 Serum stability of peptides 1, 29, and 32. Data shown are amounts of remaining intact peptide as a function of incubation time.

Human Serum Stability. Whole human serum was diluted 1:4 in sterile DPBS and equilibrated at 37° C. for 15 min. Peptide (final concentration 100 µM) was added to the diluted serum and incubated at 37° C. with gentle mixing. At varying time points, 100 µL aliquots were withdrawn and quenched with 100 µL of 15% trichloroacetic acid (TCA) in MeOH (w/v) and 100 µL of MeCN and stored at 4° C. for 24 h. The sample was centrifuged (15000 g, 5 min, at 4° C.) and analyzed by RP-HPLC. PGD97 was highly stable in serum, undergoing ~20% degradation after 24 h. The reduced form of PGD97 (peptide 29) was slightly less stable, but still had a serum $t_{1/2}$ of >24 h. In comparison, peptide 1 (Ac-Arg-Arg-Phe-Trp-Gln-Cys-Thr-Arg-Val-OH), which was the starting point of this medicinal chemistry campaign, was completely degraded within the first hour (FIG. 7).

Figure 8:
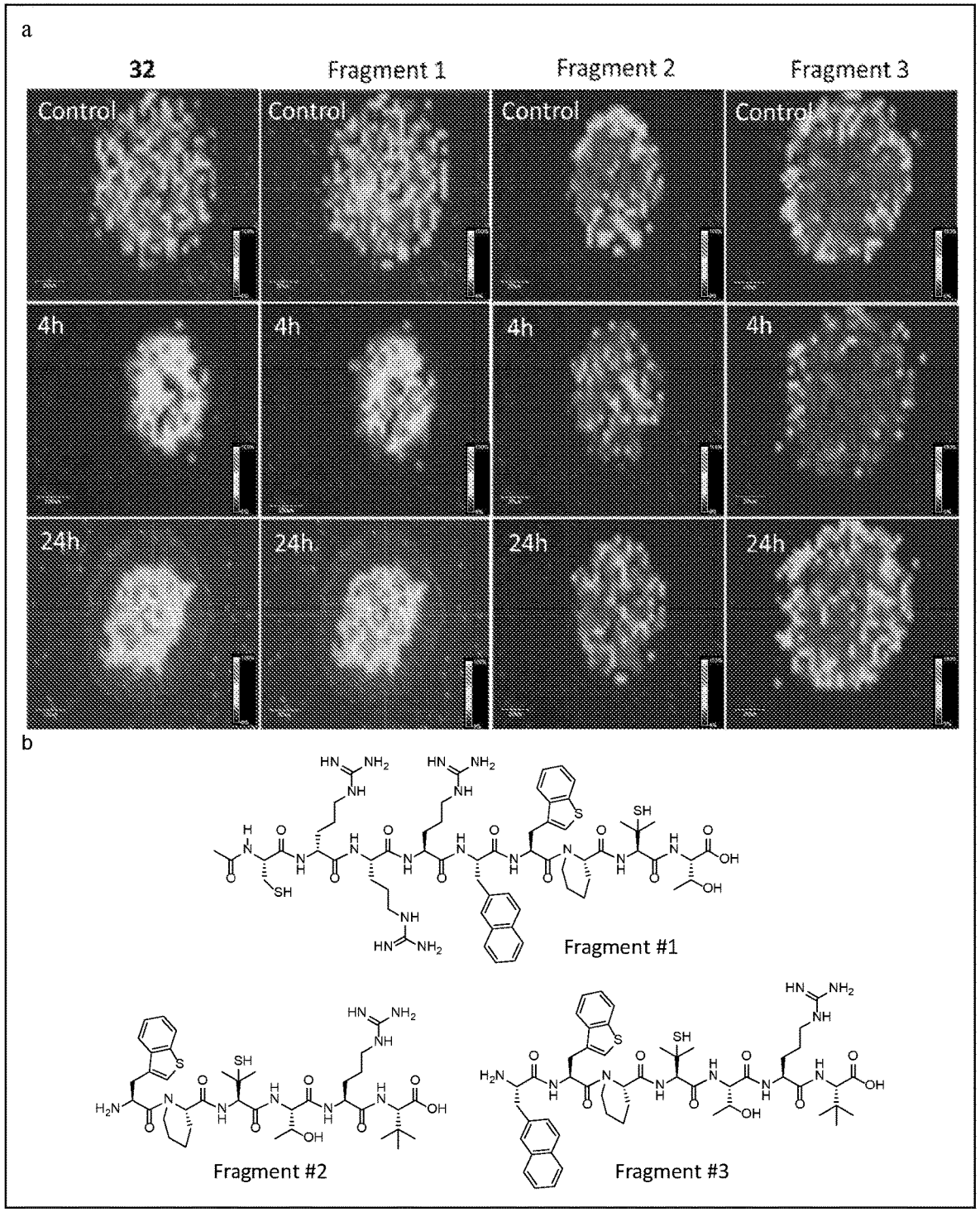
FIG. 8 (*a*) illustrates intracellular stability of peptide 29 (reduced form of PGD97) in HCT116 spheroids. Heatmaps are provided for intact peptide 29 and three representative proteolytic fragments at 0, 4, and 24 h.

Intracellular Stability. PGD97 (5 μM) was added to HCT116 cell spheroids in RPMI-1640 medium supplemented with 10% FBS and 1% penicillin/streptomycin and incubated for 4 or 24 h. After incubation, spheroids were washed 3× with DPBS, quickly frozen, embedded in a solid support, and cryo-sectioned. Prior to analysis, sinapinic acid was sublimed onto individual slides. The sample was imaged using a Bruker ultrafleXtreme MALDI-TOF-TOF and analyzed for the presence of proteolytic degradation fragments. Heatmaps, scaled relative to the most intense signal, were generated for the intact peptide (both 29 and 32) as well as ~20 potential proteolytic fragments at each time point. High concentrations of peptide 29, but not 32 (PGD97), was present in the spheroids after either 4 or 24 h of incubation. The heatmaps for three representative fragments are shown in FIG. 8. A degradation fragment (#1) corresponding to proteolytic cleavage between Thr and Arg (FIG. 8b) was observed, but none of the other potential degradation products were observed. These results indicate that PGD97 efficiently entered the cytosol of HCT116 cells and was rapidly reduced by intracellular thiols into peptide 29, which then underwent partial degradation inside the cytosol. Most importantly, significant concentrations of intact peptide 29 was still present inside the cells after 24 h.

Figure 9:
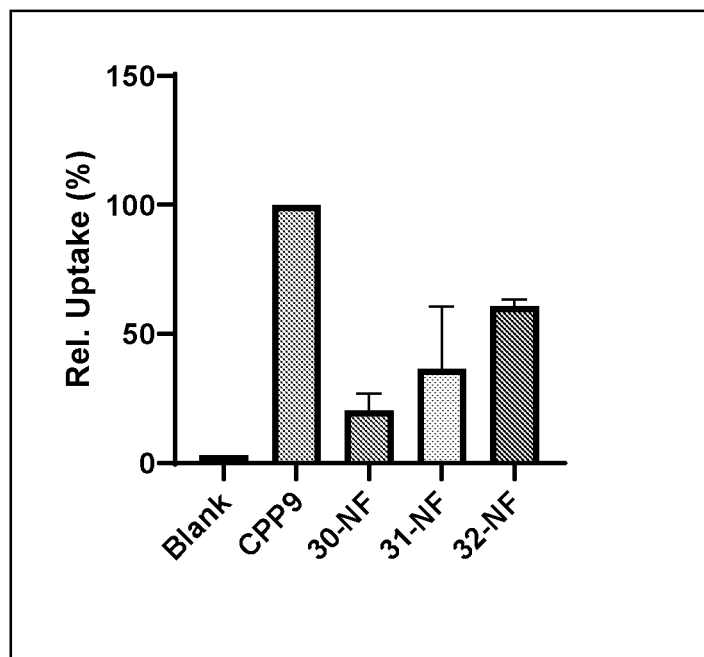
FIG. 9. Relative cytosolic entry efficiency of naphthofluorescein-labeled compounds in HeLa cells (n=3).

Cellular Uptake. HeLa cells were seeded into 12-well cell-culture treated plates at a final density of $15 \times 10^4$ cells/well in DMEM supplemented with 10% FBS and 1% penicillin/streptomycin and incubated overnight at 37° C. and 5% $CO_2$. After 24 h, the media was aspirated followed by washing the cells three times with warm DPBS. Peptides were diluted to a final concentration of 5 μM in DMEM containing 10% FBS with 1% penicillin/streptomycin, added to each well and then incubated for 2 h at 37° C. with 5% $CO_2$. After 2 h, treatment media was aspirated and the cells were washed three times with ice-cold DPBS. Cells were removed from the plate via treatment with trypsin/EDTA and then harvested in ice-cold DPBS followed by centrifugation at 300 g, 4° C. for 5 min. Cells were resuspended in DPBS and quantified using a BD Biosciences LSR II flow cytometer and gated using FlowJo. Values for uptake are provided as a percentage relative to positive control, CPP9 ([cyclo-fΦRrRrQ]-miniPEG-K[NF]), which has a 62% cytosolic entry efficiency. PGD97 entered HeLa cells at 60% efficiency relative to CPP9, corresponding to an absolute cytosolic entry efficiency of ~36% (FIG. 9).

Figure 10:
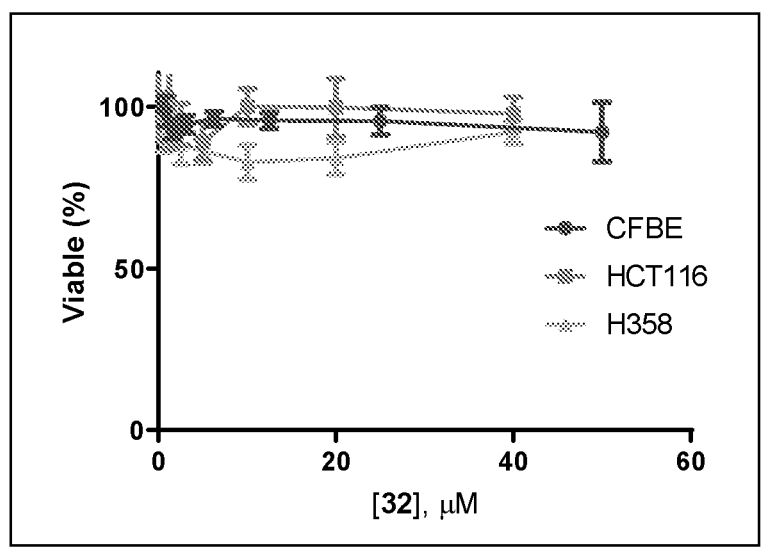
FIG. 10 Effect of PGD97 on the viability of CFBE, HCT116, and H358 cells as determined by MTT assay.

Cytotoxicity. CFBE, HCT116 (colorectal cancer), or H358 (lung cancer) cells were seeded into a 96-well microplate (5000 cells per well) in full growth media and incubated at 37° C. overnight. A serial dilution of PGD97 was prepared in DPBS and then added to each well. The treated cells were incubated at 37° C. with 5% $CO_2$ for 72 h. Following compound treatment, 10 μL of MTT stock solution was added to each well. After an additional 4 h at 37° C., 100 μL of SDS-HCl solubilizing solution was added to each well and the plate was returned to the incubator overnight at 37° C. A Tecan Infinite M1000 Pro microplate reader was used the following morning to measure the absorbance of the formazan product at 565 nm. PGD97 did not significantly reduce the viability of any of the cells at up to 50 μM concentration (FIG. 10).

Effect on ΔF508 CFTR Membrane Expression. HEK-293T cells stably expressing ΔF508CFTR-FAP (Holleran et al. *Mol. Med.* 2012, 18, 685-696) were seeded into poly-L-lysine-coated white-wall, clear bottom 96-well plates (100,000 cells/well) in complete growth medium and incubated for 24 h at 27° C. or 37° C. and 5% $CO_2$. After 24 h, media was aspirated from each well and washed twice with warm DPBS. Compound serial dilutions with or without 10 μM VX809 were added to each well in fresh penicillin/streptomycin-free media containing 10% FBS and incubated at 27° C. or 37° C. in 5% $CO_2$ for 24 h. After 24 h, the media was aspirated and each well was washed 3× with warm DPBS. 500 nM MG-B-Tau and 500 nM Hoechst 33342 was added in DPBS and MG-B-Tau fluorescence was immediately measured on a TECAN Infinite M1000 plate reader (excitation=640 nm, emission=680 nm, 10 nm bandwidth, 16 distinct points per well). After measurement, the plate was returned to the incubator at 37° C. for 1 h before quantifying Hoechst 33342 fluorescence on a TECAN Infinite M1000 plate reader (excitation=362 nm, emission=492 nm, 5 nm bandwidth, identical points per well as measured for MG-B-Tau). Cell-count normalized fluorescent intensity was determined by dividing the per-well MG-B-Tau intensity by Hoechst intensity and then plotted relative to untreated control using GraphPad PRISM ver. 7.0.

Figure 11:
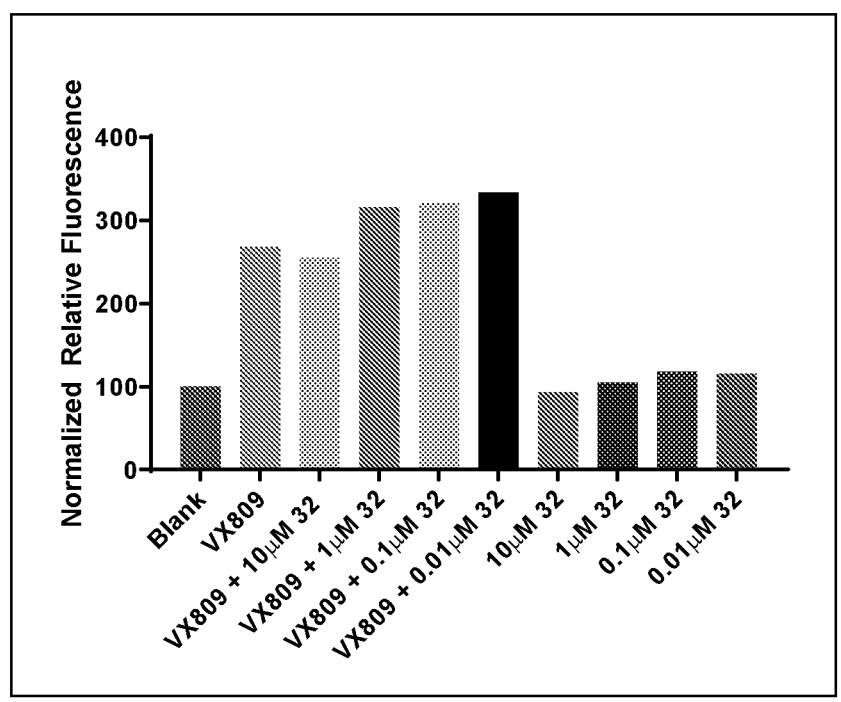
FIG. 11 Effect of PGD97 alone or in combination with VX809 on CFTR surface expression of ΔF508CFTR at 27° C. as determined by the FAP assay.

PGD97 alone slightly increased the cell surface expression of ΔF508CFTR-FAP at 27° C. Combination of PGD97 and Vertex corrector VX809 led to further increase in cell surface expression and the magnitude of increase was greater than PGD97 alone (FIG. 11). Interestingly, increased expression was observed at lower PGD97 concentrations (10-1000 nM), whereas 10 μM PGD97 reduced its surface expression. This may be due to inhibition of both CAL and NHERF PDZ domains at higher concentration; inhibition of NHERF PDZ domains would inhibit the trafficking of CFTR to the cell surface.

Figure 12:
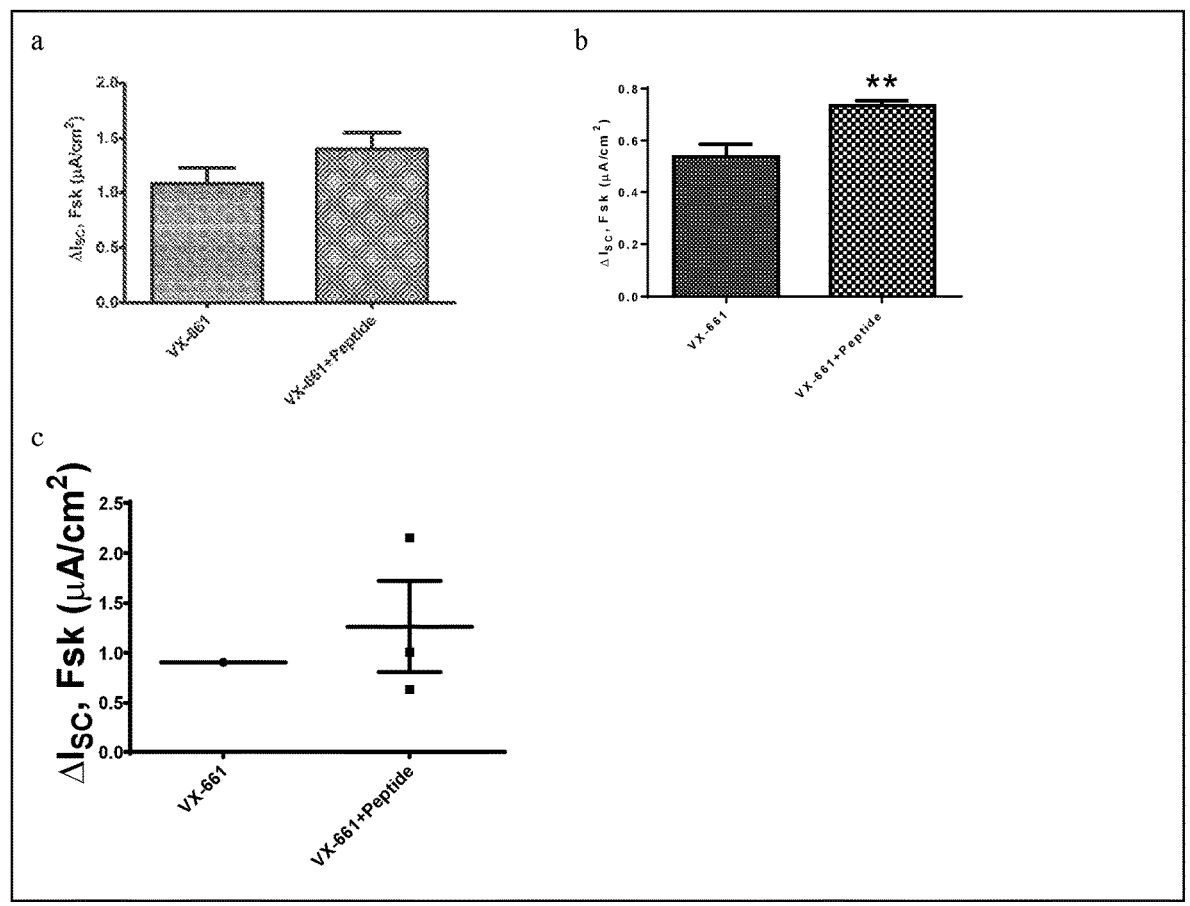
FIG. 12 (*a*) Short-circuit current measured following treatment with VX661 (10 μM) and/or PGD97 (100 nM) in CFBE cells after 4 h (n=4).

Effect on Ion Channel Activity. CFBE or patient-derived primary cells were seeded onto filter inserts and grown to confluence at 37° C. in complete growth medium containing 10% FBS and 1% penicillin/streptomycin. Once confluent, cells were gently washed with DPBS and 10 μM VX661 and/or 100 nM PGD97 were added in complete growth medium supplemented with 10% FBS and 1% penicillin/streptomycin for 4 h or 24 h at 37° C. before measuring short circuit current using an Ussing chamber. PGD97 improved the ion channel activity by 33% and 37% relative to VX661 only controls after 4 and 24 h, respectively (FIG. 12a,b). It also significantly increased the ion channel activity in patient-derived primary cells (FIG. 12c).

Figure 13:
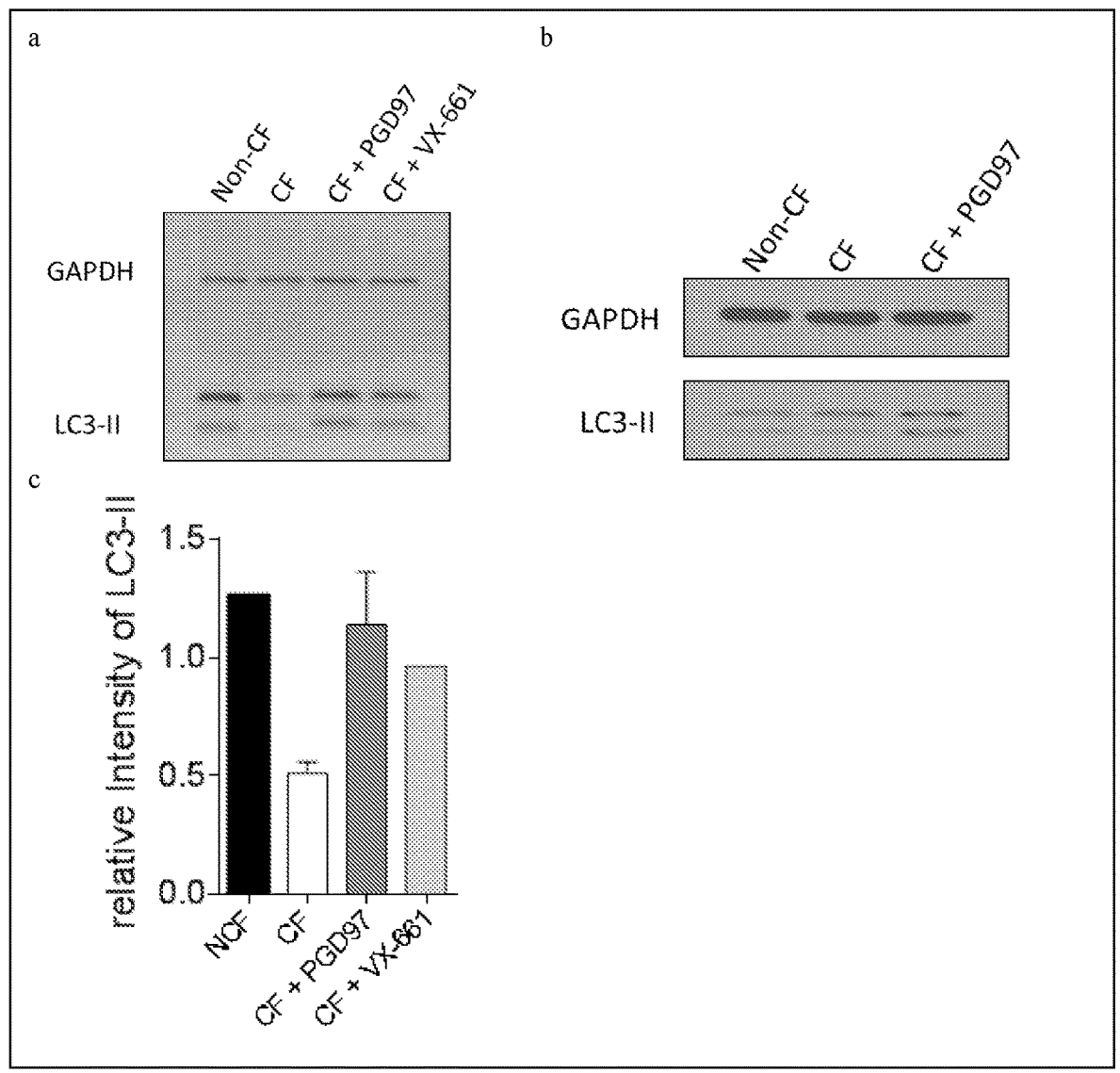
FIG. 13 Effect of PGD97 (100 nM) and VX661 (10 μM) on LC3-II levels in human ΔF508 CFTR macrophages derived from two patients.

Effect on Autophagy in Macrophage. Human primary ΔF508 CFTR macrophages were incubated with 10 μM VX809 (n=1) or 100 nM PGD97 (n=2) for 48 h in complete growth medium supplemented with 10% FBS and 1% penicillin/streptomycin at 37° C. Induction of autophagy was determined via western blotting for autophagy-associated protein LC3-II. As shown in FIG. 13, treatment with 100 nM PGD97 increased the LC3-II protein levels to nearly WT level. VX661 at 10 μM was also effective.

The invention claimed is:

1. A peptide having a structure according to Formula I:

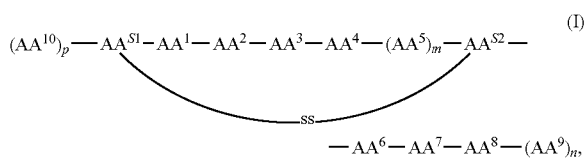

or a pharmaceutically acceptable salt thereof,
wherein:
$AA^1$, $AA^2$, $AA^3$, $AA^4$, $AA^5$, $AA^6$, $AA^7$, $AA^8$, $AA^9$, and $AA^{10}$ are independently selected from an amino acid, which is optionally substituted with one or more substituents;
m is 0 or 1;
n is a number in the range of from 0 to 10;
p is a number in the range of from 0 to 10;
each of $AA^{S1}$ and $AA^{S2}$ is independently an amino acid which forms a disulfide bond (ss);
two or three of $AA^1$, $AA^2$, $AA^3$, $AA^4$ and $A^5$ are arginine; and
two or three of $AA^1$, $AA^2$, $AA^3$, $AA^4$ and $A^5$ are each independently phenylalanine, naphthylalanine, tryptophan, 3-(3-benzothienyl)-alanine or proline;
$-AA^6-AA^7-AA^8-(AA^9)_n$ is a peptide sequence which binds to the CAL-PDZ domain is selected from SEQ ID NO: 109, 110, 111, 112, 113, 114, 115, 116, 117, 118, and 119.

2. The peptide of claim 1, comprising from 1 to 4 D-arginines.

3. The peptide of claim 1, wherein:
in Formula I:
when p is 1 to 10, the N-terminus of AA is C(O)-alkyl, —C(O)-carbocyclyl, —C(O)-aryl, —C(O)-heteroaryl, or —N(=S)N—$R^aR^b$, wherein $R^a$ and $R^b$ are independently selected from hydrogen, alkyl, carbocyclyl, aryl, and heteroaryl.

4. The peptide of claim 1, wherein each of $AA^{S1}$ and $AA^{S2}$ is:

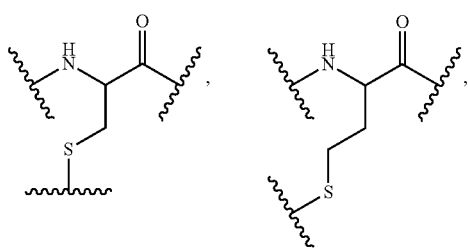

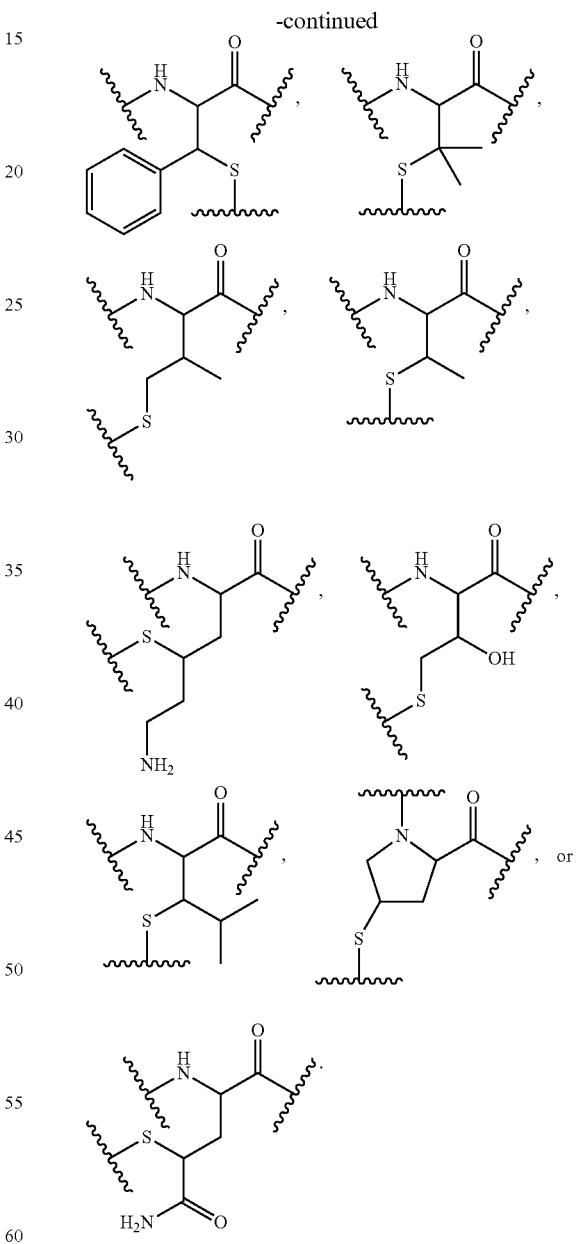

5. A pharmaceutical composition comprising the peptide of claim 1.

6. A method of treating cystic fibrosis in a patient in need thereof, comprising administering a peptide of claim 1 to the patient.

7. A peptide having the following structure:
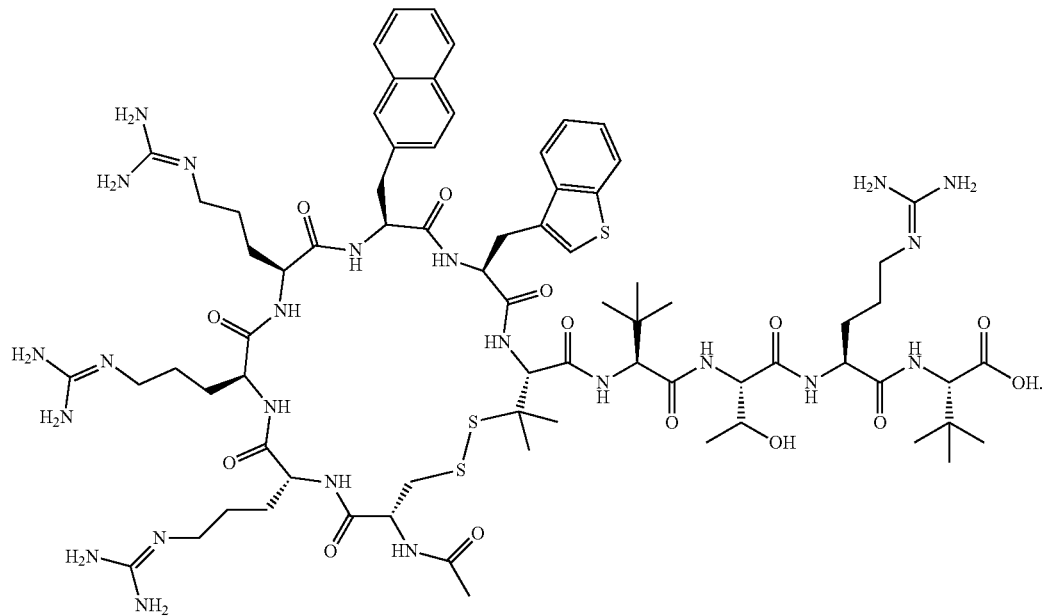
8. A peptide having the following structure:
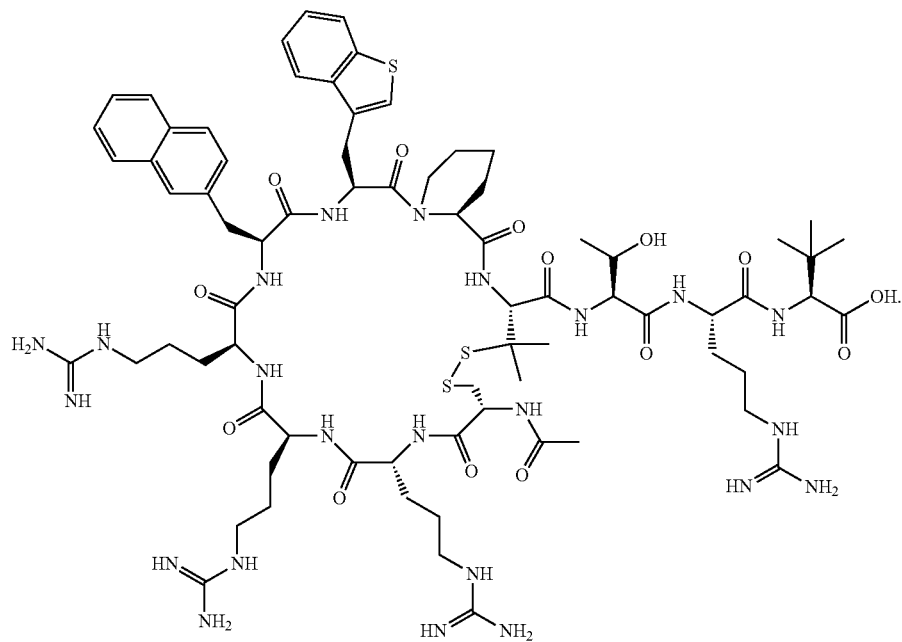 [SMILES: CC(=O)N[C@H]1CSSC(C)(C)[C@@H](C(=O)N[C@H](C(=O)N[C@@H](CCCNC(=N)N)C(=O)N[C@H](C(=O)O)C(C)(C)C)C(C)O)NC(=O)[C@@H]2CCCCN2C(=O)[C@H](Cc2csc3ccccc23)NC(=O)[C@H](Cc2ccc3ccccc3c2)NC(=O)[C@H](CCCNC(=N)N)NC(=O)[C@H](CCCNC(=N)N)NC(=O)[C@@H](CCCNC(=N)N)NC1=O]
* * * * *

SEQUENCE LISTING

<160> NUMBER OF SEQ ID NOS: 158

<210> SEQ ID NO 1
<211> LENGTH: 12
<212> TYPE: PRT
<213> ORGANISM: Artificial Sequence

```
<220> FEATURE:
<223> OTHER INFORMATION: synthetic construct

<400> SEQUENCE: 1

Cys Arg Arg Arg Arg Phe Trp Gln Cys Thr Arg Val
1               5                   10

<210> SEQ ID NO 2
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 2

Phe Xaa Arg Arg Arg
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 3

Phe Xaa Arg Arg Arg
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 4

Phe Xaa Arg Arg Arg
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: L-2-naphthylalanine

<400> SEQUENCE: 5

Arg Arg Arg Xaa Phe
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: L-2-naphthylalanine

<400> SEQUENCE: 6

Arg Arg Arg Arg Xaa Phe
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 7

Phe Xaa Arg Arg Arg Arg
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-2-naphthylalanine
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (5)..(5)
<223> OTHER INFORMATION: D-arginine

<400> SEQUENCE: 8

Phe Xaa Xaa Arg Xaa Arg
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-2-naphthylalanine
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (5)..(5)
<223> OTHER INFORMATION: D-arginine
```

```
<400> SEQUENCE: 9

Phe Xaa Xaa Arg Xaa Arg
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 10

Phe Xaa Arg Arg Arg Arg
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 11

Xaa Xaa Arg Xaa Arg Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: L-2-naphthylalanine

<400> SEQUENCE: 12

Arg Arg Phe Arg Xaa Arg
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: L-2-naphthylalanine
```

```
<400> SEQUENCE: 13

Phe Arg Arg Arg Arg Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (5)..(5)
<223> OTHER INFORMATION: L-2-naphthylalanine

<400> SEQUENCE: 14

Xaa Arg Phe Arg Xaa Arg
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: L-2-naphthylalanine

<400> SEQUENCE: 15

Arg Arg Xaa Phe Arg Arg
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic construct

<400> SEQUENCE: 16

Cys Arg Arg Arg Arg Phe Trp
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: L-2-naphthylalanine
<220> FEATURE:
<221> NAME/KEY: MISC_FEATURE
<222> LOCATION: (5)..(5)
<223> OTHER INFORMATION: D-arginine
<220> FEATURE:
<221> NAME/KEY: MISC_FEATURE
<222> LOCATION: (7)..(7)
<223> OTHER INFORMATION: D-arginine
```

```
<400> SEQUENCE: 17

Phe Xaa Xaa Arg Xaa Arg Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: L-2-naphthylalanine

<400> SEQUENCE: 18

Phe Phe Xaa Arg Arg Arg Arg
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: L-2-naphthylalanine

<400> SEQUENCE: 19

Arg Phe Arg Phe Arg Xaa Arg
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic construct

<400> SEQUENCE: 20

Cys Arg Arg Arg Arg Phe Trp
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 21

Phe Xaa Arg Arg Arg Arg Gln Lys
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic construct
```

```
<220> FEATURE:
<221> NAME/KEY: MISC_FEATURE
<222> LOCATION: (2)..(2)
<223> OTHER INFORMATION: L-2-naphthylalanine

<400> SEQUENCE: 22

Phe Xaa Arg Arg Arg Arg Gln Cys
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 23

Phe Xaa Arg Xaa Arg Xaa Arg
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 24

Phe Xaa Arg Arg Arg Arg Arg
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: L-2-naphthylalanine
<220> FEATURE:
<221> NAME/KEY: MISC_FEATURE
<222> LOCATION: (8)..(8)
<223> OTHER INFORMATION: Norleucine

<400> SEQUENCE: 25

Arg Arg Arg Arg Xaa Phe Asp Xaa Cys
1               5

<210> SEQ ID NO 26
<211> LENGTH: 5
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 26

Phe Xaa Arg Arg Arg
1               5

<210> SEQ ID NO 27
<211> LENGTH: 5
<212> TYPE: PRT
<213> ORGANISM: Artificial Sequence
<220> FEATURE:
<223> OTHER INFORMATION: synthetic construct

<400> SEQUENCE: 27

Phe Trp Arg Arg Arg
1               5

<210> SEQ ID NO 28
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: L-2-naphthylalanine

<400> SEQUENCE: 28

Arg Arg Arg Xaa Phe
1               5

<210> SEQ ID NO 29
<211> LENGTH: 5
<212> TYPE: PRT
<213> ORGANISM: Artificial Sequence
<220> FEATURE:
<223> OTHER INFORMATION: synthetic construct

<400> SEQUENCE: 29

Arg Arg Arg Trp Phe
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 30

Phe Xaa Arg Arg Arg Arg
1               5

<210> SEQ ID NO 31
<211> LENGTH: 5
<212> TYPE: PRT
<213> ORGANISM: Artificial Sequence
<220> FEATURE:
<223> OTHER INFORMATION: synthetic construct
```

```
<400> SEQUENCE: 31

Phe Phe Arg Arg Arg
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (5)..(5)
<223> OTHER INFORMATION: D-arginine

<400> SEQUENCE: 32

Phe Phe Xaa Arg Xaa
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: D-arginine

<400> SEQUENCE: 33

Phe Phe Arg Xaa Arg
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic construct

<400> SEQUENCE: 34

Phe Arg Phe Arg Arg
1               5

<210> SEQ ID NO 35
<211> LENGTH: 5
<212> TYPE: PRT
<213> ORGANISM: Artificial Sequence
<220> FEATURE:
<223> OTHER INFORMATION: synthetic construct

<400> SEQUENCE: 35

Phe Arg Arg Phe Arg
1               5

<210> SEQ ID NO 36
<211> LENGTH: 5
<212> TYPE: PRT
<213> ORGANISM: Artificial Sequence
<220> FEATURE:
<223> OTHER INFORMATION: synthetic construct
```

```
<400> SEQUENCE: 36

Phe Arg Arg Arg Phe
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 37

Gly Xaa Arg Arg Arg
1               5

<210> SEQ ID NO 38
<211> LENGTH: 5
<212> TYPE: PRT
<213> ORGANISM: Artificial Sequence
<220> FEATURE:
<223> OTHER INFORMATION: synthetic construct

<400> SEQUENCE: 38

Phe Phe Phe Arg Ala
1               5

<210> SEQ ID NO 39
<211> LENGTH: 5
<212> TYPE: PRT
<213> ORGANISM: Artificial Sequence
<220> FEATURE:
<223> OTHER INFORMATION: synthetic construct

<400> SEQUENCE: 39

Phe Phe Phe Arg Arg
1               5

<210> SEQ ID NO 40
<211> LENGTH: 6
<212> TYPE: PRT
<213> ORGANISM: Artificial Sequence
<220> FEATURE:
<223> OTHER INFORMATION: synthetic construct

<400> SEQUENCE: 40

Phe Phe Arg Arg Arg Arg
1               5

<210> SEQ ID NO 41
<211> LENGTH: 6
<212> TYPE: PRT
<213> ORGANISM: Artificial Sequence
<220> FEATURE:
<223> OTHER INFORMATION: synthetic construct

<400> SEQUENCE: 41

Phe Arg Arg Phe Arg Arg
1               5

<210> SEQ ID NO 42
<211> LENGTH: 6
<212> TYPE: PRT
<213> ORGANISM: Artificial Sequence
```

```
<220> FEATURE:
<223> OTHER INFORMATION: synthetic construct

<400> SEQUENCE: 42

Phe Arg Arg Arg Phe Arg
1               5

<210> SEQ ID NO 43
<211> LENGTH: 6
<212> TYPE: PRT
<213> ORGANISM: Artificial Sequence
<220> FEATURE:
<223> OTHER INFORMATION: synthetic construct

<400> SEQUENCE: 43

Arg Phe Phe Arg Arg Arg
1               5

<210> SEQ ID NO 44
<211> LENGTH: 6
<212> TYPE: PRT
<213> ORGANISM: Artificial Sequence
<220> FEATURE:
<223> OTHER INFORMATION: synthetic construct

<400> SEQUENCE: 44

Arg Phe Arg Arg Phe Arg
1               5

<210> SEQ ID NO 45
<211> LENGTH: 6
<212> TYPE: PRT
<213> ORGANISM: Artificial Sequence
<220> FEATURE:
<223> OTHER INFORMATION: synthetic construct

<400> SEQUENCE: 45

Phe Arg Phe Arg Arg Arg
1               5

<210> SEQ ID NO 46
<211> LENGTH: 6
<212> TYPE: PRT
<213> ORGANISM: Artificial Sequence
<220> FEATURE:
<223> OTHER INFORMATION: synthetic construct

<400> SEQUENCE: 46

Phe Phe Phe Arg Arg Arg
1               5

<210> SEQ ID NO 47
<211> LENGTH: 6
<212> TYPE: PRT
<213> ORGANISM: Artificial Sequence
<220> FEATURE:
<223> OTHER INFORMATION: synthetic construct

<400> SEQUENCE: 47

Phe Phe Arg Arg Arg Phe
1               5

<210> SEQ ID NO 48
<211> LENGTH: 6
<212> TYPE: PRT
<213> ORGANISM: Artificial Sequence
```

```
<220> FEATURE:
<223> OTHER INFORMATION: synthetic construct

<400> SEQUENCE: 48

Phe Arg Phe Phe Arg Arg
1               5

<210> SEQ ID NO 49
<211> LENGTH: 6
<212> TYPE: PRT
<213> ORGANISM: Artificial Sequence
<220> FEATURE:
<223> OTHER INFORMATION: synthetic construct

<400> SEQUENCE: 49

Arg Arg Phe Phe Phe Arg
1               5

<210> SEQ ID NO 50
<211> LENGTH: 6
<212> TYPE: PRT
<213> ORGANISM: Artificial Sequence
<220> FEATURE:
<223> OTHER INFORMATION: synthetic construct

<400> SEQUENCE: 50

Phe Phe Arg Phe Arg Arg
1               5

<210> SEQ ID NO 51
<211> LENGTH: 6
<212> TYPE: PRT
<213> ORGANISM: Artificial Sequence
<220> FEATURE:
<223> OTHER INFORMATION: synthetic construct

<400> SEQUENCE: 51

Phe Phe Arg Arg Phe Arg
1               5

<210> SEQ ID NO 52
<211> LENGTH: 6
<212> TYPE: PRT
<213> ORGANISM: Artificial Sequence
<220> FEATURE:
<223> OTHER INFORMATION: synthetic construct

<400> SEQUENCE: 52

Phe Arg Arg Phe Phe Arg
1               5

<210> SEQ ID NO 53
<211> LENGTH: 6
<212> TYPE: PRT
<213> ORGANISM: Artificial Sequence
<220> FEATURE:
<223> OTHER INFORMATION: synthetic construct

<400> SEQUENCE: 53

Phe Arg Arg Phe Arg Phe
1               5

<210> SEQ ID NO 54
<211> LENGTH: 6
<212> TYPE: PRT
<213> ORGANISM: Artificial Sequence
```

```
<220> FEATURE:
<223> OTHER INFORMATION: synthetic construct

<400> SEQUENCE: 54

Phe Arg Phe Arg Phe Arg
1               5

<210> SEQ ID NO 55
<211> LENGTH: 6
<212> TYPE: PRT
<213> ORGANISM: Artificial Sequence
<220> FEATURE:
<223> OTHER INFORMATION: synthetic construct

<400> SEQUENCE: 55

Arg Phe Phe Arg Phe Arg
1               5

<210> SEQ ID NO 56
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 56

Gly Xaa Arg Arg Arg Arg
1               5

<210> SEQ ID NO 57
<211> LENGTH: 7
<212> TYPE: PRT
<213> ORGANISM: Artificial Sequence
<220> FEATURE:
<223> OTHER INFORMATION: synthetic construct

<400> SEQUENCE: 57

Phe Phe Phe Arg Arg Arg Arg
1               5

<210> SEQ ID NO 58
<211> LENGTH: 7
<212> TYPE: PRT
<213> ORGANISM: Artificial Sequence
<220> FEATURE:
<223> OTHER INFORMATION: synthetic construct

<400> SEQUENCE: 58

Arg Phe Phe Arg Arg Arg Arg
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic construct

<400> SEQUENCE: 59

Arg Arg Phe Phe Arg Arg Arg
1               5
```

```
<210> SEQ ID NO 60
<211> LENGTH: 7
<212> TYPE: PRT
<213> ORGANISM: Artificial Sequence
<220> FEATURE:
<223> OTHER INFORMATION: synthetic construct

<400> SEQUENCE: 60

Arg Phe Phe Phe Arg Arg Arg
1               5

<210> SEQ ID NO 61
<211> LENGTH: 7
<212> TYPE: PRT
<213> ORGANISM: Artificial Sequence
<220> FEATURE:
<223> OTHER INFORMATION: synthetic construct

<400> SEQUENCE: 61

Arg Arg Phe Phe Phe Arg Arg
1               5

<210> SEQ ID NO 62
<211> LENGTH: 7
<212> TYPE: PRT
<213> ORGANISM: Artificial Sequence
<220> FEATURE:
<223> OTHER INFORMATION: synthetic construct

<400> SEQUENCE: 62

Phe Phe Arg Arg Phe Arg Arg
1               5

<210> SEQ ID NO 63
<211> LENGTH: 7
<212> TYPE: PRT
<213> ORGANISM: Artificial Sequence
<220> FEATURE:
<223> OTHER INFORMATION: synthetic construct

<400> SEQUENCE: 63

Phe Phe Arg Arg Arg Arg Phe
1               5

<210> SEQ ID NO 64
<211> LENGTH: 7
<212> TYPE: PRT
<213> ORGANISM: Artificial Sequence
<220> FEATURE:
<223> OTHER INFORMATION: synthetic construct

<400> SEQUENCE: 64

Phe Arg Arg Phe Phe Arg Arg
1               5

<210> SEQ ID NO 65
<211> LENGTH: 8
<212> TYPE: PRT
<213> ORGANISM: Artificial Sequence
<220> FEATURE:
<223> OTHER INFORMATION: synthetic construct

<400> SEQUENCE: 65

Phe Phe Phe Arg Arg Arg Arg Arg
1               5
```

```
<210> SEQ ID NO 66
<211> LENGTH: 9
<212> TYPE: PRT
<213> ORGANISM: Artificial Sequence
<220> FEATURE:
<223> OTHER INFORMATION: synthetic construct

<400> SEQUENCE: 66

Phe Phe Phe Arg Arg Arg Arg Arg Arg
1               5

<210> SEQ ID NO 67
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 67

Phe Xaa Arg Xaa Arg Xaa
1               5

<210> SEQ ID NO 68
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 68

Xaa Xaa Arg Arg Arg Arg
1               5

<210> SEQ ID NO 69
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-Phenylalanine
<220> FEATURE:
<221> NAME/KEY: MISC_FEATURE
<222> LOCATION: (5)..(5)
<223> OTHER INFORMATION: D-arginine

<400> SEQUENCE: 69

Phe Xaa Phe Arg Xaa Arg
1               5
```

```
<210> SEQ ID NO 70
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (3)..(3)
<223> OTHER INFORMATION: D-Phenylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 70

Xaa Phe Xaa Xaa Arg Xaa
1               5

<210> SEQ ID NO 71
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (3)..(3)
<223> OTHER INFORMATION: D-Phenylalanine
<220> FEATURE:
<221> NAME/KEY: MISC_FEATURE
<222> LOCATION: (5)..(5)
<223> OTHER INFORMATION: D-arginine

<400> SEQUENCE: 71

Xaa Phe Xaa Arg Xaa Arg
1               5

<210> SEQ ID NO 72
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-Phenylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 72

Phe Xaa Phe Xaa Arg Xaa
1               5
```

-continued

```
<210> SEQ ID NO 73
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (3)..(3)
<223> OTHER INFORMATION: D-2-naphthylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 73

Xaa Phe Xaa Xaa Arg Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (3)..(3)
<223> OTHER INFORMATION: D-Phenylalanine
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 74

Xaa Xaa Xaa Xaa Arg Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-2-naphthylalanine
<220> FEATURE:
<221> NAME/KEY: MISC_FEATURE
<222> LOCATION: (3)..(3)
<223> OTHER INFORMATION: D-Phenylalanine
```

```
<220> FEATURE:
<221> NAME/KEY: MISC_FEATURE
<222> LOCATION: (4)..(4)
<223> OTHER INFORMATION: D-arginine
<220> FEATURE:
<221> NAME/KEY: MISC_FEATURE
<222> LOCATION: (6)..(6)
<223> OTHER INFORMATION: D-arginine

<400> SEQUENCE: 75

Xaa Phe Xaa Xaa Arg Xaa
1               5

<210> SEQ ID NO 76
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (5)..(5)
<223> OTHER INFORMATION: D-arginine

<400> SEQUENCE: 76

Phe Xaa Xaa Arg Xaa
1               5

<210> SEQ ID NO 77
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (5)..(5)
<223> OTHER INFORMATION: D-arginine

<400> SEQUENCE: 77

Xaa Xaa Xaa Arg Xaa
1               5

<210> SEQ ID NO 78
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-Phenylalanine
```

```
<220> FEATURE:
<221> NAME/KEY: MISC_FEATURE
<222> LOCATION: (5)..(5)
<223> OTHER INFORMATION: D-arginine
<220> FEATURE:
<221> NAME/KEY: MISC_FEATURE
<222> LOCATION: (7)..(7)
<223> OTHER INFORMATION: D-arginine

<400> SEQUENCE: 78

Lys Xaa Phe Arg Xaa Arg Xaa Asp
1               5

<210> SEQ ID NO 79
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-2,3-diaminopropionic acid
<220> FEATURE:
<221> NAME/KEY: MISC_FEATURE
<222> LOCATION: (2)..(2)
<223> OTHER INFORMATION: D-Phenylalanine
<220> FEATURE:
<221> NAME/KEY: MISC_FEATURE
<222> LOCATION: (5)..(5)
<223> OTHER INFORMATION: D-arginine
<220> FEATURE:
<221> NAME/KEY: MISC_FEATURE
<222> LOCATION: (7)..(7)
<223> OTHER INFORMATION: D-arginine

<400> SEQUENCE: 79

Xaa Xaa Phe Arg Xaa Arg Xaa Asp
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
<220> FEATURE:
<221> NAME/KEY: MISC_FEATURE
<222> LOCATION: (5)..(6)
<223> OTHER INFORMATION: D-arginine

<400> SEQUENCE: 80

Xaa Xaa Arg Glu Xaa Xaa
1               5

<210> SEQ ID NO 81
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
```

```
<220> FEATURE:
<221> NAME/KEY: MISC_FEATURE
<222> LOCATION: (2)..(2)
<223> OTHER INFORMATION: Napthylalanine
<220> FEATURE:
<221> NAME/KEY: MISC_FEATURE
<222> LOCATION: (5)..(6)
<223> OTHER INFORMATION: D-arginine

<400> SEQUENCE: 81

Xaa Xaa Arg Arg Xaa Xaa
1               5

<210> SEQ ID NO 82
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(3)
<223> OTHER INFORMATION: Napthylalanine
<220> FEATURE:
<221> NAME/KEY: MISC_FEATURE
<222> LOCATION: (5)..(6)
<223> OTHER INFORMATION: D-arginine

<400> SEQUENCE: 82

Xaa Xaa Xaa Arg Xaa Xaa
1               5

<210> SEQ ID NO 83
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(3)
<223> OTHER INFORMATION: Napthylalanine
<220> FEATURE:
<221> NAME/KEY: MISC_FEATURE
<222> LOCATION: (5)..(6)
<223> OTHER INFORMATION: D-arginine

<400> SEQUENCE: 83

Xaa Xaa Xaa Arg Xaa Xaa
1               5

<210> SEQ ID NO 84
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
```

```
<220> FEATURE:
<221> NAME/KEY: MISC_FEATURE
<222> LOCATION: (5)..(6)
<223> OTHER INFORMATION: D-arginine

<400> SEQUENCE: 84

Xaa Xaa Phe Arg Xaa Xaa
1               5

<210> SEQ ID NO 85
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
<220> FEATURE:
<221> NAME/KEY: MISC_FEATURE
<222> LOCATION: (5)..(6)
<223> OTHER INFORMATION: D-arginine

<400> SEQUENCE: 85

Xaa Xaa Phe Arg Xaa Xaa
1               5

<210> SEQ ID NO 86
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
<220> FEATURE:
<221> NAME/KEY: MISC_FEATURE
<222> LOCATION: (3)..(3)
<223> OTHER INFORMATION: D-Phenylalanine
<220> FEATURE:
<221> NAME/KEY: MISC_FEATURE
<222> LOCATION: (5)..(6)
<223> OTHER INFORMATION: D-arginine

<400> SEQUENCE: 86

Xaa Xaa Xaa Arg Xaa Xaa
1               5

<210> SEQ ID NO 87
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
```

```
<220> FEATURE:
<221> NAME/KEY: MISC_FEATURE
<222> LOCATION: (3)..(3)
<223> OTHER INFORMATION: D-Phenylalanine
<220> FEATURE:
<221> NAME/KEY: MISC_FEATURE
<222> LOCATION: (5)..(6)
<223> OTHER INFORMATION: D-arginine

<400> SEQUENCE: 87

Xaa Xaa Xaa Arg Xaa Xaa
1               5

<210> SEQ ID NO 88
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (13)..(13)
<223> OTHER INFORMATION: D-Proline

<400> SEQUENCE: 88

Arg Val Arg Thr Arg Gly Lys Arg Arg Ile Arg Arg Xaa Pro
1               5                   10

<210> SEQ ID NO 89
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (13)..(13)
<223> OTHER INFORMATION: D-Proline

<400> SEQUENCE: 89

Arg Thr Arg Thr Arg Gly Lys Arg Arg Ile Arg Val Xaa Pro
1               5                   10

<210> SEQ ID NO 90
<211> LENGTH: 8
<212> TYPE: PRT
<213> ORGANISM: Artificial Sequence
<220> FEATURE:
<223> OTHER INFORMATION: synthetic construct

<400> SEQUENCE: 90

Trp Arg Trp Arg Trp Arg Trp Arg
1               5

<210> SEQ ID NO 91
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: dodecanoyl

<400> SEQUENCE: 91

Lys Xaa Arg Arg Arg Arg
1               5
```

```
<210> SEQ ID NO 92
<211> LENGTH: 8
<212> TYPE: PRT
<213> ORGANISM: Artificial Sequence
<220> FEATURE:
<223> OTHER INFORMATION: synthetic construct

<400> SEQUENCE: 92

Cys Arg Cys Arg Cys Arg Cys Arg
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(4)
<223> OTHER INFORMATION: 2,3-diaminopropionic acid
<220> FEATURE:
<221> NAME/KEY: MISC_FEATURE
<222> LOCATION: (5)..(5)
<223> OTHER INFORMATION: D- Phenylalanine
<220> FEATURE:
<221> NAME/KEY: MISC_FEATURE
<222> LOCATION: (7)..(8)
<223> OTHER INFORMATION: 2,3-diaminopropionic acid

<400> SEQUENCE: 93

Thr Xaa Xaa Xaa Xaa Leu Xaa Xaa Thr
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-amino-3-guanidinylpropionic acid
<220> FEATURE:
<221> NAME/KEY: MISC_FEATURE
<222> LOCATION: (3)..(3)
<223> OTHER INFORMATION: 2,3-diaminopropionic acid
<220> FEATURE:
<221> NAME/KEY: MISC_FEATURE
<222> LOCATION: (4)..(4)
<223> OTHER INFORMATION: L-2-amino-3-guanidinylpropionic acid
<220> FEATURE:
<221> NAME/KEY: MISC_FEATURE
<222> LOCATION: (5)..(5)
<223> OTHER INFORMATION: D- Phenylalanine
<220> FEATURE:
<221> NAME/KEY: MISC_FEATURE
<222> LOCATION: (7)..(8)
<223> OTHER INFORMATION: L-2-amino-3-guanidinylpropionic acid

<400> SEQUENCE: 94

Thr Xaa Xaa Xaa Xaa Leu Xaa Xaa Thr
1               5

<210> SEQ ID NO 95
<211> LENGTH: 6
<212> TYPE: PRT
<213> ORGANISM: Artificial Sequence
<220> FEATURE:
<223> OTHER INFORMATION: synthetic construct
```

```
<220> FEATURE:
<221> NAME/KEY: MISC_FEATURE
<222> LOCATION: (2)..(2)
<223> OTHER INFORMATION: L-2-naphthylalanine

<400> SEQUENCE: 95

Phe Xaa Arg Arg Arg Arg
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-Phenylalanine
<220> FEATURE:
<221> NAME/KEY: MISC_FEATURE
<222> LOCATION: (3)..(3)
<223> OTHER INFORMATION: L-2-naphthylalanine
<220> FEATURE:
<221> NAME/KEY: MISC_FEATURE
<222> LOCATION: (5)..(5)
<223> OTHER INFORMATION: D-Arginine
<220> FEATURE:
<221> NAME/KEY: MISC_FEATURE
<222> LOCATION: (7)..(7)
<223> OTHER INFORMATION: D-Arginine

<400> SEQUENCE: 96

Phe Xaa Xaa Arg Xaa Arg Xaa
1               5

<210> SEQ ID NO 97
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (4)..(4)
<223> OTHER INFORMATION: D-Arginine
<220> FEATURE:
<221> NAME/KEY: MISC_FEATURE
<222> LOCATION: (6)..(6)
<223> OTHER INFORMATION: D-Arginine

<400> SEQUENCE: 97

Xaa Xaa Arg Xaa Arg Xaa
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Phenylalanine
```

```
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (4)..(4)
<223> OTHER INFORMATION: D-Arginine
<220> FEATURE:
<221> NAME/KEY: MISC_FEATURE
<222> LOCATION: (6)..(6)
<223> OTHER INFORMATION: D-Arginine

<400> SEQUENCE: 98

Xaa Xaa Arg Xaa Arg Xaa Arg
1               5

<210> SEQ ID NO 99
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (3)..(3)
<223> OTHER INFORMATION: D-Arginine
<220> FEATURE:
<221> NAME/KEY: MISC_FEATURE
<222> LOCATION: (5)..(5)
<223> OTHER INFORMATION: D-Arginine

<400> SEQUENCE: 99

Phe Xaa Xaa Arg Xaa Arg
1               5

<210> SEQ ID NO 100
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine
<220> FEATURE:
<221> NAME/KEY: MISC_FEATURE
<222> LOCATION: (3)..(3)
<223> OTHER INFORMATION: D-Arginine
<220> FEATURE:
<221> NAME/KEY: MISC_FEATURE
<222> LOCATION: (5)..(5)
<223> OTHER INFORMATION: D-Arginine

<400> SEQUENCE: 100

Phe Xaa Xaa Arg Xaa Arg
1               5

<210> SEQ ID NO 101
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine
```

```
<400> SEQUENCE: 101

Phe Xaa Arg Arg Arg Arg
1               5

<210> SEQ ID NO 102
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: L-2-naphthylalanine

<400> SEQUENCE: 102

Arg Arg Phe Arg Xaa Arg
1               5

<210> SEQ ID NO 103
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: L-2-naphthylalanine

<400> SEQUENCE: 103

Phe Phe Xaa Arg Arg Arg Arg
1               5

<210> SEQ ID NO 104
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: L-2-naphthylalanine

<400> SEQUENCE: 104

Arg Phe Arg Phe Arg Xaa Arg
1               5

<210> SEQ ID NO 105
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: L-2-naphthylalanine

<400> SEQUENCE: 105

Phe Xaa Arg Arg Arg
1               5

<210> SEQ ID NO 106
<211> LENGTH: 6
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: L-2-naphthylalanine

<400> SEQUENCE: 106

Phe Arg Arg Arg Arg Xaa
1               5

<210> SEQ ID NO 107
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-Arginine
<220> FEATURE:
<221> NAME/KEY: MISC_FEATURE
<222> LOCATION: (5)..(5)
<223> OTHER INFORMATION: L-2-naphthylalanine

<400> SEQUENCE: 107

Xaa Arg Phe Arg Xaa Arg
1               5

<210> SEQ ID NO 108
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: L-2-naphthylalanine

<400> SEQUENCE: 108

Arg Arg Xaa Phe Arg Arg
1               5

<210> SEQ ID NO 109
<211> LENGTH: 6
<212> TYPE: PRT
<213> ORGANISM: Artificial Sequence
<220> FEATURE:
<223> OTHER INFORMATION: synthetic construct

<400> SEQUENCE: 109

Trp Gln Val Thr Arg Val
1               5

<210> SEQ ID NO 110
<211> LENGTH: 6
<212> TYPE: PRT
<213> ORGANISM: Artificial Sequence
<220> FEATURE:
<223> OTHER INFORMATION: synthetic construct

<400> SEQUENCE: 110

Trp Gln Phe Thr Arg Leu
1               5
```

```
<210> SEQ ID NO 111
<211> LENGTH: 6
<212> TYPE: PRT
<213> ORGANISM: Artificial Sequence
<220> FEATURE:
<223> OTHER INFORMATION: synthetic construct

<400> SEQUENCE: 111

Trp Gln Lys Thr Arg Leu
1               5

<210> SEQ ID NO 112
<211> LENGTH: 6
<212> TYPE: PRT
<213> ORGANISM: Artificial Sequence
<220> FEATURE:
<223> OTHER INFORMATION: synthetic construct

<400> SEQUENCE: 112

Trp Gln Arg Thr Arg Leu
1               5

<210> SEQ ID NO 113
<211> LENGTH: 6
<212> TYPE: PRT
<213> ORGANISM: Artificial Sequence
<220> FEATURE:
<223> OTHER INFORMATION: synthetic construct

<400> SEQUENCE: 113

Trp Gln Lys Thr Arg Ile
1               5

<210> SEQ ID NO 114
<211> LENGTH: 6
<212> TYPE: PRT
<213> ORGANISM: Artificial Sequence
<220> FEATURE:
<223> OTHER INFORMATION: synthetic construct

<400> SEQUENCE: 114

Trp Gln Lys Thr Arg Val
1               5

<210> SEQ ID NO 115
<211> LENGTH: 6
<212> TYPE: PRT
<213> ORGANISM: Artificial Sequence
<220> FEATURE:
<223> OTHER INFORMATION: synthetic construct

<400> SEQUENCE: 115

Trp Gln Phe Thr Lys Leu
1               5

<210> SEQ ID NO 116
<211> LENGTH: 6
<212> TYPE: PRT
<213> ORGANISM: Artificial Sequence
<220> FEATURE:
<223> OTHER INFORMATION: synthetic construct

<400> SEQUENCE: 116

Trp Gln Arg Thr Arg Ile
1               5
```

```
<210> SEQ ID NO 117
<211> LENGTH: 6
<212> TYPE: PRT
<213> ORGANISM: Artificial Sequence
<220> FEATURE:
<223> OTHER INFORMATION: synthetic construct

<400> SEQUENCE: 117

Trp Gln Leu Thr Lys Leu
1               5

<210> SEQ ID NO 118
<211> LENGTH: 6
<212> TYPE: PRT
<213> ORGANISM: Artificial Sequence
<220> FEATURE:
<223> OTHER INFORMATION: synthetic construct

<400> SEQUENCE: 118

Trp Gln Lys Thr Lys Leu
1               5

<210> SEQ ID NO 119
<211> LENGTH: 6
<212> TYPE: PRT
<213> ORGANISM: Artificial Sequence
<220> FEATURE:
<223> OTHER INFORMATION: synthetic construct

<400> SEQUENCE: 119

Trp Gln Arg Thr Arg Val
1               5

<210> SEQ ID NO 120
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: tert-butyl-L-alanine
<220> FEATURE:
<221> NAME/KEY: MISC_FEATURE
<222> LOCATION: (4)..(4)
<223> OTHER INFORMATION: tert-butyl-L-alanine

<400> SEQUENCE: 120

Xaa Thr Arg Xaa
1

<210> SEQ ID NO 121
<211> LENGTH: 9
<212> TYPE: PRT
<213> ORGANISM: Artificial Sequence
<220> FEATURE:
<223> OTHER INFORMATION: synthetic construct

<400> SEQUENCE: 121

Arg Arg Phe Trp Gln Cys Thr Arg Val
1               5

<210> SEQ ID NO 122
<211> LENGTH: 9
<212> TYPE: PRT
<213> ORGANISM: Artificial Sequence
<220> FEATURE:
<223> OTHER INFORMATION: synthetic construct
```

```
<400> SEQUENCE: 122

Arg Arg Phe Trp Gln Cys Thr Arg Ile
1               5

<210> SEQ ID NO 123
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (9)..(9)
<223> OTHER INFORMATION: L-3-cyclohexyl-alanine

<400> SEQUENCE: 123

Arg Arg Phe Trp Gln Cys Thr Arg Xaa
1               5

<210> SEQ ID NO 124
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (11)..(11)
<223> OTHER INFORMATION: alpha-methyl-L-leucine

<400> SEQUENCE: 124

Cys Arg Arg Arg Phe Trp Gln Cys Thr Arg Xaa
1               5                   10

<210> SEQ ID NO 125
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (9)..(9)
<223> OTHER INFORMATION: tert-butyl-L-alanine

<400> SEQUENCE: 125

Arg Arg Phe Trp Gln Cys Thr Arg Xaa
1               5

<210> SEQ ID NO 126
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (11)..(11)
<223> OTHER INFORMATION: tert-butyl-L-alanine

<400> SEQUENCE: 126

Cys Arg Arg Arg Phe Trp Gln Cys Thr Arg Xaa
1               5                   10

<210> SEQ ID NO 127
<211> LENGTH: 9
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<222> LOCATION: (9)..(9)
<223> OTHER INFORMATION: tert-butyl-L-alanine

<400> SEQUENCE: 127

Arg Arg Phe Trp Gln Cys Thr Leu Xaa
1               5

<210> SEQ ID NO 128
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: Nicotinyl-L-lysine
<220> FEATURE:
<221> NAME/KEY: MISC_FEATURE
<222> LOCATION: (9)..(9)
<223> OTHER INFORMATION: tert-butyl-L-alanine

<400> SEQUENCE: 128

Arg Arg Phe Trp Gln Cys Thr Xaa Xaa
1               5

<210> SEQ ID NO 129
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: Trifluoroacetyl-L-Lysine
<220> FEATURE:
<221> NAME/KEY: MISC_FEATURE
<222> LOCATION: (9)..(9)
<223> OTHER INFORMATION: tert-butyl-L-alanine

<400> SEQUENCE: 129

Arg Arg Phe Trp Gln Cys Thr Xaa Xaa
1               5

<210> SEQ ID NO 130
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: L-homoarginine
<220> FEATURE:
<221> NAME/KEY: MISC_FEATURE
<222> LOCATION: (9)..(9)
<223> OTHER INFORMATION: tert-butyl-L-alanine

<400> SEQUENCE: 130

Arg Arg Phe Trp Gln Cys Thr Xaa Xaa
1               5
```

```
<210> SEQ ID NO 131
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: D-proline
<220> FEATURE:
<221> NAME/KEY: MISC_FEATURE
<222> LOCATION: (9)..(9)
<223> OTHER INFORMATION: tert-butyl-L-alanine

<400> SEQUENCE: 131

Arg Arg Phe Trp Xaa Cys Thr Arg Xaa
1               5

<210> SEQ ID NO 132
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: D-cysteine
<220> FEATURE:
<221> NAME/KEY: MISC_FEATURE
<222> LOCATION: (9)..(9)
<223> OTHER INFORMATION: tert-butyl-L-alanine

<400> SEQUENCE: 132

Arg Arg Phe Trp Xaa Cys Thr Arg Xaa
1               5

<210> SEQ ID NO 133
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (9)..(9)
<223> OTHER INFORMATION: tert-butyl-L-alanine

<400> SEQUENCE: 133

Arg Arg Phe Trp Cys Cys Thr Arg Xaa
1               5

<210> SEQ ID NO 134
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: 3-(1-Naphthyl)-L-alanine
<220> FEATURE:
<221> NAME/KEY: MISC_FEATURE
<222> LOCATION: (11)..(11)
<223> OTHER INFORMATION: tert-butyl-L-alanine

<400> SEQUENCE: 134

Cys Arg Arg Arg Phe Xaa Gln Cys Thr Arg Xaa
1               5                   10
```

```
<210> SEQ ID NO 135
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: 3-(2-Naphthyl)-L-alanine
<220> FEATURE:
<221> NAME/KEY: MISC_FEATURE
<222> LOCATION: (11)..(11)
<223> OTHER INFORMATION: tert-butyl-L-alanine

<400> SEQUENCE: 135

Cys Arg Arg Arg Phe Xaa Gln Cys Thr Arg Xaa
1               5                   10

<210> SEQ ID NO 136
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 136

Cys Arg Arg Arg Phe Trp Gln Xaa Thr Arg Xaa
1               5                   10

<210> SEQ ID NO 137
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: 3-(1-Naphthyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 137

Cys Arg Arg Arg Xaa Trp Gln Xaa Thr Arg Xaa
1               5                   10

<210> SEQ ID NO 138
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: 3-(2-Naphthyl)-L-alanine
```

```
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 138

Cys Arg Arg Arg Xaa Trp Gln Xaa Thr Arg Xaa
1               5                   10

<210> SEQ ID NO 139
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: 3-(2-Naphthyl)-D-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 139

Cys Arg Arg Arg Xaa Trp Gln Xaa Thr Arg Xaa
1               5                   10

<210> SEQ ID NO 140
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 140

Cys Xaa Arg Arg Xaa Trp Gln Xaa Thr Arg Xaa
1               5                   10

<210> SEQ ID NO 141
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(3)
<223> OTHER INFORMATION: D-arginine
```

```
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 141

Cys Xaa Xaa Arg Xaa Trp Gln Xaa Thr Arg Xaa
1               5                   10

<210> SEQ ID NO 142
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: D-arginine
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 142

Cys Arg Xaa Arg Xaa Trp Gln Xaa Thr Arg Xaa
1               5                   10

<210> SEQ ID NO 143
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 143

Cys Xaa Arg Arg Xaa Trp Pro Xaa Thr Arg Xaa
1               5                   10
```

```
<210> SEQ ID NO 144
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (7)..(7)
<223> OTHER INFORMATION: penicillamine
<220> FEATURE:
<221> NAME/KEY: MISC_FEATURE
<222> LOCATION: (8)..(8)
<223> OTHER INFORMATION: tert-butyl-L-alanine
<220> FEATURE:
<221> NAME/KEY: MISC_FEATURE
<222> LOCATION: (11)..(11)
<223> OTHER INFORMATION: tert-butyl-L-alanine

<400> SEQUENCE: 144

Cys Xaa Arg Arg Xaa Trp Xaa Xaa Thr Arg Xaa
1               5                   10

<210> SEQ ID NO 145
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (7)..(7)
<223> OTHER INFORMATION: penicillamine
<220> FEATURE:
<221> NAME/KEY: MISC_FEATURE
<222> LOCATION: (8)..(8)
<223> OTHER INFORMATION: tert-butyl-L-alanine
<220> FEATURE:
<221> NAME/KEY: MISC_FEATURE
<222> LOCATION: (11)..(11)
<223> OTHER INFORMATION: tert-butyl-L-alanine

<400> SEQUENCE: 145

Cys Xaa Arg Arg Xaa Xaa Xaa Xaa Thr Arg Xaa
1               5                   10

<210> SEQ ID NO 146
<211> LENGTH: 11
<212> TYPE: PRT
<213> ORGANISM: Artificial Sequence
<220> FEATURE:
<223> OTHER INFORMATION: synthetic construct
```

```
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: 3-(2-Naphthyl)-L-alanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (7)..(7)
<223> OTHER INFORMATION: penicillamine
<220> FEATURE:
<221> NAME/KEY: MISC_FEATURE
<222> LOCATION: (8)..(8)
<223> OTHER INFORMATION: tert-butyl-L-alanine
<220> FEATURE:
<221> NAME/KEY: MISC_FEATURE
<222> LOCATION: (11)..(11)
<223> OTHER INFORMATION: tert-butyl-L-alanine

<400> SEQUENCE: 146

Cys Xaa Arg Arg Xaa Xaa Xaa Xaa Thr Arg Xaa
1               5                   10

<210> SEQ ID NO 147
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 147

Cys Xaa Arg Arg Xaa Trp Pro Xaa Thr Arg Xaa
1               5                   10

<210> SEQ ID NO 148
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (8)..(8)
<223> OTHER INFORMATION: penicillamine
```

```
<220> FEATURE:
<221> NAME/KEY: MISC_FEATURE
<222> LOCATION: (11)..(11)
<223> OTHER INFORMATION: tert-butyl-L-alanine

<400> SEQUENCE: 148

Cys Xaa Arg Arg Xaa Trp Pro Xaa Thr Arg Xaa
1               5                   10

<210> SEQ ID NO 149
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 149

Cys Xaa Arg Arg Xaa Xaa Pro Xaa Thr Arg Xaa
1               5                   10

<210> SEQ ID NO 150
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 150

Cys Xaa Arg Arg Xaa Xaa Pro Xaa Thr Arg Xaa
1               5                   10
```

```
<210> SEQ ID NO 151
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (7)..(7)
<223> OTHER INFORMATION: L-piperidine-2-carboxylic acid
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 151

Cys Xaa Arg Arg Xaa Xaa Xaa Xaa Thr Arg Xaa
1               5                   10

<210> SEQ ID NO 152
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (7)..(7)
<223> OTHER INFORMATION: L-piperidine-2-carboxylic acid
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 152

Cys Xaa Arg Arg Xaa Xaa Xaa Xaa Thr Arg Xaa
1               5                   10

<210> SEQ ID NO 153
<211> LENGTH: 11
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 153

Cys Xaa Arg Arg Xaa Trp Pro Xaa Thr Arg Xaa
1               5                   10

<210> SEQ ID NO 154
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (6)..(6)
<223> OTHER INFORMATION: 3-(3-benzothienyl)-L-alanine
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 154

Cys Xaa Arg Arg Xaa Xaa Pro Xaa Thr Arg Xaa
1               5                   10

<210> SEQ ID NO 155
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: D-arginine
<220> FEATURE:
<221> NAME/KEY: MISC_FEATURE
<222> LOCATION: (5)..(5)
<223> OTHER INFORMATION: Napthylalanine
<220> FEATURE:
<221> NAME/KEY: MISC_FEATURE
<222> LOCATION: (6)..(6)
<223> OTHER INFORMATION: 3-(3-benzothienyl)-L-alanine
```

```
<220> FEATURE:
<221> NAME/KEY: MISC_FEATURE
<222> LOCATION: (7)..(7)
<223> OTHER INFORMATION: L-piperidine-2-carboxylic acid
<220> FEATURE:
<221> NAME/KEY: MISC_FEATURE
<222> LOCATION: (8)..(8)
<223> OTHER INFORMATION: penicillamine
<220> FEATURE:
<221> NAME/KEY: MISC_FEATURE
<222> LOCATION: (11)..(11)
<223> OTHER INFORMATION: tert-butyl-L-alanine

<400> SEQUENCE: 155

Cys Xaa Arg Arg Xaa Xaa Xaa Xaa Thr Arg Xaa
1               5                   10

<210> SEQ ID NO 156
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
<220> FEATURE:
<221> NAME/KEY: MISC_FEATURE
<222> LOCATION: (3)..(3)
<223> OTHER INFORMATION: D-Napthylalanine
<220> FEATURE:
<221> NAME/KEY: MISC_FEATURE
<222> LOCATION: (5)..(6)
<223> OTHER INFORMATION: D-arginine

<400> SEQUENCE: 156

Xaa Xaa Xaa Arg Xaa Xaa
1               5

<210> SEQ ID NO 157
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: L-piperidine-2-carboxylic acid
<220> FEATURE:
<221> NAME/KEY: MISC_FEATURE
<222> LOCATION: (2)..(2)
<223> OTHER INFORMATION: Napthylalanine
<220> FEATURE:
<221> NAME/KEY: MISC_FEATURE
<222> LOCATION: (3)..(3)
<223> OTHER INFORMATION: D-Napthylalanine
<220> FEATURE:
<221> NAME/KEY: MISC_FEATURE
<222> LOCATION: (5)..(6)
<223> OTHER INFORMATION: D-arginine

<400> SEQUENCE: 157

Xaa Xaa Xaa Arg Xaa Xaa
1               5
```

```
<210> SEQ ID NO 158
<211> LENGTH: 10
<212> TYPE: PRT
<213> ORGANISM: Artificial Sequence
<220> FEATURE:
<223> OTHER INFORMATION: synthetic construct

<400> SEQUENCE: 158

Ala Asn Ser Arg Trp Pro Thr Ser Ile Ile
1               5                   10
```